US011584741B2

United States Patent
Lawrence et al.

(10) Patent No.: US 11,584,741 B2
(45) Date of Patent: Feb. 21, 2023

(54) CRYSTALLINE FORMS OF 4-(5-(4,7-DIMETHYLBENZOFURAN-2-YL)-1,2,4-OXADIAZOL-3-YL)BENZOIC ACID AND PROCESSES FOR THEIR PREPARATION

(71) Applicant: King's College London, Greater London (GB)

(72) Inventors: Ronnie Maxwell Lawrence, Stevenage (GB); Edwin Aret, Weert (NL); Alan David Borthwick, London (GB); Jane Theresa Brown, Nottingham (GB); Jonathan Patrick Thomas Corcoran, London (GB); Maria Beatriz De Castro Vasconcelos Goncalves, London (GB); Sarkis Barrett Kalindjian, Bansted (GB)

(73) Assignee: King's College London, London (GB)

( * ) Notice: Subject to any disclaimer, the term of this patent is extended or adjusted under 35 U.S.C. 154(b) by 222 days.

(21) Appl. No.: 17/109,758

(22) Filed: Dec. 2, 2020

(65) Prior Publication Data

US 2021/0230151 A1    Jul. 29, 2021

Related U.S. Application Data

(62) Division of application No. 16/311,318, filed as application No. PCT/EP2017/064802 on Jun. 16, 2017, now Pat. No. 10,870,644.

(30) Foreign Application Priority Data

Jun. 22, 2016 (GB) .................................. 1610867

(51) Int. Cl.
C07D 413/04    (2006.01)

(52) U.S. Cl.
CPC ........ *C07D 413/04* (2013.01); *C07B 2200/13* (2013.01)

(58) Field of Classification Search
CPC combination set(s) only.
See application file for complete search history.

(56) References Cited

U.S. PATENT DOCUMENTS

| | | | |
|---|---|---|---|
| 5,998,459 | A | 12/1999 | Tsuda et al. |
| 6,110,959 | A | 8/2000 | Tagami et al. |
| 6,121,309 | A | 9/2000 | Tagami et al. |
| 6,258,811 | B1 | 7/2001 | Yamauchi et al. |
| 6,329,402 | B1 | 12/2001 | Kikuchi et al. |
| 6,355,669 | B1 | 3/2002 | Yamauchi et al. |
| 6,358,995 | B1 | 3/2002 | Tagami et al. |
| 6,992,096 | B2 | 1/2006 | Karp et al. |
| 9,994,559 | B2 | 6/2018 | Borthwick et al. |
| 10,385,044 | B2 | 8/2019 | Borthwick et al. |
| 10,870,644 | B2 | 12/2020 | Lawrence et al. |
| 2003/0045546 | A1 | 3/2003 | Cai et al. |
| 2004/0152699 | A1 | 8/2004 | Arora et al. |
| 2004/0204461 | A1 | 10/2004 | Karp et al. |
| 2005/0154012 | A1 | 7/2005 | Cai et al. |
| 2009/0176837 | A1 | 7/2009 | Olsson et al. |
| 2009/0253699 | A1 | 10/2009 | Almstead et al. |
| 2011/0081297 | A1 | 4/2011 | Barrow et al. |
| 2017/0327489 | A1 | 11/2017 | Borthwick et al. |

FOREIGN PATENT DOCUMENTS

| | | |
|---|---|---|
| EP | 0889032 A1 | 1/1999 |
| EP | 0930075 A1 | 7/1999 |
| EP | 1025857 A1 | 8/2000 |
| EP | 2314569 A1 | 4/2011 |
| JP | 200381832 A | 3/2003 |
| JP | 2003081832 A | 3/2003 |
| WO | 0057900 A2 | 10/2000 |
| WO | 03062230 A1 | 7/2003 |
| WO | 2005077373 A2 | 8/2005 |
| WO | 2008057933 A2 | 5/2008 |
| WO | 2008057930 A2 | 6/2008 |
| WO | 2008063842 A2 | 2/2009 |
| WO | 2009146343 A1 | 12/2009 |
| WO | 2011072281 A1 | 6/2011 |
| WO | 2016097004 A1 | 6/2016 |

(Continued)

OTHER PUBLICATIONS

Agudo et al., 2010, "A retinoic acid receptor beta agonist (CD2019) overcomes inhibition of axonal outgrowth via phosphoinositide 3-kinase signalling in the injured adult spinal cord", Neurobiology of Disease, vol. 37, pp. 147-155.

Bastien et al., 2004, "Nuclear retinoid receptors and the transcription of retinoid-target genes", Gene, vol. 328, pp. 1-16.

Bernard et al., 1992, "Identification of synthetic retinoids with selectivity for human nuclear retinoic acid receptor gamma", Biochemical and Biophysical Research Communications, vol. 186, No. 2, pp. 977-983.

Bradbury et al., 2002, "Chondroitinase ABC promotes functional recovery after spinal cord injury", Nature, vol. 416, pp. 636-640.

Cho et al., 2010, "The palladium-catalyzed trifluoromethylation of aryl chlorides", Science, vol. 328, No. 5986, pp. 1679-1681.

Corcoran et al., 1999, "Nerve growth factor acts via retinoic acid synthesis to stimulate neurite outgrowth", Nature Neuroscience, vol. 2, No. 4, pp. 307-308.

(Continued)

*Primary Examiner* — Kathrien A Cruz
(74) *Attorney, Agent, or Firm* — McNeill Baur PLLC

(57) ABSTRACT

The present invention pertains generally to the field of therapeutic compounds, and more specifically to crystalline forms of 4-(5-(4,7-dimethylbenzofuran-2-yl)-1,2,4-oxadiazol-3-yl)benzoic acid (referred to herein as "BHBA-001"), which, inter alia, is a (selective) retinoic acid receptor beta (RARβ) (e.g., RARβ2) agonist. The present invention also pertains to pharmaceutical compositions comprising such crystalline forms, and the use of such crystalline forms and compositions, both in vitro and in vivo, to (selectively) activate RARβ (e.g., RARβ2), to cause or promote neurite development, neurite outgrowth, and/or neurite regeneration, and in the treatment of diseases and conditions that are mediated by RARβ (e.g., RARβ2), that are ameliorated by the activation of RARβ (e.g., RARβ2), etc., including, e.g., neurological injuries such as spinal cord injuries.

13 Claims, 15 Drawing Sheets

(56) References Cited

FOREIGN PATENT DOCUMENTS

WO          2017220446 A1    12/2017

OTHER PUBLICATIONS

Corcoran et al., 2000, "The role of retinoic acid receptors in neurite outgrowth from different populations of embryonic mouse dorsal root ganglia", Journal of Cell Science, vol. 113, pp. 2567-2574.
Corcoran et al., 2002, "Retinoic acid receptor beta2 and neurite outgrowth in the adult mouse spinal cord in vitro", Journal of Cell Science, vol. 115, pp. 3779-3786.
Delescluse et al., 1991, "Selective high affinity retinoic acid receptor alpha or betagamma ligands," Molecular Pharmacology, vol. 40, pp. 556-562.
Goncalves et al., 2009, "Sequential RARbeta and alpha signalling in vivo can induce adult forebrain neural progenitor cells to differentiate into neurons through Shh and FGF signalling pathways", Developmental Biology, vol. 326, pp. 305-313.
He et al., 2004, "The nogo signaling pathway for regeneration block", Annual Review of Neuroscience, vol. 27, pp. 341-368.
Imazaki et al., 2012, "Ruthenium-Catalyzed Transformation of Aryl and Alkenyl Triflates to Halides", Journal of the American Chemical Society, vol. 134, No. 36, pp. 14760-14763.
International Preliminary Report on Patentability (IPRP) for International patent application No. PCT/EP2017/064802, dated Jan. 3, 2019. 8 pages.
International Search Report (ISR) for International patent application No. PCT/EP2017/064802, dated Aug. 23, 2017. 4 pages.
Kikuchi et al., 2000, "Synthesis and structure-activity relationships of 5,6,7,8-tetrahydro-5,5,8,8-tetramethyl-2-quinoxaline derivatives with retinoic acid receptor a activity", Journal of Medicinal Chemistry, vol. 43, pp. 409-419.
Kwon et al., 2001, "Spinal cord regeneration: from gene to transplants", Spine, vol. 26, No. 24S, pp. S13-S22.
Leid et al., 1992, "Multiplicity generates diversity in the retinoic acid signalling pathways", Trends in Biochemical Sciences, vol. 17, pp. 427-433.
Lu et al., 2004, "Combinatorial therapy with neurotrophins and cAMP promotes axonal regeneration beyond sites of spinal cord injury", The Journal of Neuroscience, vol. 24, No. 28, pp. 6402-6409.
Lund et al., 2005, "Discovery of a potent, orally available, and isoform-selected retinoica acid β2 receptor agonist", Journal of Medicinal Chemistry, vol. 48, No. 24, pp. 7517-7519.
Maden et al., 1996, "Vitamin A-deficient quail embryos have half a hindbrain and other neural defects", Current Biology, vol. 6, No. 4, pp. 417-426.
McOmie et al., 1968, "Demethylation of aryl methyl ethers by boron tribromide", Tetrahedron, vol. 24, No. 5, pp. 2289-2292.
Pan et al., 2011, "An Improved Palladium-Catalyzed Conversion of Aryl and Vinyl Triflates to Bromides and Chlorides", Organic Letters, vol. 13, No. 18, pp. 4974-4976.
Quinn et al., 1991, "Enhanced neuronal regeneration by retinoic acid of murine dorsal root ganglia and of fetal murine and human spinal cord in vitro", In Vitro Cellular & Developmental Biology, vol. 27 A, No. 1, pp. 55-62.
Ritter, 1993, "Synthetic transformations of vinyl and aryl triflates", Synthesis, vol. 8, pp. 735-762.
Schnell et al., 1994, "Neurotrophin-3 enhances sprouting of corticospinal tract during development and after adult spinal cord lesion", Nature, vol. 367, pp. 170-173.
Search Report for United Kingdom patent application No. GB 1610867.2, dated Apr. 21, 2017. 4 pages.
Seino et al., 2004, "Prevention of acute and chronic allograft rejection by a novel retinoic acid receptor-a-selective agonist", International Immunology, vol. 16, No. 5, pp. 665-673.
So et al., 2006, "Interactions between retinoic acid, nerve growth factor and sonic hedgehog signalling pathways in neurite outgrowth", Developmental Biology, vol. 298, pp. 167-175.
Watson et al., 2009, "Formation of ArF from LPdAr(F): Catalytic conversion of aryl triflates to aryl fluorides", Science, vol. 325, pp. 1661-1664.
White et al., 1998, "Defects in embryonic hindbrain development and fetal resorption resulting from vitamin A deficiency in the rat are prevented by feeding pharmacological levels of all-trans-retinoic acid", Proceedings of the National Academy of Science USA, vol. 95, pp. 13459-12364.
Williams et al., 2005, "A complementary peptide approach applied to the design of novel semaphorin/neuropilin antagonists", Journal of Neurochemistry, vol. 92, pp. 1180-1190.
Wong et al., 2006, "Retinoic acid receptor beta2 promotes functional regeneration of sensory axons in the spinal cord", Nature Neuroscience, vol. 9, No. 2, pp. 243-250.
Written Opinion of the International Search Authority (WO ISA) for International patent application No. PCT/EP2017/064802, dated Aug. 23, 2017. 7 pages.
Yip et al., 2006, "Lentiviral vector expressing retinoic acid receptor beta2 promotes recovery of function after corticospinal tract injury in the adult rat spinal cord", Human Molecular Genetics, vol. 15, No. 21, pp. 3107-3118.
Yoshimura et al., 2000, "Discovery of novel and potent retinoic acid receptor a agonists: synthesis and evaluation of benzofuranylpyrrole and benzothiophenylpyrrole derivatives", Journal of Medicinal Chemistry, vol. 43, No. 15, pp. 2929-2937.
Barrot, 2012, "Tests and models of nociception and pain in rodents", Neuroscience, vol. 211, pp. 39?50.
Chen et al., 2014, "Presynaptic GABAergic inhibition regulated by BDNF contributes to neuropathic pain induction", Nat Commun, vol. 5, p. 5331.
Colloca et al., 2017, "Neuropathic pain", Nat Rev Dis Primers, vol. 3, p. 17002.
Constandil et al., 2011, "Involvement of spinal cord BDNF in the generation and maintenance of chronic neuropathic pain in rats", Brain Res Bull, vol. 86, No. 5-6, pp. 454-459.
Co-Pending U.S. Appl. No. 17/612,074, filed Nov. 17, 2021.
Geng et al., 2010, "Contribution of the spinal cord BDNF to the development of neuropathic pain by activation of the NR2B-containing NMDA receptors in rats with spinal nerve ligation", Exp Neurol, vol. 222, No. 2, pp. 256-266.
Goncalves et al., 2019, "Discovery and lead optimisation of a potent, selective and orally bioavailable RARβ agonist for the potential treatment of nerve injury", Bioorg. Med. Chem. Lett., vol. 29, pp. 995-1000.
Goncalves et al., 2019, "RARβ Agonist Drug (C286) Demonstrates Efficacy in a Pre-clinical Neuropathic Pain Model Restoring Multiple Pathways via DNA Repair Mechanisms," iScience, vol. 20, pp. 554-566.
Hargreaves et al., 1998, "A new and sensitive method for measuring thermal nociception in cutaneous hyperalgesia", Pain, vol. 32, No. 1, p. 77-88.
Huang et al., 2016, "A Comparison of Surgical Invasions for Spinal Nerve Ligation with or without Paraspinal Muscle Removal in a Rat Neuropathic Pain Model", Biomed Res Int, p. 6741295.
International Search Report (ISR) for International patent application No. PCT/EP2020/064969, dated Aug. 25, 2020, 5 pages.
Jensen et al., 2014, "Allodynia and hyperalgesia in neuropathic pain: clinical manifestations and mechanisms", Lancet Neurol, vol. 13, No. 9, pp. 924-935.
Kim et al., 1992, "An experimental model for peripheral neuropathy produced by segmental spinal nerve ligation in the rat", Pain, vol. 50, No. 3, pp. 355-363.
Meacham et al., 2017, "Neuropathic Pain: Central vs. Peripheral Mechanisms", Curr Pain Headache Rep, vol. 21, No. 6, p. 28.
Raghavendra et al., 2003, "Inhibition of microglial activation attenuates the development but not existing hypersensitivity in a rat model of neuropathy", J. Pharmacol. Exp. Ther., vol. 306, pp. 624-630.

(56) References Cited

OTHER PUBLICATIONS

Schafers et al., 2003A, "Tumor necrosis factor-alpha induces mechanical allodynia after spinal nerve ligation by activation of p38 MAPK in primary sensory neurons", J Neurosci, vol. 23, No. 7, pp. 2517-2521.

Schafers et al., 2003B, "Spinal nerve ligation induces transient upregulation of tumor necrosis factor receptors 1 and 2 in injured and adjacent uninjured dorsal root ganglia in the rat", Neurosci Lett, vol. 347, No. 3, pp. 179-182.

Search Report for United Kingdom patent application No. GB 1907647.0, dated Nov. 5, 2019. 4 pages.

Seltzer et al., 1990, "A novel behavioral model of neuropathic pain disorders produced in rats by partial sciatic nerve injury", Pain, vol. 43, No. 2, pp. 205-218.

Written Opinion for International patent application No. PCT/EP2020/064969, dated Aug. 25, 2020, 8 pages.

Brittain, "Polymorphism in Pharmaceutical Solids," Methods for the Characterization of Polymorphs pp. 234-238 (1999).

CRYSTALLINE FORMS OF 4-(5-(4,7-DIMETHYLBENZOFURAN-2-YL)-1,2,4-OXADIAZOL-3-YL)BENZOIC ACID AND PROCESSES FOR THEIR PREPARATION

RELATED APPLICATION

This application is a division of U.S. application Ser. No. 16/311,318, filed Dec. 19, 2018, which is a national phase entry pursuant to 35 U.S.C. § 371 of International Application No. PCT/EP2017/064802, filed Jun. 16, 2017, which is related to, and claims priority of, United Kingdom patent application number 1610867.2 filed 22 Jun. 2016, the contents of which are incorporated herein by reference in their entirety for any purpose.

TECHNICAL FIELD

The present invention pertains generally to the field of therapeutic compounds, and more specifically to crystalline forms of 4-(5-(4,7-dimethylbenzofuran-2-yl)-1,2,4-oxadiazol-3-yl)benzoic acid (referred to herein as "BHBA-001"), which, inter alia, is a (selective) retinoic acid receptor beta (RARβ) (e.g., RARβ2) agonist. The present invention also pertains to pharmaceutical compositions comprising such crystalline forms, and the use of such crystalline forms and compositions, both in vitro and in vivo, to (selectively) activate RARβ (e.g., RARβ2), to cause or promote neurite development, neurite outgrowth, and/or neurite regeneration, and in the treatment of diseases and conditions that are mediated by RARβ (e.g., RARβ2), that are ameliorated by the activation of RARβ (e.g., RARβ2), etc., including, e.g., neurological injuries such as spinal cord injuries.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Nerve Injury

As yet, there are no effective treatments for nerve injuries including spinal cord injuries (SCI), stroke, and peripheral nerve injuries. The inventors have identified a novel signalling mechanism—the retinoid signalling pathway—that can be stimulated in models of nerve injury leading to axonal outgrowth and functional recovery. See, for example, Maden and Corcoran, 2000. This pathway is activated by retinoic acid (RA) binding to the retinoic acid receptor (RAR) that acts in the nucleus to drive the synthesis of RNA and hence produces proteins for axonal outgrowth. The inventors have shown that the RARβ2 subtype is specifically involved in this process.

Retinoid Signalling and Neurite Outgrowth

There are at least three causes for the lack of axonal outgrowth of central nervous system (CNS) neurons after spinal cord injury. First: the presence of growth inhibiting molecules, including Nogo-A, myelin-associated glycoprotein (MAG) and oligodendrocyte myelin glycoprotein (Omgp) (see, e.g., He and Koprivica, 2004). Second: insufficiency of growth-promoting factors, which are well-known for their ability to promote neurite outgrowth in vitro and to induce some axonal outgrowth when administered to injured cord (see, e.g., Schnell et al., 1994; Lu et al., 2004). Third: the lack of an appropriate 'growth programme' by damaged neurones (see, e.g., Kwon and Tetzlaff, 2001). One factor that can induce such a growth programme is RA signalling (see, e.g., Quinn and De Boni, 1991). This is mediated by RARβ and retinoid X receptors (RXRs), both of which have three subtypes (α,β, and γ and various isoforms) (see, e.g., Bastien and Rochette-Egly, 2004). Transcription occurs when RA binds to an RAR/RXR heterodimer which then binds to retinoic acid response elements (RAREs) located in the regulatory regions of target genes (see, e.g., Bastien and Rochette-Egly, 2004).

RARβ2 Signalling Mediates Neurite Outgrowth

Retinoid signalling is important for the development of the embryo. When the nervous system is deprived of RA during development, neurite outgrowth fails, for example, in the RA deficient embryo (see, e.g., Maden et al., 1996; White et al., 1998). By using a panel of RAR agonists, the inventors have shown that RARβ signalling is required for retinoid mediated neurite outgrowth of neurons, whereas RARα or RARγ signalling has no effect (see, e.g., Corcoran et al., 2000). More specifically it is the activation of RARβ2 that mediates this effect (see, e.g., Corcoran et al., 2000) and this is auto-regulated by its ligand (see, e.g., Leid et al., 1992). Activation of RARβ2 by retinoids results in neurite outgrowth of cultured embryonic dorsal root ganglia (DRG), spinal cord, and adult DRG (see, e.g., Corcoran et al., 2000; Corcoran and Maden, 1999; So et al., 2006; Corcoran et al., 2002). When RARβ2 is transduced into cultured adult rodent spinal cord explants, which do not normally express this receptor, neurite outgrowth occurs (see, e.g., Corcoran et al., 2002).

RARβ2 Signalling Mediates Axonal Outgrowth

A test of the importance of RARβ signalling in axonal outgrowth comes from gene-deleted RARβ null mice. In a peripheral nerve crush model, axonal outgrowth is impeded compared to normal mice which express RARβ2 in their DRG neurons (see, e.g., Corcoran and Maden, 1999; So et al., 2006).

Furthermore, it can be demonstrated that RARβ2 expression is essential for axonal outgrowth in vivo by overexpressing it in models of spinal cord injury. In rodents, models of avulsion (where the axons of the peripheral sensory axons are damaged leading to forelimb paralysis), the overexpression of RARβ2 into the neurons of the injured DRG leads to axonal outgrowth across the dorsal root entry zone (DREZ) and back into the spinal cord leading to functional recovery (see, e.g., Wong et al., 2006).

Another model of spinal cord lesion is one that severs the corticospinal tract (CST). The cell bodies of these CST neurons are located in the brain. The CST forms the major descending pathway in the dorsal columns of the spinal cord and their damage results in functional impairments of some motor tasks. The CST lesion can be achieved by the crush of the spinal cord at the level of C4 in rodents. This results in loss of function of the forelimbs. Recently, it has been demonstrated that overexpression of RARβ2 by lentiviral vectors in adult CST neurons results in outgrowth of CST axons and functional recovery of the forelimb (see, e.g., Yip et al., 2006).

The inventors have now shown that RARβ agonists are likely to be useful in the treatment of nerve injury. RARβ agonists initiate axonal outgrowth in models of nerve injury and functional recovery occurs. Studies demonstrating these findings are described in more detail in the Examples below.

Lund et al., 2005, describes certain 4,4'-biphenylcarboxylic acid compounds that allegedly have RARβ2 agonist activity.

Kikuchi et al., 2000, describes certain tetrahydro-tetramethyl-2-quinoxaline compounds that allegedly have RARα agonist activity.

Yoshimura et al., 2000, describes certain benzofuranyl-pyrrole and benzothiophenyl-pyrrole compounds that allegedly have RARα agonist activity.

Seino et al., 2004, describes the use of an RARα agonist, ER-38925, in the prevention of acute and chronic allograft rejection.

Tagami et al., 2000a, Tagami et al., 2000b, and Tagami et al., 2002 all describe certain compounds allegedly exhibiting retinoic acid receptor agonism.

Kikuchi et al., 2001 describes certain compound allegedly having the activity of retinoic acid.

Tsuda et al., 1999, describes certain compounds which allegedly are useful in the treatment of pollakiuria and urinary incontinence.

Cai et al., 2003 and Cai et al., 2005 describe certain compounds which allegedly are activators of caspases and inducers of apoptosis.

Olsson et al., 2009, describes certain compounds that allegedly have activity at RARβ2 receptors.

BHBA-001

Borthwick et al., 2016 describes certain bicycloheteroaryl-heteroaryl-benzoic acid (BHBA) compounds, their activity in (selectively) activating RARβ2 (e.g., RARβ2), and their use in the treatment of diseases and conditions that are mediated by RARβ (e.g., RARβ2), including, e.g., neurological injuries such as spinal cord injuries.

Borthwick et al., 2016 describes the preparation of BHBA-001 in Synthesis 1 therein. In the last step, the methyl ester was deprotected by treatment with aqueous LiOH. The resulting mixture was cooled to room temperature, acidified with HCl, and the resulting solid was collected by filtration. The solid was dissolved in MeOH and evaporated to dryness to give BHBA-001 as "a white solid".

SUMMARY OF THE INVENTION

The present invention relates to crystalline forms of 4-(5-(4,7-dimethylbenzofuran-2-yl)-1,2,4-oxadiazol-3-yl) benzoic acid (shown below, and referred to herein as "BHBA-001").

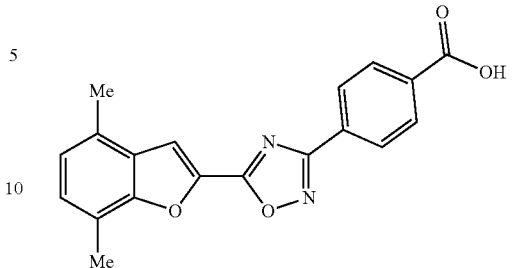

BHBA-001

As described herein, four distinct crystalline forms of BHBA-001 have been identified (i.e., Forms 1, 2, 3, and 4).

One aspect of the present invention is a crystalline form of BHBA-001, as described herein.

In one embodiment, the crystalline form of BHBA-001 is Form 1, as described herein.

In one embodiment, the crystalline form of BHBA-001 is Form 2, as described herein.

In one embodiment, the crystalline form of BHBA-001 is Form 3, as described herein.

In one embodiment, the crystalline form of BHBA-001 is Form 4, as described herein.

Notably, crystalline Form 4 of BHBA-001 has (substantially) better physical chemical properties (e.g., anhydrous, low solvent retention, low hygroscopicity, long term stability, suitable particle size, etc.) than the other forms.

Another aspect of the present invention pertains to a composition (e.g., a pharmaceutical composition) comprising a crystalline form of BHBA-001 (e.g., Form 4), as described herein and a pharmaceutically acceptable carrier, diluent, or excipient.

Another aspect of the present invention pertains to a method of preparing a composition (e.g., a pharmaceutical composition) comprising the step of mixing a crystalline form of BHBA-001 (e.g., Form 4), as described herein, and a pharmaceutically acceptable carrier or diluent.

Another aspect of the present invention pertains to use of a crystalline form of BHBA-001 (e.g., Form 4), as described herein, in a method of activating retinoic acid receptor β (RARβ) (for example, RARβ2) in vitro or in vivo, for example, in a method comprising contacting RARβ (for example, RARβ2) with an effective amount of a crystalline form of BHBA-001 (e.g., Form 4), or BHBA-001 as obtained from a crystalline form of BHBA-001 (e.g., Form 4).

Another aspect of the present invention pertains to use of a crystalline form of BHBA-001 (e.g., Form 4), as described herein, in a method of selectively activating retinoic acid receptor β (RARβ) (for example, RARβ2) (e.g., with respect to RARα and/or RARγ), in vitro or in vivo, for example, in a method comprising contacting RARβ (for example, RARβ2) with an effective amount of a crystalline form of BHBA-001 (e.g., Form 4), or BHBA-001 as obtained from a crystalline form of BHBA-001 (e.g., Form 4).

Another aspect of the present invention pertains to use of a crystalline form of BHBA-001, as described herein, in a method of activating retinoic acid receptor β (RARβ) (for example, RARβ2), in a neuronal cell, in vitro or in vivo, for example, in a method comprising contacting the cell with an effective amount of a crystalline form of BHBA-001 (e.g., Form 4), or BHBA-001 as obtained from a crystalline form of BHBA-001 (e.g., Form 4).

Another aspect of the present invention pertains to use of a crystalline form of BHBA-001, as described herein, in a method of selectively activating retinoic acid receptor β (RARβ) (for example, RARβ2), in a neuronal cell, in vitro or in vivo, for example, in a method comprising contacting the cell with an effective amount of a crystalline form of BHBA-001 (e.g., Form 4), or BHBA-001 as obtained from a crystalline form of BHBA-001 (e.g., Form 4).

Another aspect of the present invention pertains to use of a crystalline form of BHBA-001 (e.g., Form 4), as described herein, in a method of causing or promoting neurite development, neurite outgrowth, and/or neurite regeneration, for example, in a method comprising contacting a neuron, in vitro or in vivo, with an effective amount of a crystalline form of BHBA-001 (e.g., Form 4), or BHBA-001 as obtained from a crystalline form of BHBA-001 (e.g., Form 4).

Another aspect of the present invention pertains to a crystalline form of BHBA-001 (e.g., Form 4), as described herein, for use in a method of treatment of the human or animal body by therapy.

Another aspect of the present invention pertains to use of a crystalline form of BHBA-001 (e.g., Form 4), as described herein, in the manufacture of a medicament for use in treatment.

Another aspect of the present invention pertains to a method of treatment comprising administering to a subject in need of treatment a therapeutically effective amount of a crystalline form of BHBA-001 (e.g., Form 4), or BHBA-001 as obtained from a crystalline form of BHBA-001 (e.g., Form 4), as described herein, preferably in the form of a pharmaceutical composition.

In one embodiment, the treatment is treatment of, for example:
- a neurological injury;
- an injury of the central nervous system (CNS);
- an injury of the peripheral nervous system (PNS);
- a nerve injury;
- a PNS nerve injury;
- a CNS nerve injury;
- a spinal cord injury;
- a spinal cord injury caused by trauma;
- an optic nerve injury;
- an optic nerve injury caused by glaucoma;
- a neuropathy;
- a PNS neuropathy;
- a CNS neuropathy;
- a spinal cord neuropathy;
- an optic nerve neuropathy;
- diabetic neuropathy (i.e., neuropathy associated with diabetes mellitus); AIDS neuropathy (i.e., neuropathy associated with AIDS);
- leprotic neuropathy (i.e., neuropathy associated with leprosy);
- peripheral neuropathy (for example, polyneuropathy, mononeuropathy, mononeuritis multiplex, or autonomic neuropathy);
- a neurodegenerative disorder;
- a cognitive disorder, memory impairment, memory deficit, senile dementia, Alzheimer's disease, early stage Alzheimer's disease, intermediate stage Alzheimer's disease, late stage Alzheimer's disease, cognitive impairment, or mild cognitive impairment;
- Huntington's disease;
- Parkinson's disease;
- motor neurone disease;
- localised paralysis;
- Bell's palsy;
- neurally-based impotence;
- neurally-based impotence caused by nerve trauma following radical prostatectomy;
- paralysis, for example, monoplegia, quadriplegia, or paraplegia;
- a neurological disorder caused by a neurological injury;
- a neurological disorder caused by a neuropathy; or
- a neurological injury caused by a neuropathy.

Another aspect of the present invention pertains to a kit comprising (a) a crystalline form of BHBA-001, as described herein, preferably provided as a pharmaceutical composition and in a suitable container and/or with suitable packaging; and (b) instructions for use, for example, written instructions on how to administer the compound.

Another aspect of the invention pertains to a method of preparing a crystalline form of BHBA-001 (e.g., Form 4), as described herein.

Another aspect of the present invention pertains to a crystalline form of BHBA-001 (e.g., Form 4), as described herein, that is obtainable by a method of preparing a crystalline form of BHBA-001 (e.g., Form 4), as described herein.

Another aspect of the present invention pertains to a crystalline form of BHBA-001 (e.g., Form 4), as described herein, that is obtained by a method of preparing a crystalline form of BHBA-001 (e.g., Form 4), as described herein.

As will be appreciated by one of skill in the art, features and preferred embodiments of one aspect of the invention will also pertain to other aspect of the invention.

DETAILED DESCRIPTION OF THE INVENTION

Crystalline Forms of BHBA-001

Crystalline BHBA-001, including particular crystalline forms (e.g., polymorphs) of BHBA-001 (e.g., Forms 1, 2, 3, and 4, as described herein) may have advantageous properties, for example with regard to stability and/or solubility and/or bioavailability and/or impurity profile and/or filtration characteristics and/or drying characteristics and/or hygroscopicity, and/or ease of handling and/or their ease of micronisation and/or ease of formulation into tablets and/or capsules.

Thus, one aspect of the invention pertains to a crystalline form of 4-(5-(4,7-dimethylbenzofuran-2-yl)-1,2,4-oxadiazol-3-yl)benzoic acid (shown below, and referred to herein as "BHBA-001").

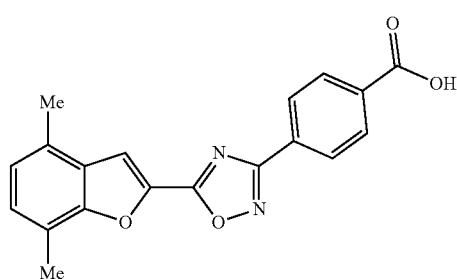 [SMILES: Cc1ccc(C)c2oc(-c3nc(-c4ccc(C(=O)O)cc4)no3)cc12]

In one embodiment, the crystalline form of BHBA-001 is Form 1, as described herein.

In one embodiment, the crystalline form of BHBA-001 is Form 2, as described herein.

In one embodiment, the crystalline form of BHBA-001 is Form 3, as described herein.

In one embodiment, the crystalline form of BHBA-001 is Form 4, as described herein.

The various crystalline forms of BHBA-001 can be identified by their unique solid state signatures with respect to, for example, X-ray powder diffraction (XRPD), differential scanning calorimetry (DSC), and other solid state methods. Further characterisation with respect to water content or solvent content of the crystalline forms can be gauged by any of various routine methods, such as thermogravimetric analysis (TGA), differential scanning calorimetry (DSC), dynamic vapour sorption (DSV), and other techniques.

Notably, crystalline Form 4 of BHBA-001 has (substantially) better physical chemical properties (e.g., anhydrous, low solvent retention, low hygroscopicity, long term stability, suitable particle size, etc.) than the other forms.

Crystalline Form 1

One aspect of the invention pertains to crystalline Form 1 of BHBA-001.

Figure 1:
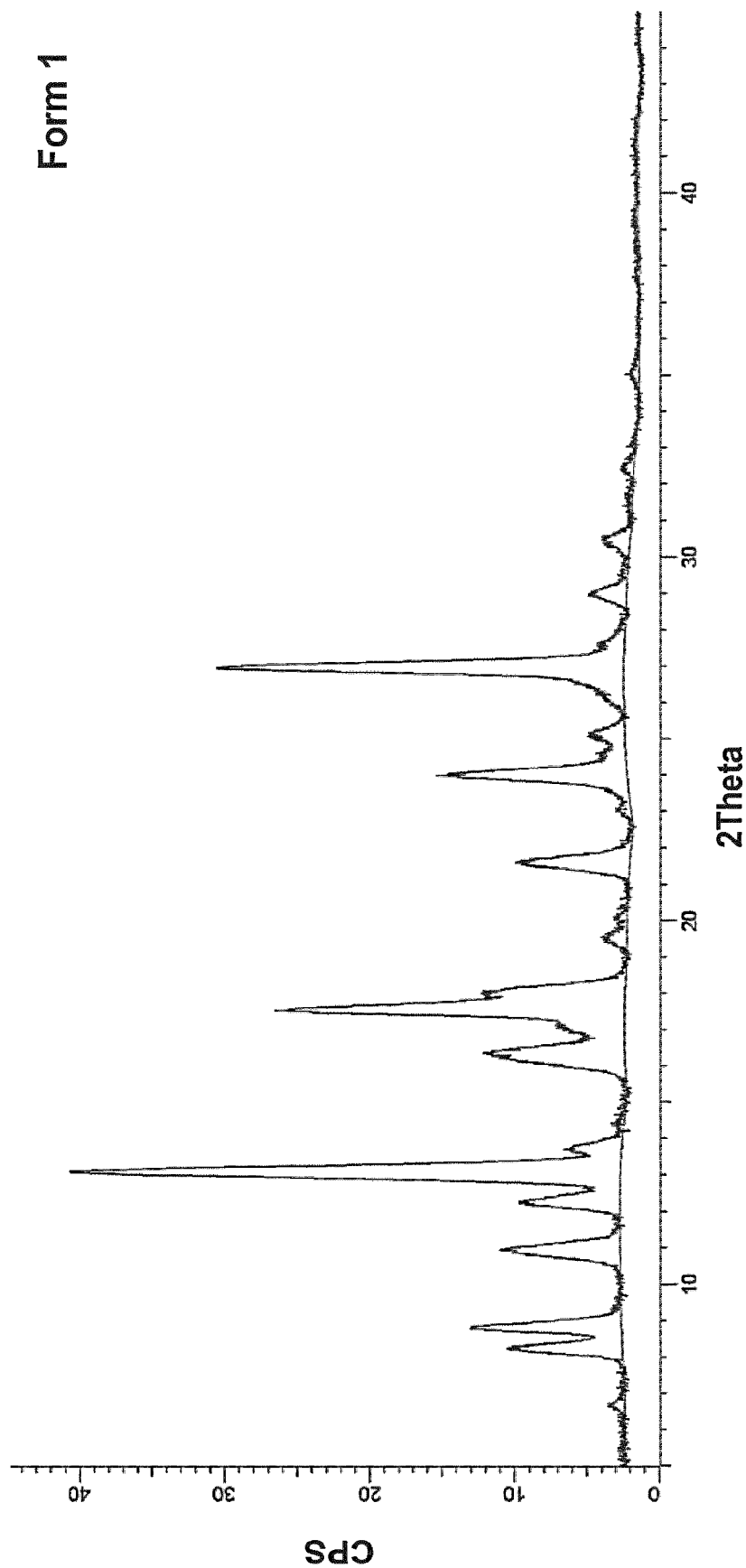
FIG. 1 shows an X-ray powder diffraction (XRPD) pattern for a sample containing crystalline Form 1 of BHBA-001.

FIG. 1 shows an X-ray powder diffraction (XRPD) pattern for a sample containing crystalline Form 1 of BHBA-001.

Figure 2:
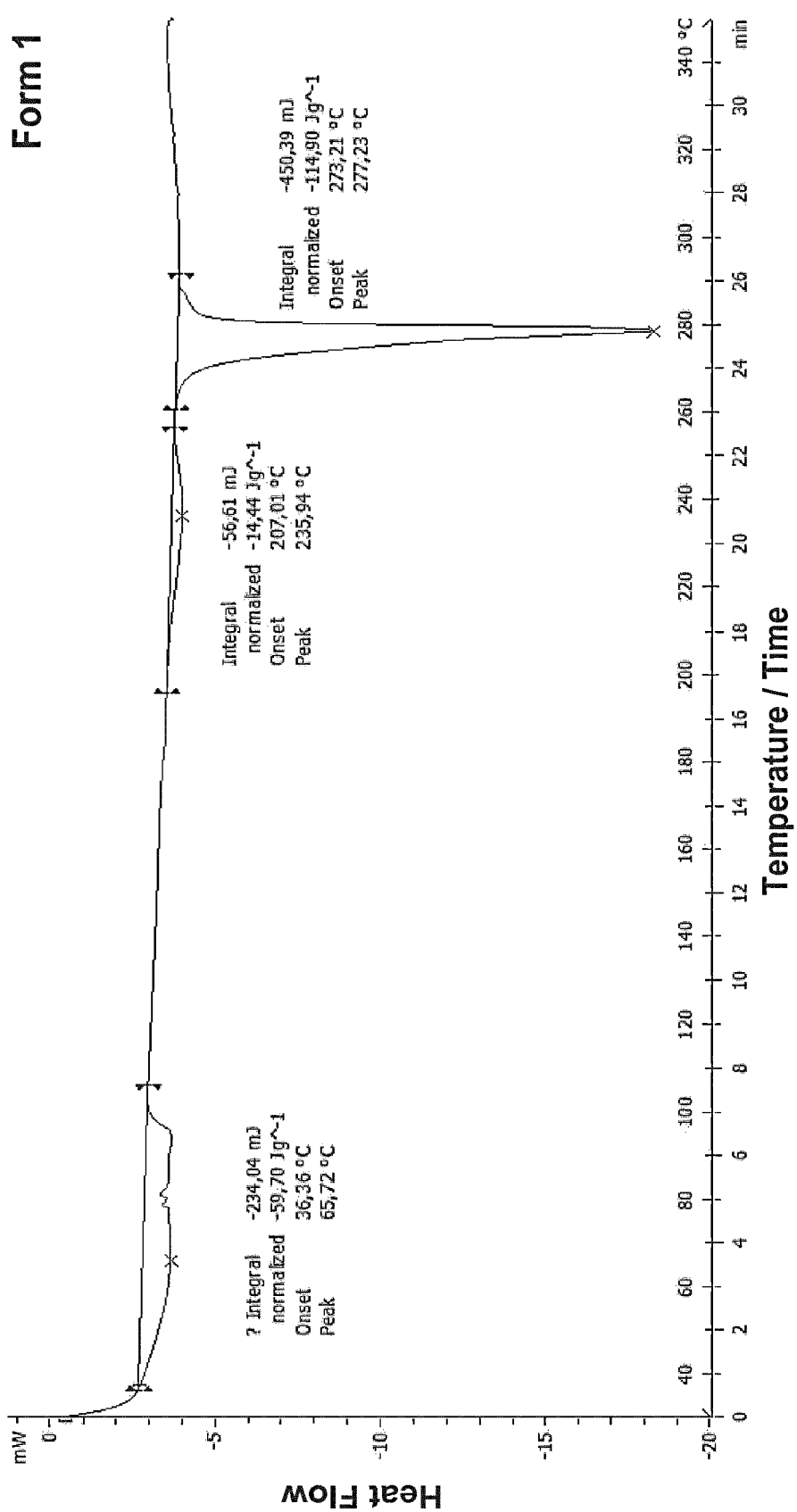
FIG. 2 shows a differential scanning calorimetry (DSC) thermogram for a sample containing crystalline Form 1 of BHBA-001.

FIG. 2 shows a differential scanning calorimetry (DSC) thermogram for a sample containing crystalline Form 1 of BHBA-001.

Figure 3:
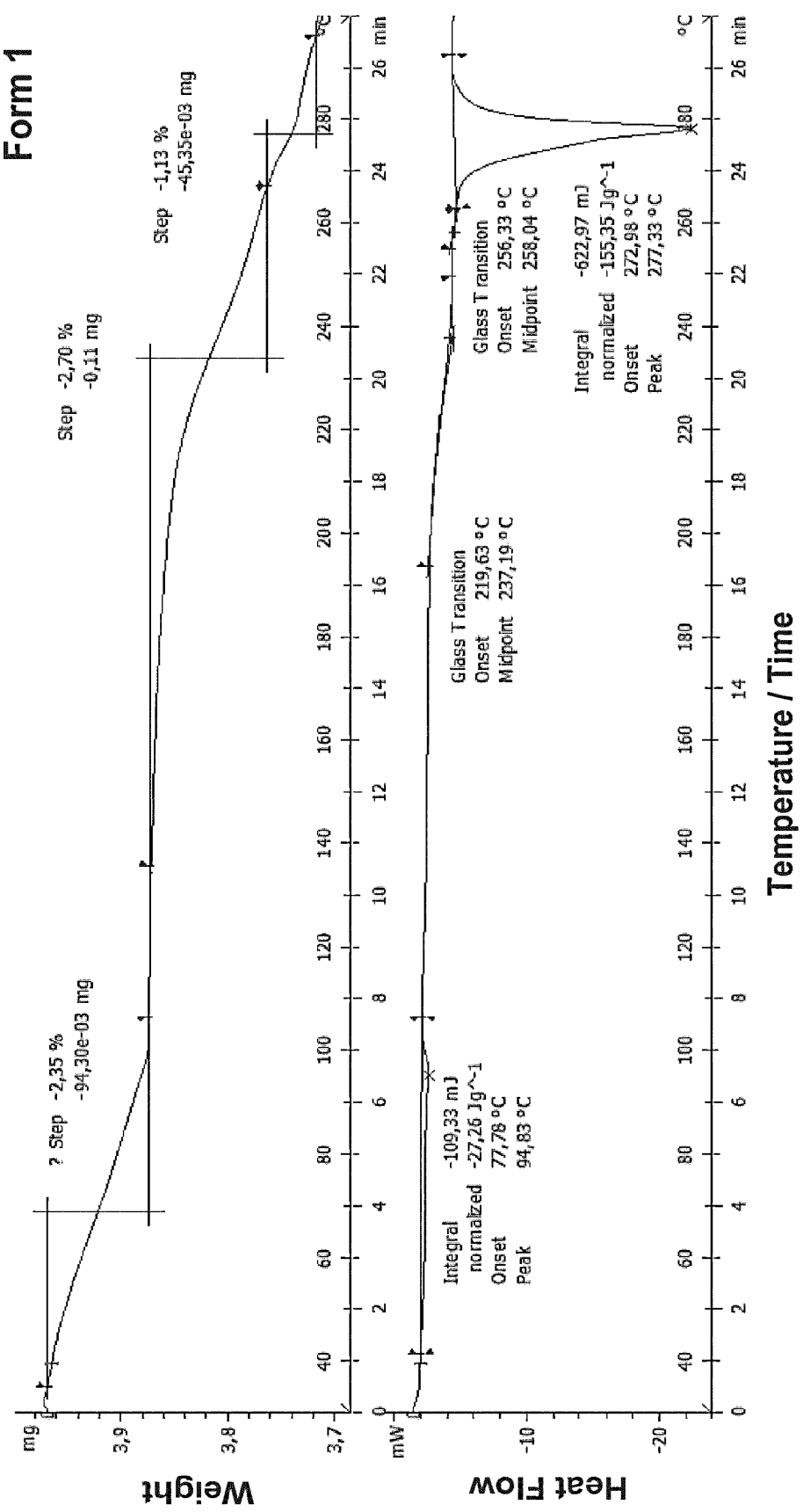
FIG. 3 shows both a thermogravimetric analysis (TGA) thermogram and a differential scanning calorimetry (DSC) thermogram for a sample containing crystalline Form 1 of BHBA-001.

FIG. 3 shows both a thermogravimetric analysis (TGA) thermogram and a differential scanning calorimetry (DSC) thermogram for a sample containing a crystalline Form 1 of BHBA-001.

Figure 4:
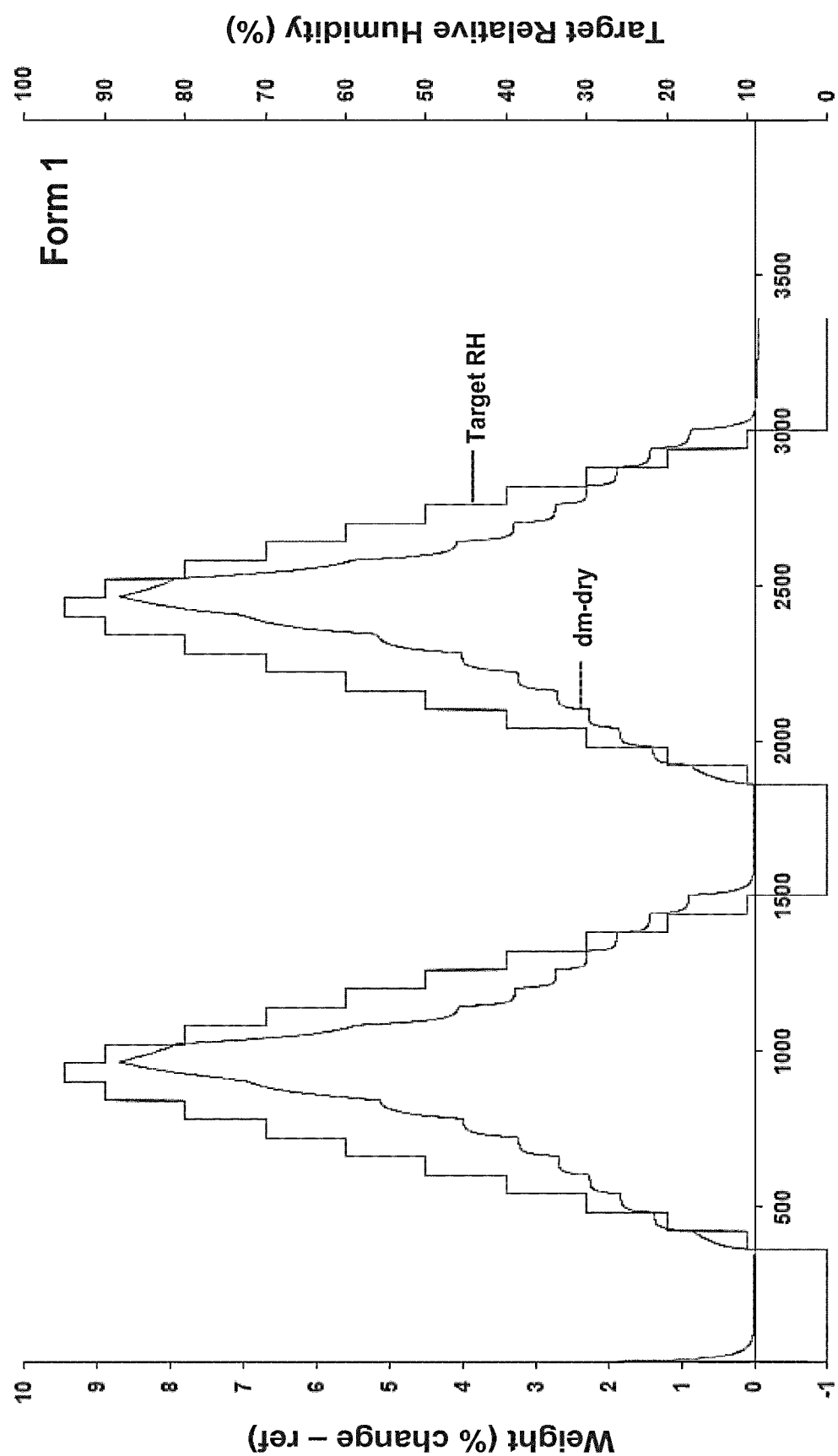
FIG. 4 shows a dynamic vapour sorption (DVS) sorption-desorption plot for a sample containing crystalline Form 1 of BHBA-001.

FIG. 4 shows a dynamic vapour sorption (DVS) sorption-desorption plot for a sample containing crystalline Form 1 of BHBA-001.

Figure 5:
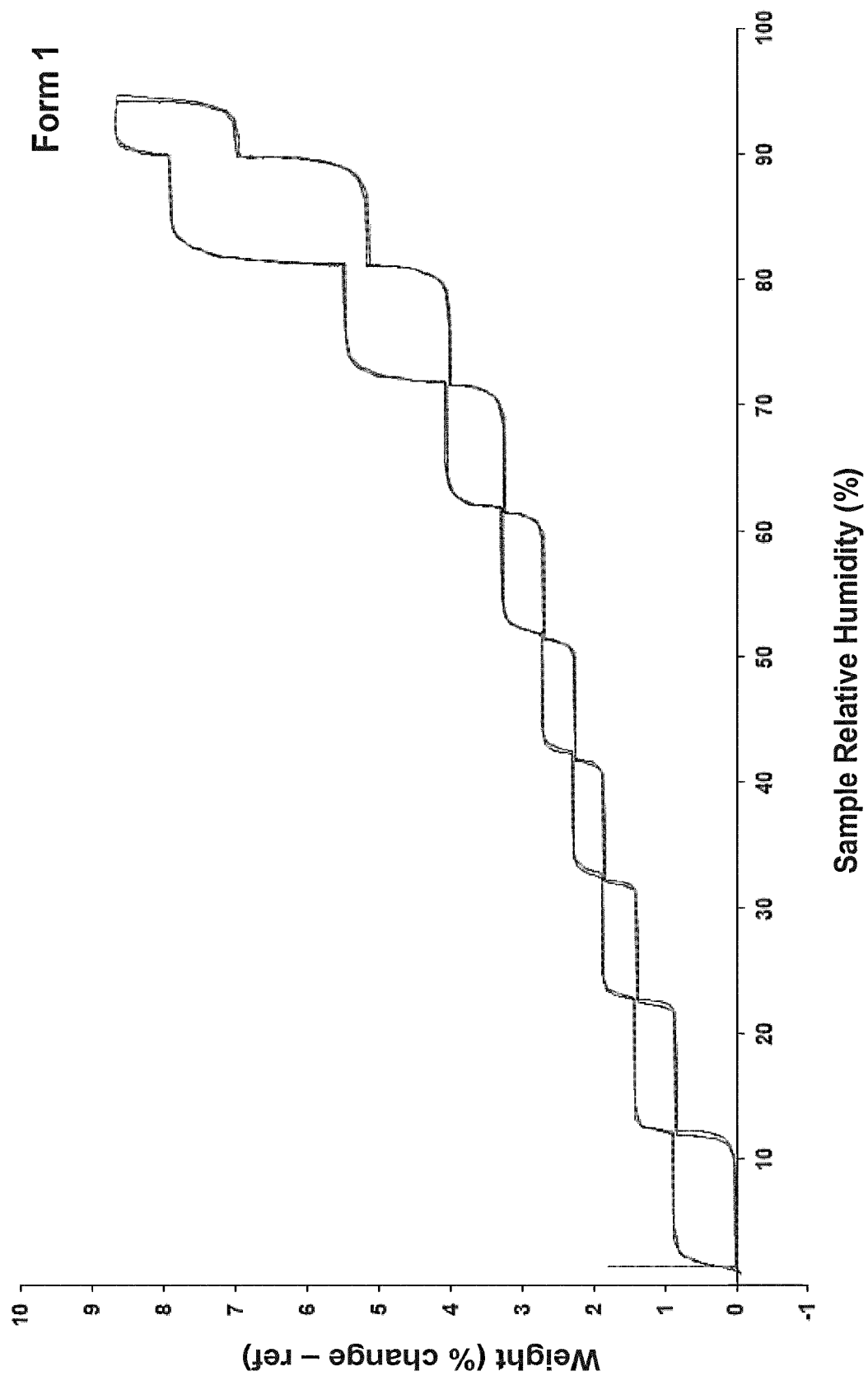
FIG. 5 shows a dynamic vapour sorption (DVS) mass uptake plot for a sample containing crystalline Form 1 of BHBA-001.

FIG. 5 shows a dynamic vapour sorption (DVS) mass uptake plot for a sample containing crystalline Form 1 of BHBA-001.

Figure 6:
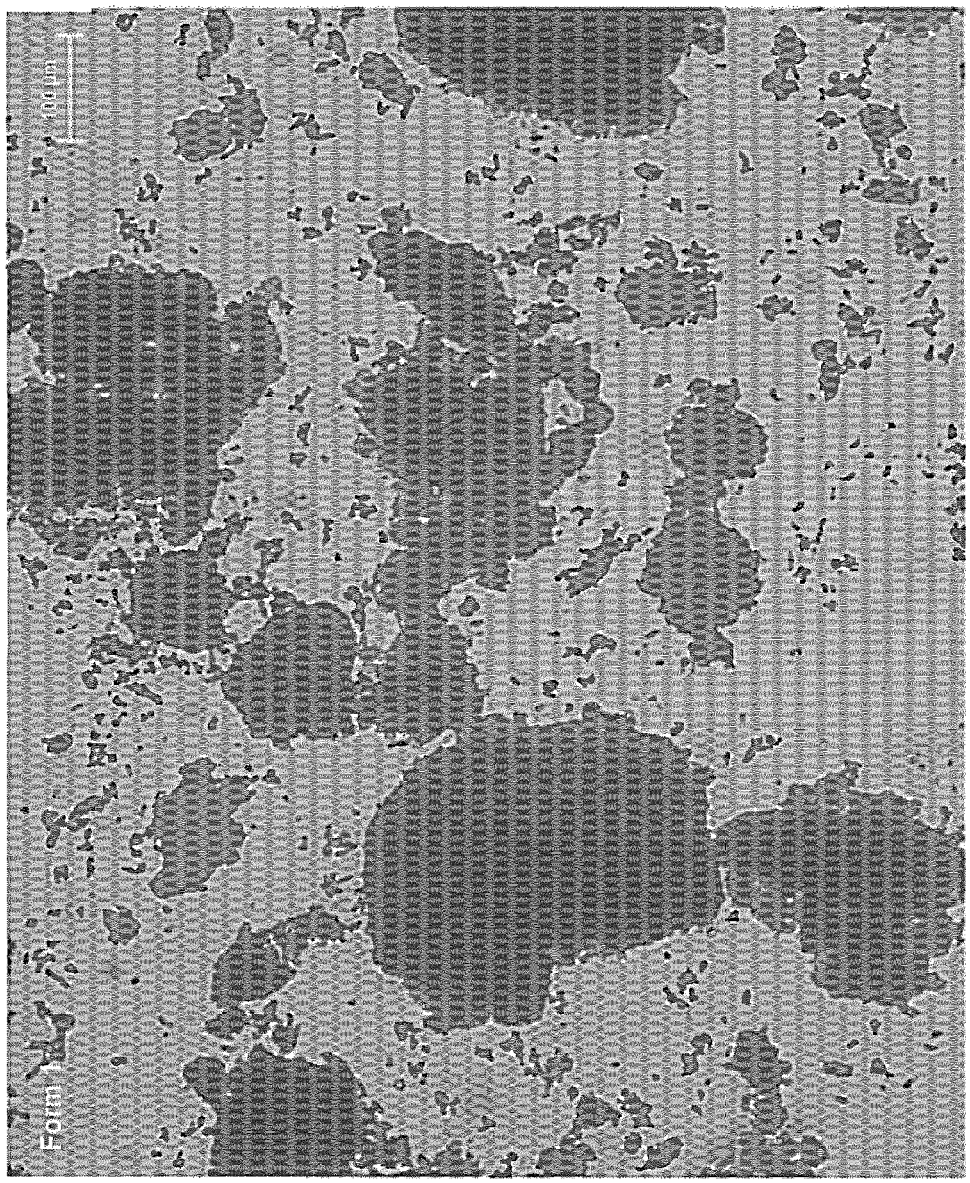
FIG. 6 shows a polarized light microscopy (PLM) micrograph for sample containing crystalline Form 1 of BHBA-001.

FIG. 6 shows a polarized light microscopy (PLM) micrograph for sample containing crystalline Form 1 of BHBA-001.

The physical properties of crystalline Form 1 of BHBA-001 are summarised in the following table.

TABLE 1

Physical Data for Crystalline Form 1 of BHBA-001

| Method | FIG. | Summary |
|---|---|---|
| XRPD | 1 | Peaks of about 10% relative intensity or greater, at 2θ values of about 13.1°, 27.0°, 17.5°, 24.0°, 8.8°, 18.0°, 16.3°, 10.9°, 8.2°, 21.6°, 12.2°, 16.6°, 17.2°, and 13.7° |
| DSC | 2 | Events at $T_{peak}$ about 65.7° C. (−59.7 J/g); $T_{peak}$ about 235.9° C. (−14.4 J/g); and $T_{peak}$ about 277.2° C. (−114.9 J/g) |
| TGA | 3 | Decrease in weight of about 2.4% (approximately 78° C.) and about 1.1% (approximately 273° C.) |
| DVS | 4, 5 | Mass uptake of about 8.7% between 0% and 95% RH |
| Microscopy | 6 | Aggregated particles, ~1 μm |

In one embodiment, the crystalline Form 1 of BHBA-001 has an X-ray powder diffraction which exhibits characteristic scattering angles (2θ) at least at: 13.10±0.2°.

In one embodiment, the crystalline Form 1 of BHBA-001 has an X-ray powder diffraction which exhibits characteristic scattering angles (2θ) at least at: 13.1°±0.2°, 27.0°±0.2°, and 17.5°±0.2°.

In one embodiment, the crystalline Form 1 of BHBA-001 has an X-ray powder diffraction which exhibits characteristic scattering angles (2θ) at least at: 13.1°±0.2°, 27.0°±0.2°, 17.5°±0.2°, and 24.0°±0.2°.

In one embodiment, the crystalline Form 1 of BHBA-001 has an X-ray powder diffraction which exhibits characteristic scattering angles (2θ) at least at: 13.1°±0.2°, 27.0°±0.2°, 17.5°±0.2°, 24.0°±0.2°, 8.8°±0.2°, 18.0°±0.2°, and 16.30±0.2°.

In one embodiment, the crystalline Form 1 of BHBA-001 has an X-ray powder diffraction which exhibits characteristic scattering angles (2θ) at least at: 13.1°±0.2°, 27.0°±0.2°, 17.5°±0.2°, 24.0°±0.2°, 8.8°±0.20, 18.0°±0.2°, 16.3°±0.2°, 10.9°±0.2°, 8.2°±0.2°, and 21.6°±0.2°.

In one embodiment, the crystalline Form 1 of BHBA-001 has an X-ray powder diffraction which exhibits characteristic scattering angles (2θ) at least at: 13.1°±0.2°, 27.0°±0.2°, 17.5°±0.2°, 24.0°±0.2°, 8.8°±0.2°, 18.0°±0.2°, 16.3°±0.2°, 10.9°±0.2°, 8.2°±0.2°, 21.6°±0.2°, 12.2°±0.2°, 16.6°±0.2°, and 17.2°±0.2°.

In one embodiment, the crystalline Form 1 of BHBA-001 has an X-ray powder diffraction substantially as shown in FIG. 1.

In one embodiment, the crystalline Form 1 of BHBA-001 has a differential scanning calorimetry thermogram comprising an endotherm at 277±4° C.

In one embodiment, the crystalline Form 1 of BHBA-001 has a differential scanning calorimetry thermogram substantially as shown in FIG. 2.

In one embodiment, the crystalline Form 1 of BHBA-001 has a thermogravimetric analysis thermogram showing a weight loss of about 2.4±2% between 40±4° C. and 100±4° C.

In one embodiment, the crystalline Form 1 of BHBA-001 has a thermogravimetric analysis thermogram showing a weight loss of about 2.7±2% with an onset temperature at 219±4° C.

In one embodiment, the crystalline Form 1 of BHBA-001 has a thermogravimetric analysis thermogram showing a weight loss of about 1.1±2% with an onset temperature at 256±4° C.

In one embodiment, the crystalline Form 1 of BHBA-001 has a thermogravimetric analysis thermogram substantially as shown in FIG. 3.

In one embodiment, the crystalline Form 1 of BHBA-001 has a dynamic vapour sorption sorption-desorption profile substantially as shown in FIG. 4.

In one embodiment, the crystalline Form 1 of BHBA-001 has a dynamic vapour sorption mass uptake profile substantially as shown in FIG. 5.

Crystalline Form 2

One aspect of the invention pertains to crystalline Form 2 of BHBA-001.

Figure 7:
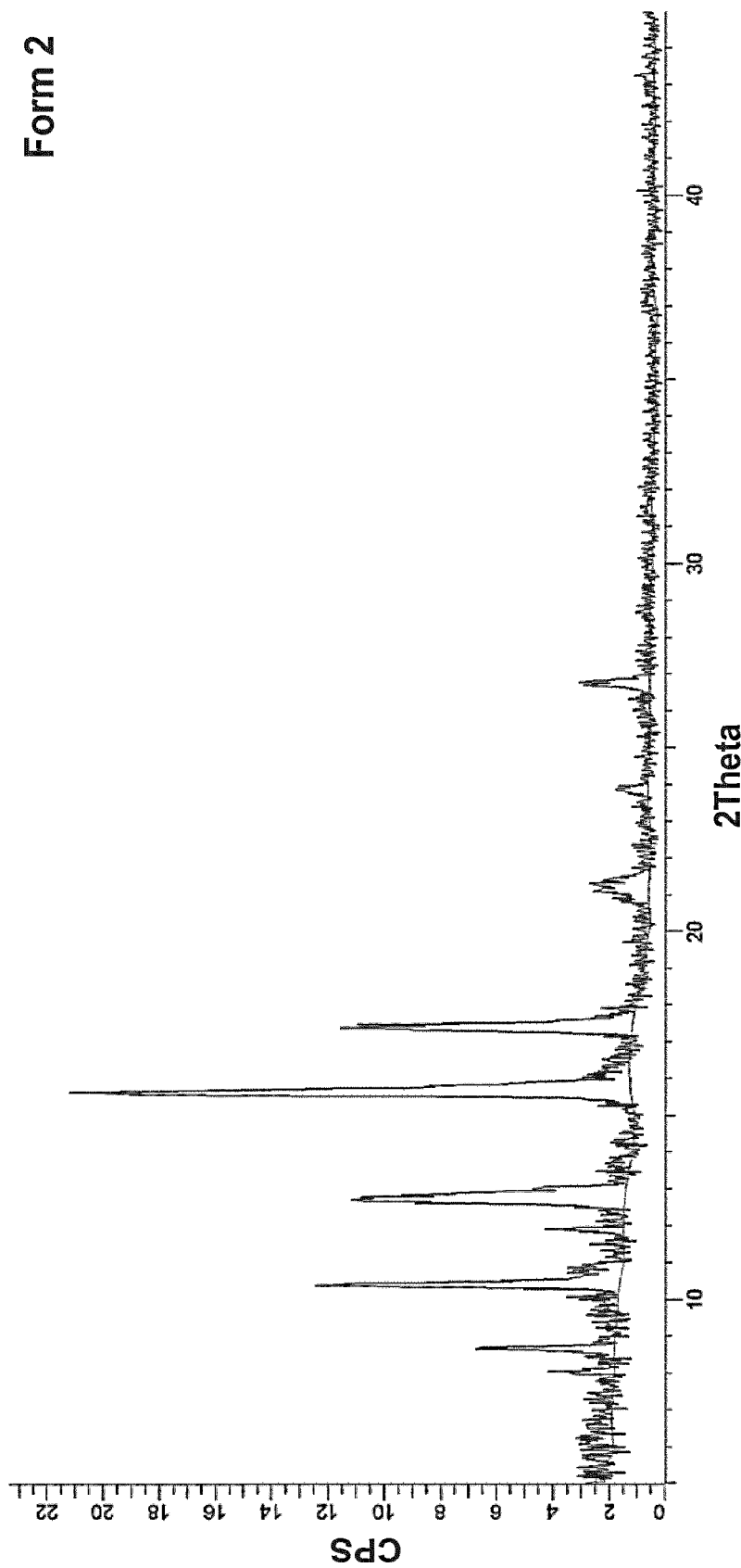
FIG. 7 shows an X-ray powder diffraction (XRPD) pattern for a sample containing crystalline Form 2 of BHBA-001.

FIG. 7 shows an X-ray powder diffraction (XRPD) pattern for a sample containing crystalline Form 2 of BHBA-001.

In one embodiment, the crystalline Form 2 of BHBA-001 has an X-ray powder diffraction which exhibits characteristic scattering angles (2θ) at least at: 15.6°±0.2°.

In one embodiment, the crystalline Form 2 of BHBA-001 has an X-ray powder diffraction which exhibits characteristic scattering angles (2θ) at least at: 15.6°±0.2°, 10.4°±0.2°, 12.7°±0.2°, and 17.4°±0.2°.

In one embodiment, the crystalline Form 2 of BHBA-001 has an X-ray powder diffraction which exhibits characteristic scattering angles (2θ) at least at: 15.6°±0.2°, 10.4°±0.2°, 12.7°±0.2°, 17.4°±0.2°, and 8.7°±0.2°.

In one embodiment, the crystalline Form 2 of BHBA-001 has an X-ray powder diffraction which exhibits characteristic scattering angles (2θ) at least at: 15.6°±0.2°, 10.4°±0.2°, 12.7°±0.2°, 17.4°±0.2°, 8.7°±0.2°, 11.9°±0.2°, 21.3°±0.2°, and 26.7°±0.2°.

In one embodiment, the crystalline Form 2 of BHBA-001 has an X-ray powder diffraction substantially as shown in FIG. 7.

Crystalline Form 3

One aspect of the invention pertains to crystalline Form 3 of BHBA-001.

Figure 8:
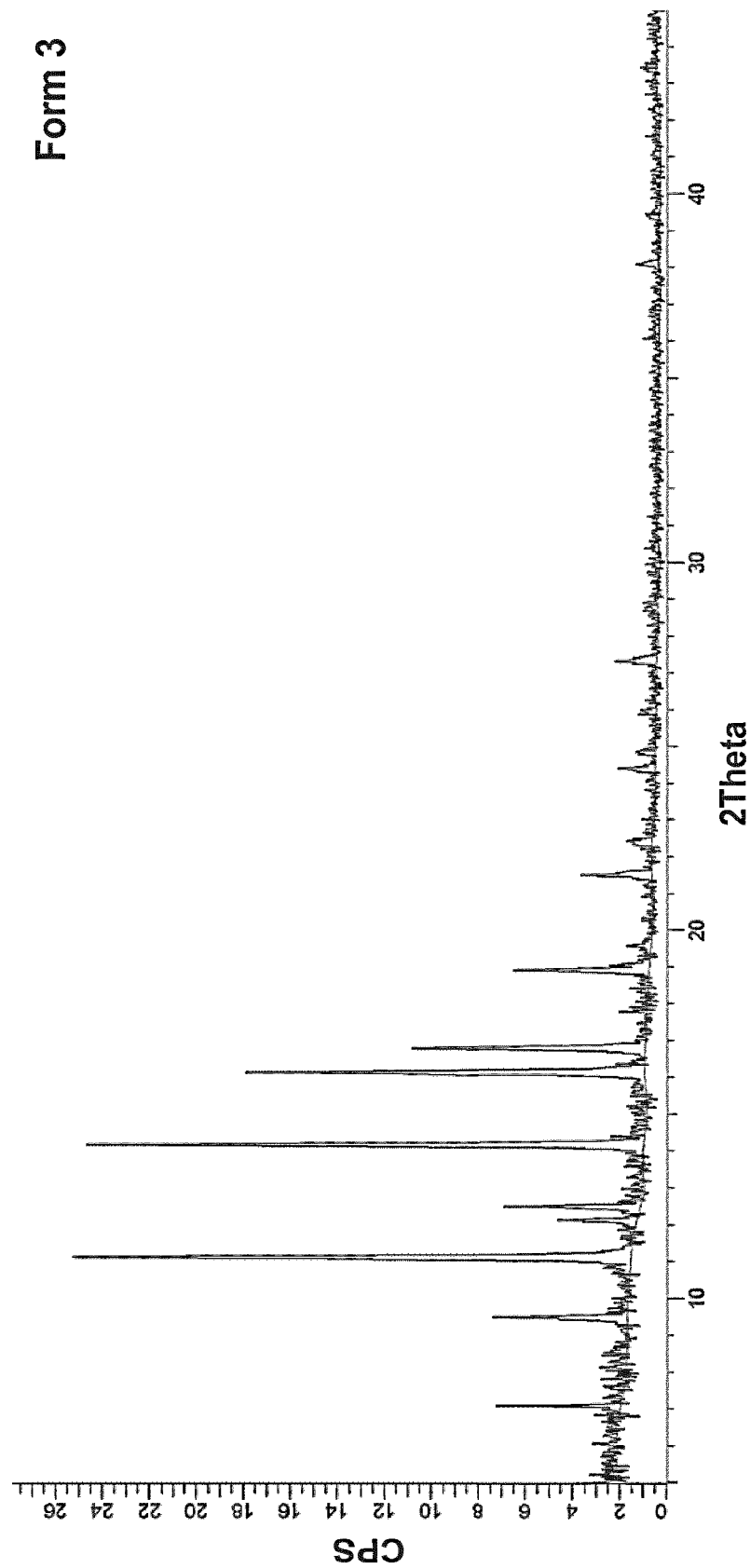
FIG. 8 shows an X-ray powder diffraction (XRPD) pattern for a sample containing crystalline Form 3 of BHBA-001.

FIG. 8 shows an X-ray powder diffraction (XRPD) pattern for a sample containing crystalline Form 3 of BHBA-001.

In one embodiment, the crystalline Form 3 of BHBA-001 has an X-ray powder diffraction which exhibits characteristic scattering angles (2θ) at least at: 14.2°±0.2°.

In one embodiment, the crystalline Form 3 of BHBA-001 has an X-ray powder diffraction which exhibits characteristic scattering angles (2θ) at least at: 14.2°±0.2° and 11.1°±0.2°.

In one embodiment, the crystalline Form 3 of BHBA-001 has an X-ray powder diffraction which exhibits characteristic scattering angles (2θ) at least at: 14.2°±0.2°, 11.1°±0.2°, and 16.1°±0.2°.

In one embodiment, the crystalline Form 3 of BHBA-001 has an X-ray powder diffraction which exhibits characteristic scattering angles (2θ) at least at: 14.2°±0.2°, 11.1°±0.2°, 16.1°±0.2°, and 16.8°±0.2°.

In one embodiment, the crystalline Form 3 of BHBA-001 has an X-ray powder diffraction which exhibits characteristic scattering angles (2θ) at least at: 14.2°±0.2°, 11.1°±0.2°, 16.1°±0.2°, 16.8°±0.2°, 9.5°±0.2°, 18.9°±0.2°, and 7.1°±0.2°.

In one embodiment, the crystalline Form 3 of BHBA-001 has an X-ray powder diffraction which exhibits characteristic scattering angles (2θ) at least at: 14.2°±0.2°, 11.1°±0.2°, 16.1°±0.2°, 16.8°±0.2°, 9.5°±0.2°, 18.9°±0.2°, 7.1°±0.2°, 12.4°±0.2°, 21.5°±0.2°, and 12.1°±0.20.

In one embodiment, the crystalline Form 3 of BHBA-001 has an X-ray powder diffraction substantially as shown in FIG. 8.

Crystalline Form 4

One aspect of the invention pertains to crystalline Form 4 of BHBA-001.

Figure 9:
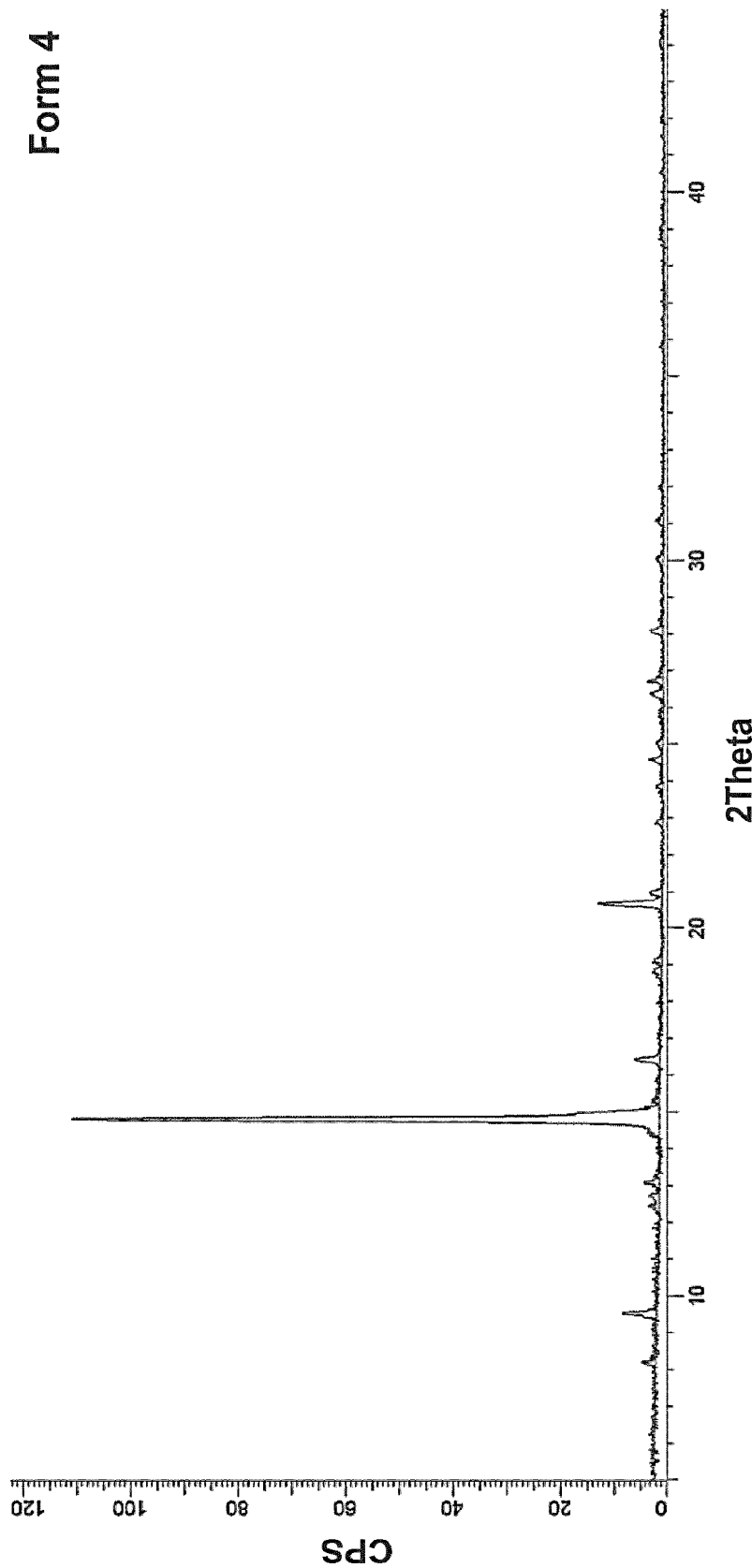
FIG. 9 shows an X-ray powder diffraction (XRPD) pattern for a sample containing crystalline Form 4 of BHBA-001.

FIG. 9 shows an X-ray powder diffraction (XRPD) pattern for a sample containing crystalline Form 4 of BHBA-001.

Figure 10:
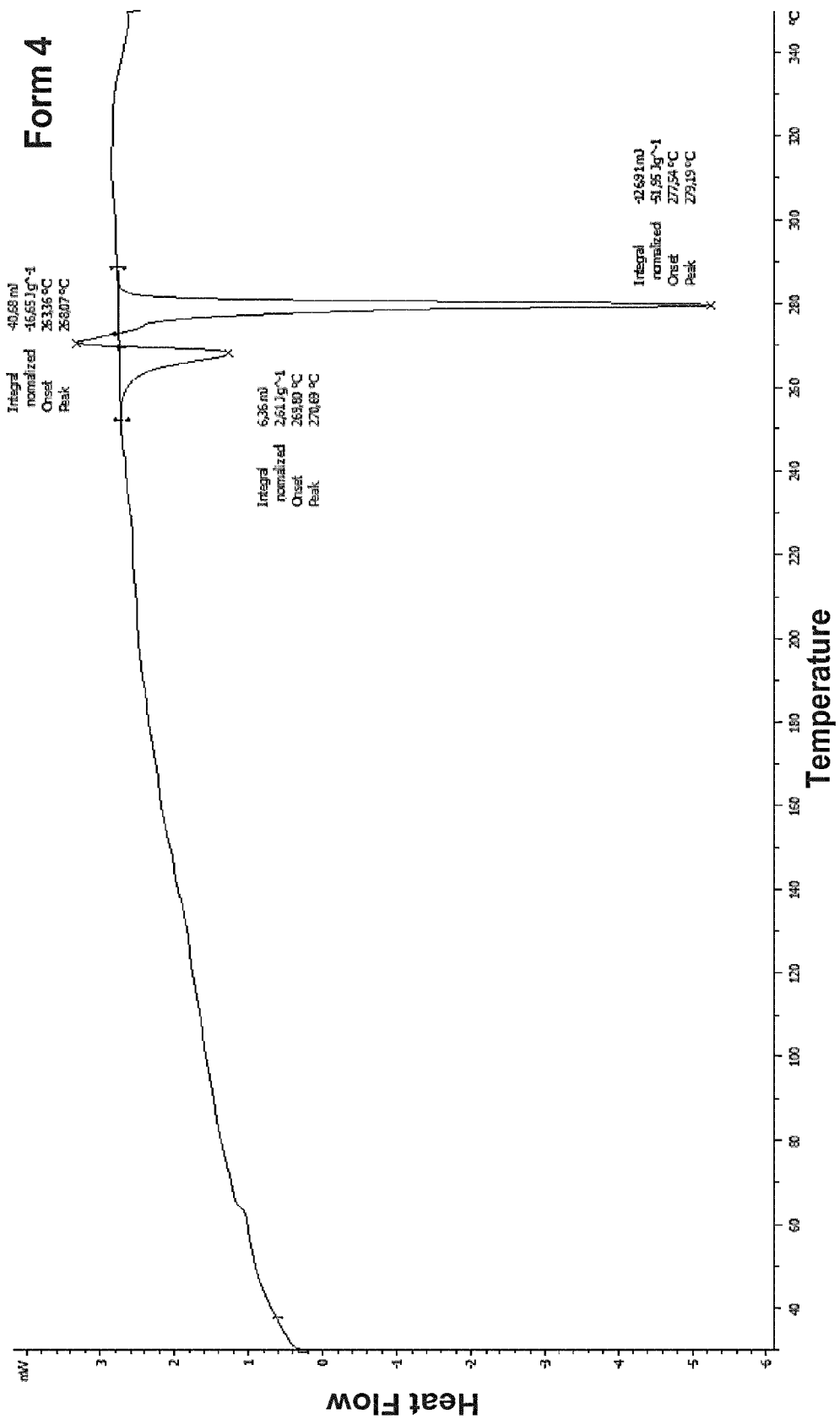
FIG. 10 shows a differential scanning calorimetry (DSC) thermogram for a sample containing crystalline Form 4 of BHBA-001.

FIG. 10 shows a differential scanning calorimetry (DSC) thermogram for a sample containing crystalline Form 4 of BHBA-001.

Figure 11:
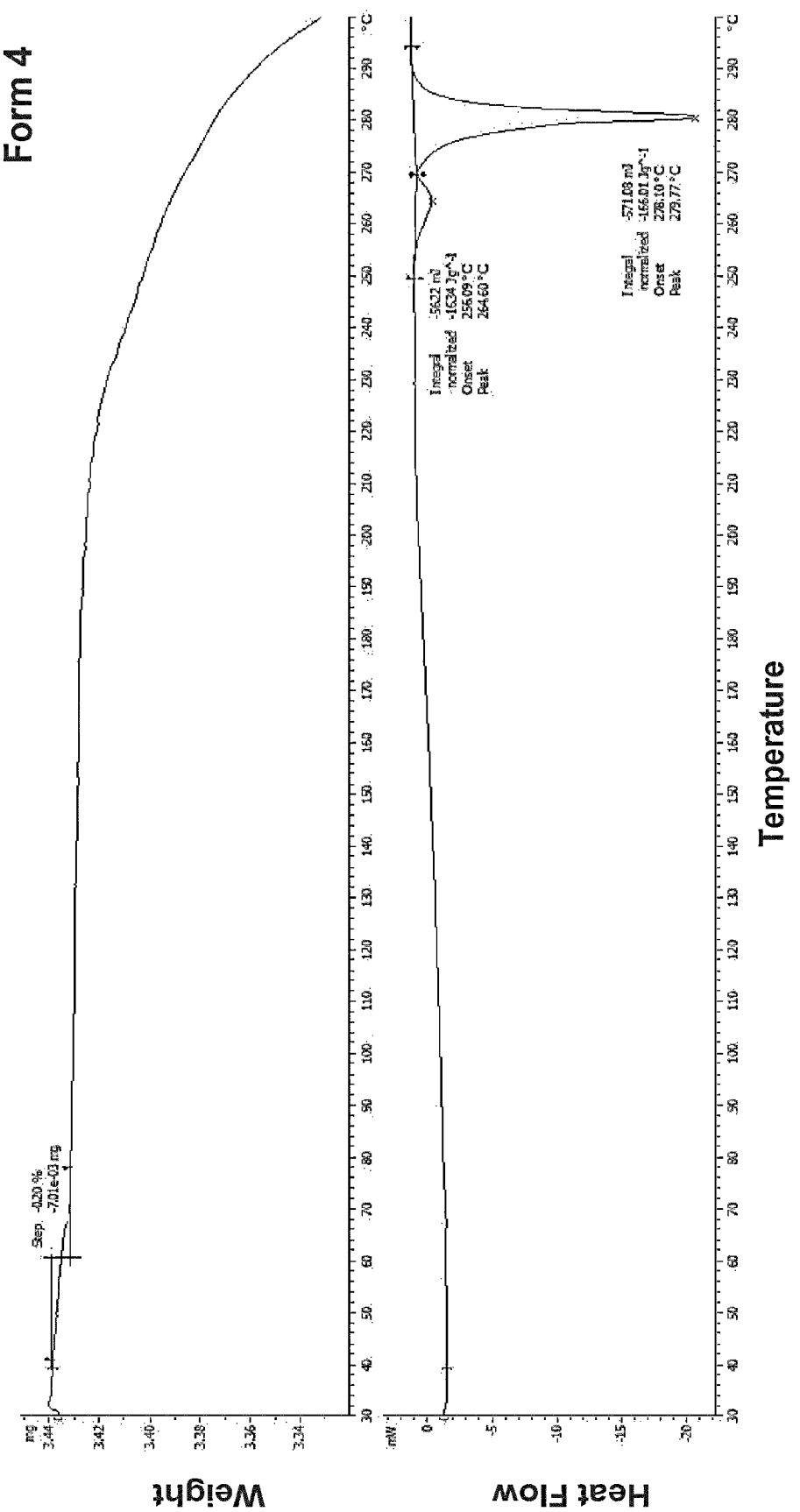
FIG. 11 shows both a thermogravimetric analysis (TGA) thermogram and a differential scanning calorimetry (DSC) thermogram for a sample containing a crystalline Form 4 of BHBA-001.

FIG. 11 shows both a thermogravimetric analysis (TGA) thermogram and a differential scanning calorimetry (DSC) thermogram for a sample containing a crystalline Form 4 of BHBA-001.

Figure 12:
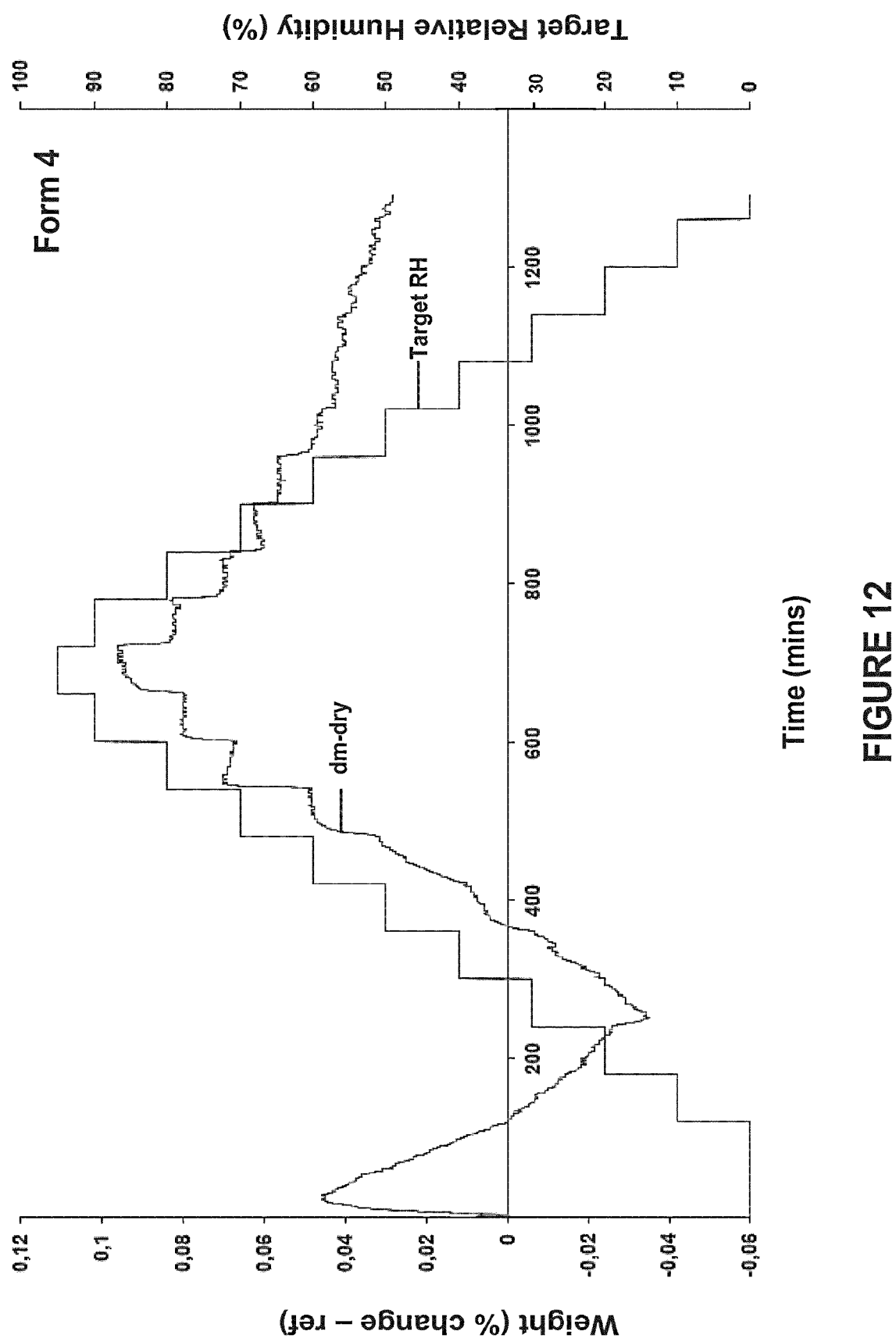
FIG. 12 shows a dynamic vapour sorption (DVS) sorption-desorption plot for a sample containing crystalline Form 4 of BHBA-001.

FIG. 12 shows a dynamic vapour sorption (DVS) sorption-desorption plot for a sample containing crystalline Form 4 of BHBA-001.

Figure 13:
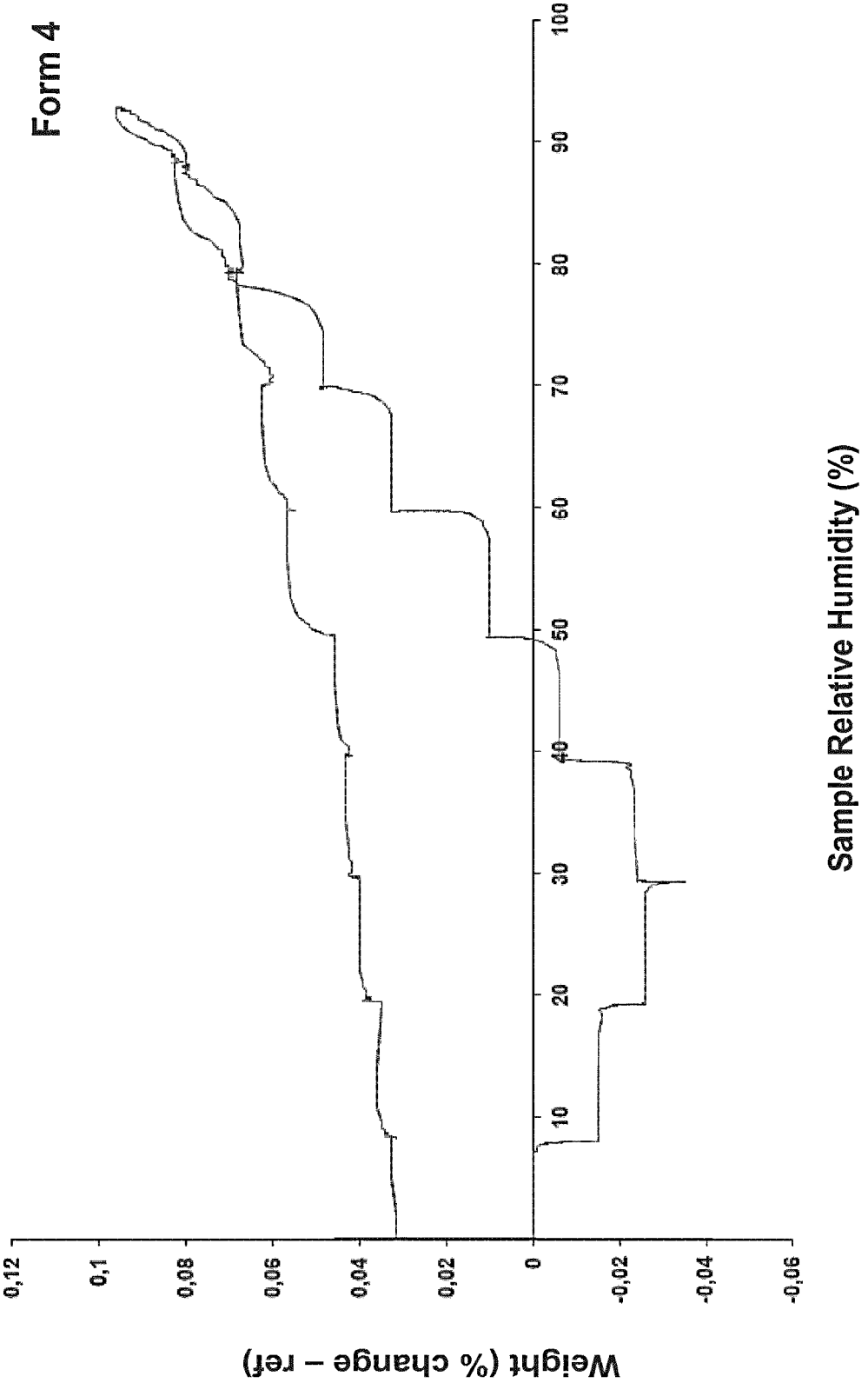
FIG. 13 shows a dynamic vapour sorption (DVS) mass uptake plot for a sample containing crystalline Form 4 of BHBA-001.

FIG. 13 shows a dynamic vapour sorption (DVS) mass uptake plot for a sample containing crystalline Form 4 of BHBA-001.

Figure 14:
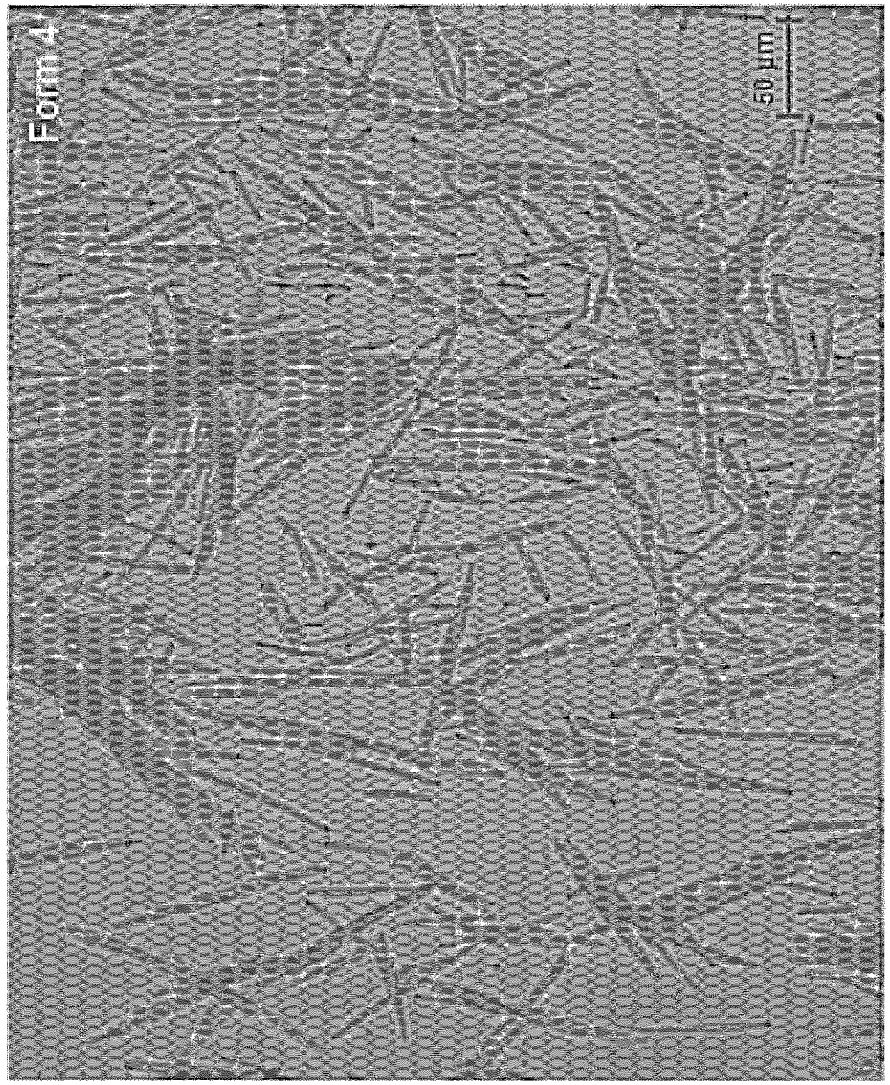
FIG. 14 shows a polarized light microscopy (PLM) micrograph for sample containing crystalline Form 4 of BHBA-001.

FIG. 14 shows a polarized light microscopy (PLM) micrograph for sample containing crystalline Form 4 of BHBA-001.

The physical properties of crystalline Form 4 of BHBA-001 are summarised in the following table.

TABLE 2

Physical Data for Crystalline Form 4 of BHBA-001

| Method | FIG. | Summary |
| --- | --- | --- |
| XRPD | 10 | Peaks of about 10% relative intensity or greater, at 2θ values of about 14.8° and 20.7°; additional peaks of about 2% relative intensity or greater, at 2θ values of about 9.5°, 16.4°, 13.1°, 24.6°, 26.7°, 21.0°, 14.4°, 12.4°, 12.7°, and 28.1° |
| DSC | 11 | Events at $T_{peak}$ about 268.1° C. (−16.6 J/g); $T_{peak}$ about 270.7° C. (2.6 J/g), and $T_{peak}$ about 279.2° C. (−52.0 J/g) |
| TGA | 12 | Decrease in weight of about 0.2% (40-80° C.) |
| DVS | 13 | Mass uptake of about 0.1% between 0% and 95% RH |
| Microscopy | 14 | Acicular particles, ~50-100 μm |

In one embodiment, the crystalline Form 4 of BHBA-001 has an X-ray powder diffraction which exhibits characteristic scattering angles (2θ) at least at: 14.8°±0.2°.

In one embodiment, the crystalline Form 4 of BHBA-001 has an X-ray powder diffraction which exhibits characteristic scattering angles (2θ) at least at: 14.8°±0.2°, and 20.7°±0.2°.

In one embodiment, the crystalline Form 4 of BHBA-001 has an X-ray powder diffraction which exhibits characteristic scattering angles (2θ) at least at: 14.8°±0.2°, 20.7°±0.2°, and 9.5°±0.2°.

In one embodiment, the crystalline Form 4 of BHBA-001 has an X-ray powder diffraction which exhibits characteristic scattering angles (2θ) at least at: 14.8°±0.2°, 20.7°±0.2°, 9.5°±0.2°, and 16.4°±0.2°.

In one embodiment, the crystalline Form 4 of BHBA-001 has an X-ray powder diffraction which exhibits characteristic scattering angles (2θ) at least at: 14.8°±0.2°, 20.7°±0.2°, 9.50±0.2°, 16.4°±0.2°, 13.1°±0.2°, 24.6°±0.2°, 26.7°±0.2°, and 21.0°±0.2°.

In one embodiment, the crystalline Form 4 of BHBA-001 has an X-ray powder diffraction which exhibits characteristic scattering angles (2θ) at least at: 14.8°±0.2°, 20.7°±0.2°, 9.5°±0.2°, 16.4°±0.2°, 13.1°±0.2°, 24.6°±0.2°, 26.7°±0.2°, 21.0°±0.2°, 14.4°±0.2°, 12.4°±0.2°, 12.7°±0.2°, and 28.1°±0.2°.

In one embodiment, the crystalline Form 4 of BHBA-001 has an X-ray powder diffraction which does not exhibit characteristic scattering angles (2θ) (for example, where peak intensity is less that about 3% of the most intense peak) between 17.0°±0.2° and 20.0°±0.2°.

Figure 15:
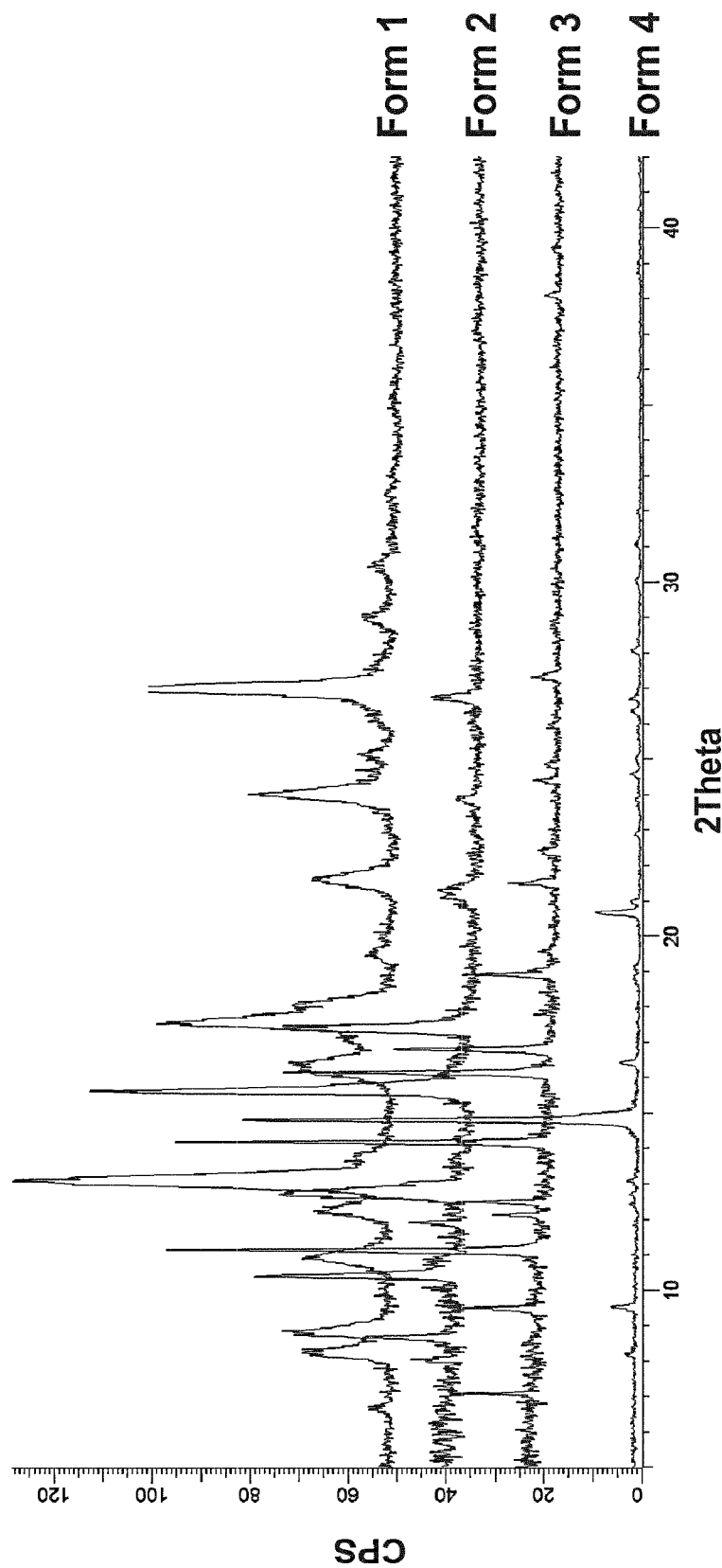
FIG. 15 shows an overlay of X-ray powder diffraction (XRPD) patterns for samples containing crystalline Forms 1, 2, 3, and 4 of BHBA-001.

As shown in the following table, each of Forms 1, 2, and 3 have large peaks in the range 16.8° to 20.2°. In contrast, Form 4 has no peak in that range with an intensity of 3% or greater. See also, e.g., FIG. 15.

TABLE 3

XRPD Characteristic Scattering Angles
for Form 1, 2, 3, and 4
In the Range 16.8° to 20.2°

| Crystalline Form | Scattering Angle (2θ) | Relative Intensity |
| --- | --- | --- |
| Form 3 | 16.8 | 41.40% |
| Form 1 | 17.2 | 12.20% |
| Form 2 | 17.4 | 50.60% |
| Form 1 | 17.5 | 61.00% |
| Form 1 | 18.0 | 26.00% |
| Form 4 | 18.8 | 1.10% |
| Form 3 | 18.9 | 22.90% |
| Form 4 | 19.1 | 1.20% |
| Form 3 | 19.5 | 3.90% |

In one embodiment, the crystalline Form 4 of BHBA-001 has an X-ray powder diffraction in which any peaks at characteristic scattering angles (2θ) between 17.0°±0.2° and 20.0°±0.2° have a peak intensity of less than about 3% of the most intense peak, preferably less than about 2% of the most intense peak, more preferably less than about 1.5% of the most intense peak.

In one embodiment, the crystalline Form 4 of BHBA-001 has an X-ray powder diffraction which does not exhibit characteristic scattering angles (2θ) (for example, where peak intensity is less that about 3% of the most intense peak) between 10.0°±0.2° and 12.0°±0.2°.

As shown in the following table, each of Forms 1, 2, and 3 have large peaks in the range 9.8° to 12.2°. In contrast, Form 4 has no peak in that range with an intensity of 3.0% or greater. See also, e.g., FIG. 15.

TABLE 4

XRPD Characteristic Scattering Angles
for Form 1, 2, 3, and 4
In the Range 9.8° to 12.2°

| Crystalline Form | Scattering Angle (2θ) | Relative Intensity |
| --- | --- | --- |
| Form 2 | 10.4 | 54.80% |
| Form 4 | 10.4 | 0.90% |
| Form 1 | 10.9 | 21.90% |
| Form 3 | 11.1 | 99.90% |
| Form 2 | 11.9 | 12.20% |
| Form 3 | 12.1 | 10.20% |
| Form 1 | 12.2 | 17.50% |

In one embodiment, the crystalline Form 4 of BHBA-001 has an X-ray powder diffraction in which any peaks at characteristic scattering angles (2θ) between 10.0°±0.2° and 12.0°±0.2° have a peak intensity of less than about 3% of the most intense peak, preferably less than about 2% of the most intense peak, more preferably less than about 1% of the most intense peak.

In one embodiment, the crystalline Form 4 of BHBA-001 has an X-ray powder diffraction substantially as shown in FIG. 9.

In one embodiment, the crystalline Form 4 of BHBA-001 has a differential scanning calorimetry thermogram comprising an endotherm at about 268±4° C.

In one embodiment, the crystalline Form 4 of BHBA-001 has a differential scanning calorimetry thermogram substantially as shown in FIG. 10.

In one embodiment, the crystalline Form 4 of BHBA-001 has a thermogravimetric analysis thermogram showing a weight loss of less than about 0.5% between 40±4° C. and 100±4° C.

In one embodiment, the crystalline Form 4 of BHBA-001 has a thermogravimetric analysis thermogram substantially as shown in FIG. 11.

In one embodiment, the crystalline Form 4 of BHBA-001 has a dynamic vapour sorption sorption-desorption profile substantially as shown in FIG. 12.

In one embodiment, the crystalline Form 4 of BHBA-001 has a dynamic vapour sorption mass uptake profile substantially as shown in FIG. 13.

Comparison of Crystalline Forms

Each of crystalline Forms 1, 2, 3, and 4 have XRPD patterns which exhibit distinct characteristic scattering angles. See, e.g., FIG. 15.

Crystalline Form 1 of BHBA-001 contains 2.4% (w/w) residual solvent, is hygroscopic with 8.7% (w/w) uptake between 0% and 95% relative humidity (RH), and the solid and the solid consists of small(er) particles.

Crystalline Form 2 of BHBA-001 (obtained from ethanol) was found to contain ethanol and was characterised as an ethanol solvate.

Crystalline Form 3 of BHBA-001 (obtained from acetic acid) was found to contain acetic acid and was characterised as an acetic acid solvate.

Crystalline Form 4 of BHBA-001 is anhydrous, contains little or no residual solvent, has low hygroscopicity, is stable for many months at ambient conditions, and the solid consists of large(r) particles.

Above 250° C., Form 4 melts and recrystallizes to give Form 1.

Based on its (substantially) better physical chemical properties (e.g., anhydrous, low solvent retention, low hygroscopicity, long term stability, suitable particle size, etc.), crystalline Form 4 of BHBA-001 is the most suitable for development as a formulation candidate.

Chemical Synthesis of BHBA-001

One synthetic route for the preparation of BHBA-001 is described in Borthwick et al., 2016, and is shown in Scheme 1 below.

Scheme 1

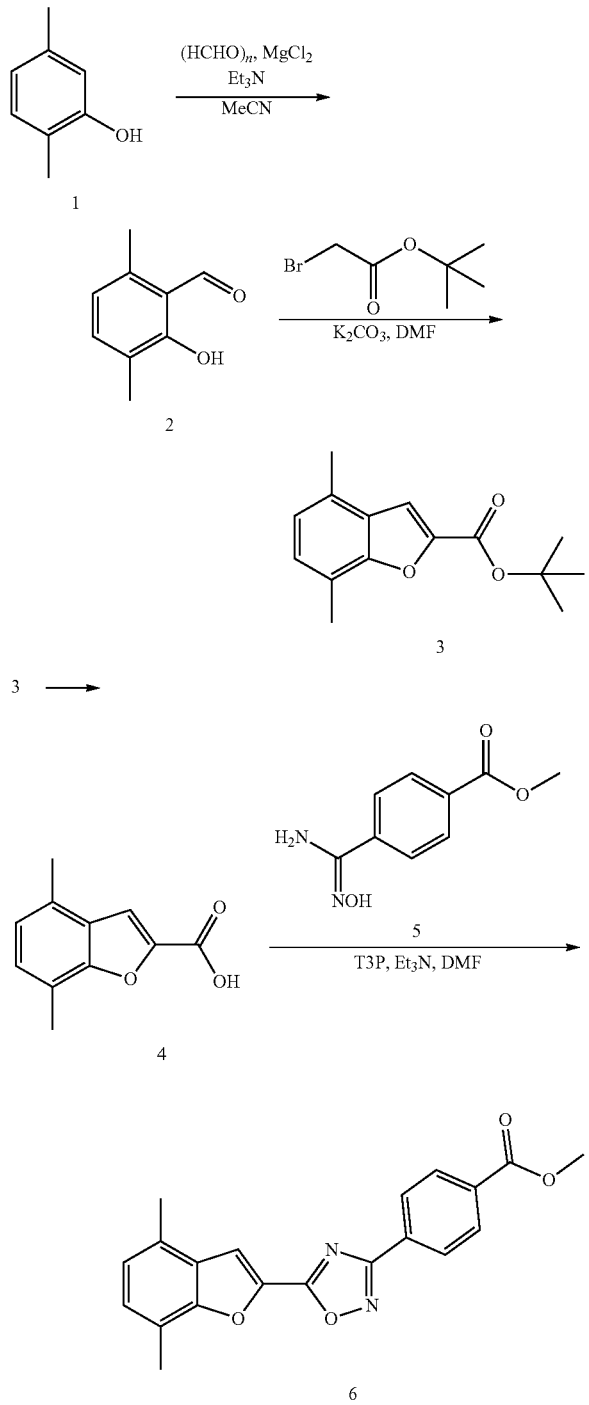

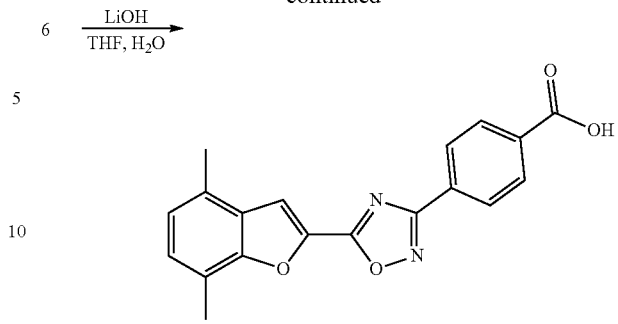

In this approach, 2,5-dimethylphenol (1) is reacted with paraformaldehyde to give 2-hydroxy-3,6-dimethylbenzaldehyde (2), which is then reacted with tert-butyl 2-bromoacetate to give tert-butyl 4,7-dimethylbenzofuran-2-carboxylate (3), and deprotected to give 4,7-dimethylbenzofuran-2-carboxylic acid (4). This acid is then reacted with methyl 4-(N'-hydroxycarbamimidoyl)benzoate (5) to give methyl 4-(5-(4,7-dimethylbenzofuran-2-yl)-1,2,4-oxadiazol-3-yl)benzoate (6), which is then deprotected to give the target compound, 4-(5-(4,7-dimethylbenzofuran-2-yl)-1,2,4-oxadiazol-3-yl)benzoic acid (BHBA-001).

An example of this synthetic route is described below.

Step 1: 2-Hydroxy-3,6-dimethylbenzaldehyde (2)

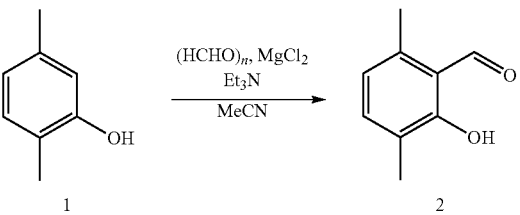

A suspension of 2,5-dimethylphenol (1) (20 g, 160 mmol), paraformaldehyde (34 g, 1.1 mol), MgCl$_2$ (23.4 g, 246 mmol) and Et$_3$N (86 mL, 610 mmol) in anhydrous MeCN (550 mL) was stirred under reflux for 2 hours. The reaction mixture was concentrated in vacuo to half the volume and then partitioned between Et$_2$O (200 mL) and 1 M HCl (200 mL). The aqueous phase was further extracted with Et$_2$O (400 mL), then the combined organic extracts were dried over MgSO$_4$ and filtered. The solution was concentrated in vacuo and the residue was purified by silica gel chromatography (330 g, 0-20% Et$_2$O in isohexane) to afford the title compound (2) (8.6 g, 35%) as a yellow solid: $^1$H NMR (400 MHz, DMSO-d$_6$) δ: 12.12 (1H, s), 10.29 (1H, s), 7.25 (1H, d), 6.61 (1H, d), 2.56 (3H, s), 2.20 (3H, s).

Step 2: tert-Butyl 4,7-dimethylbenzofuran-2-carboxylate (3)

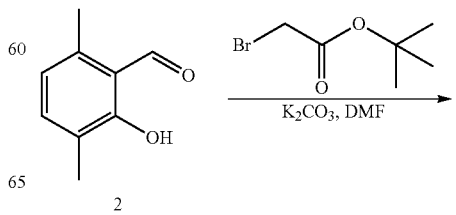

-continued

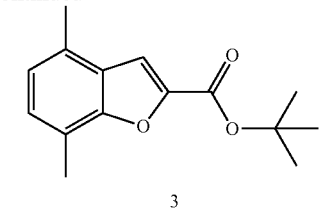

3 tert-Butyl 2-bromoacetate (10.6 mL, 71.5 mmol) was added dropwise to a stirred suspension of 2-hydroxy-3,6-dimethylbenzaldehyde (2) (8.6 g, 57 mmol) and potassium carbonate (19.8 g, 143 mmol) in anhydrous DMF (40 mL). The reaction mixture was stirred under reflux for 20 hours. The mixture was partitioned between EtOAc (100 mL) and water (100 mL) and the aqueous phase was further extracted with EtOAc (100 mL). The combined organics were washed with brine (5×100 mL) and concentrated in vacuo. The residue was purified by silica gel chromatography (330 g, 20% MeOH in dichloromethane (DCM)) to afford the title compound (3) (12.3 g, 87% yield) as a red oil: $^1$H NMR (400 MHz, DMSO-$d_6$) δ: 7.42 (1H, s), 7.04 (2H, dd), 8.33 (1H, d), 2.52 (3H, s), 2.50 (3H, s), 1.63 (9H, s).

Step 3: 4,7-Dimethylbenzofuran-2-carboxylic acid (4)

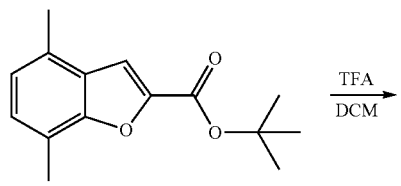

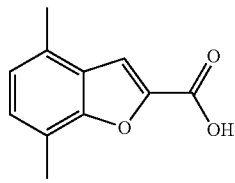

4

Trifluoroacetic acid (TFA) (19.2 mL, 249 mmol) was added dropwise to a solution of tert-butyl 4,7-dimethylbenzofuran-2-carboxylate (3) (12.3 g, 49.8 mmol) in DCM (100 mL) at 0° C. After the addition the mixture was allowed to warm to room temperature and stirred for 20 hours. The solvent was removed in vacuo and the residue was partitioned between EtOAc (100 mL) and 1 M HCl (100 mL). The aqueous phase was further extracted with EtOAc (100 mL) and the combined organic phases were washed with brine (300 mL) and then concentrated in vacuo. The residue was dissolved in EtOAc (100 mL) and then extracted with saturated NaHCO$_3$ solution (200 mL). The aqueous solution was acidified by the addition of concentrated HCl and extracted with EtOAc (200 mL). The organic solution was concentrated in vacuo and co-evaporated with toluene to afford the title compound (4) (7.7 g, 81% yield) as a pale brown solid: m/z 190 [M+H]$^+$ (ES$^+$). $^1$H NMR (400 MHz, DMSO-$d_6$) δ: 13.48 (1H, s), 7.72 (1H, s), 7.11 (2H, dd), 2.47 (3H, s), 2.44 (3H, s).

Step 4: Methyl 4-(5-(4,7-dimethylbenzofuran-2-yl)-1,2,4-oxadiazol-3-yl)benzoate (6)

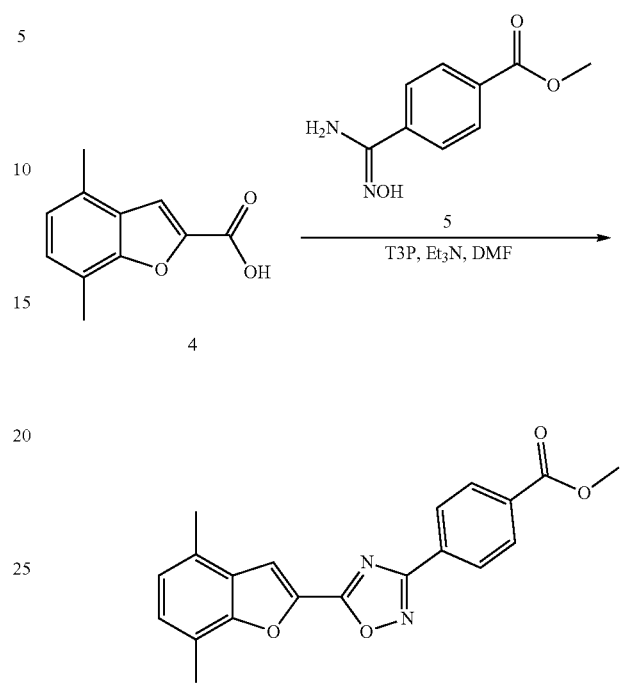

6

A solution of 2-propanephosphonic acid anhydride (T3P) in EtOAc (50%) (23.2 mL, 39.4 mmol) was added dropwise to a mixture of 4,7-dimethylbenzofuran-2-carboxylic acid (4) (3.0 g, 16 mmol), methyl 4-(N'-hydroxycarbamimidoyl)benzoate (5) (3.1 g, 16 mmol) and Et$_3$N (11 mL, 79 mmol) in anhydrous N,N-dimethylformamide (DMF) (25 mL) at 0° C. The mixture was stirred at 0° C. for 10 minutes then warmed to 90° C. and stirred for 18 hours. The reaction mixture was cooled to room temperature and poured into iced water (150 mL). The solid was collected, washed with cold EtOAc and dried under suction. The material was purified by trituration with MeOH and dried in vacuo to afford the title compound (6) (3.6 g, 65% yield) as a pink solid: m/z 349 [M+H]$^+$ (ES$^+$). $^1$H NMR (400 MHz, DMSO-$d_6$) δ:8.29-8.26 (3H, m), 8.19 (2H, d), 7.29 (1H, d), 7.13 (1H, d), 3.92 (3H, s), 2.56 (3H, s), 2.54 (3H, s).

Step 5: 4-(5-(4,7-Dimethylbenzofuran-2-yl)-1,2,4-oxadiazol-3-yl)benzoic acid (BHBA-001)

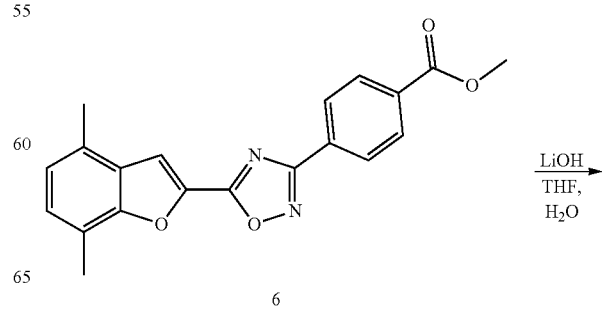

6

-continued

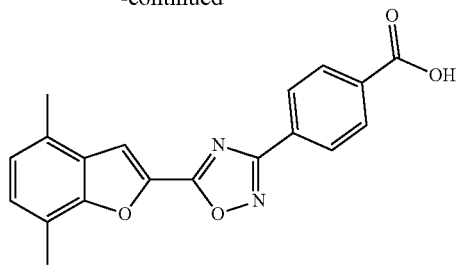

A suspension of methyl 4-(5-(4,7-dimethylbenzofuran-2-yl)-1,2,4-oxadiazol-3-yl)benzoate (6) (100 mg, 0.287 mmol) in tetrahydrofuran (THF) (1 mL) was treated with LiOH (2 M, aqueous, 720 μL, 1.4 mmol) and the mixture was stirred at 40° C. for 20 hours. The reaction mixture was cooled to room temperature, then acidified by the dropwise addition of 1 M HCl. The resulting solid was collected by filtration, then dissolved in MeOH and evaporated to dryness to afford the title compound (BHBA-001) (95 mg, 99% yield) as a white solid: m/z 335 [M+H]$^+$ (ES$^+$), 333 [M−H]$^-$ (ES). $^1$H NMR (400 MHz, DMSO-d$_6$) δ:13.34 (1H, br. s), 8.25-8.23 (3H, m), 8.16 (2H, d), 7.29 (1H, d), 7.12 (1H, d), 2.56 (3H, s), 2.53 (3H, s).

Another method for the preparation of BHBA-001 is shown in Scheme 2 below.

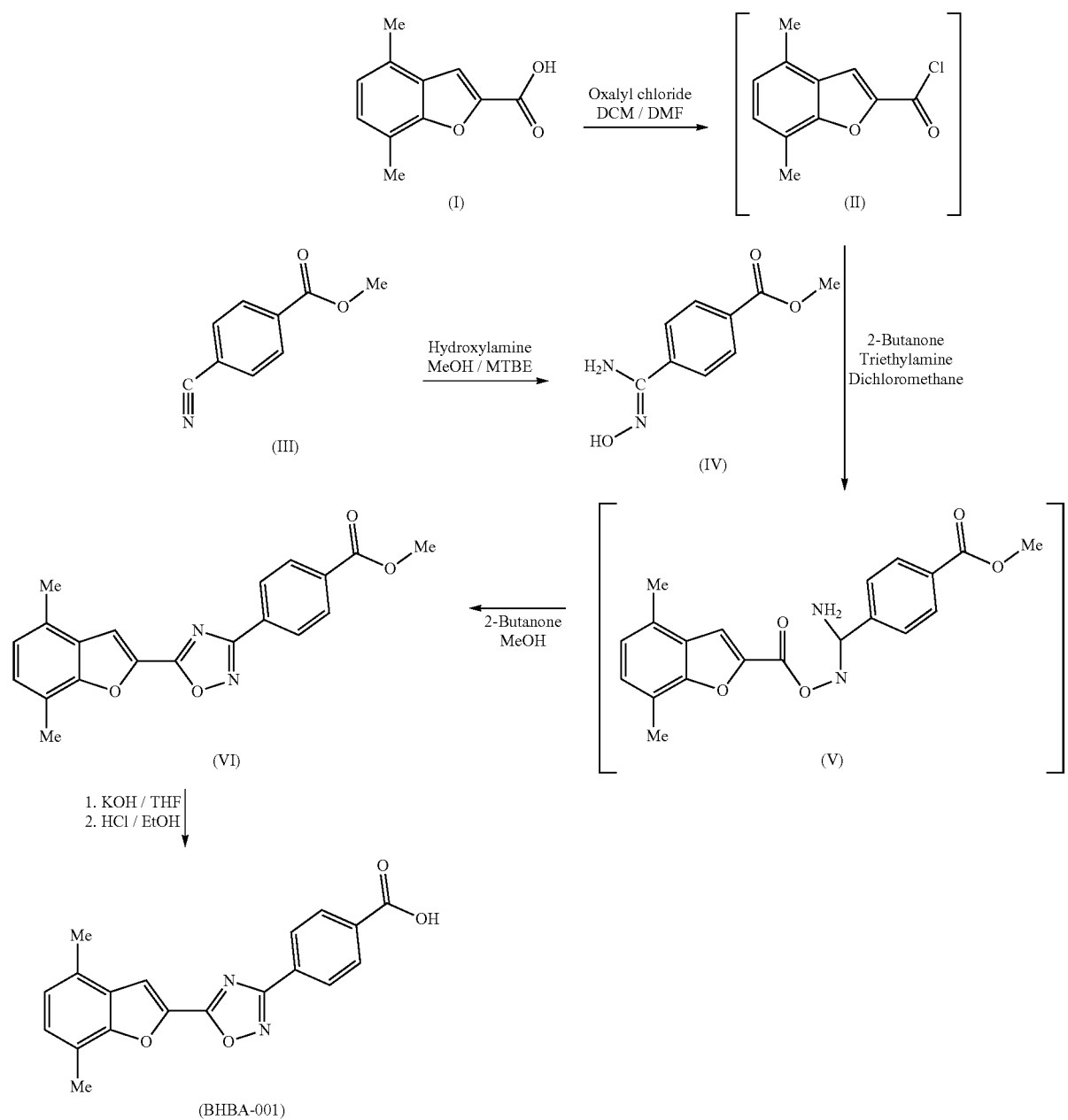

In this approach, methyl 4-cyanobenzoate (III) is treated with aqueous hydroxylamine in methanol as solvent. After completion of the reaction, methyl tertbutyl ether (MTBE) is added, the mixture is cooled, and after ageing overnight, the product methyl 4-(N'-hydroxycarbamimidoyl)benzoate (IV) is isolated as a solid.

4,7-Dimethylbenzofuran-2-carboxylic acid (I) is treated with oxalyl chloride in dichloromethane in the presence of catalytic N,N-dimethylformamide. After completion of the reaction, the solution containing the product 4,7-dimethyl-benzofuran-2-carbonyl chloride (II) is telescoped to the next stage.

4,7-Dimethylbenozfuran-2-carbonyl chloride (II) is treated with methyl 4-(N'-hydroxycarbamimidoyl)benzoate (IV) in the presence of triethylamine as base and 2-butanone as solvent. After removal of the solvent the penultimate intermediate methyl 4-[5-(4,7-dimethylbenzofuran-2-yl)-1,2,4-oxadiazol-3-yl]benzoate (VI) is crystallised from methanol and isolated by filtration.

Methyl 4-[5-(4,7-dimethylbenzofuran-2-yl)-1,2,4-oxadiazol-3-yl]benzoate (VI) is hydrolysed by treatment with potassium hydroxide in tetrahydrofuran (THF) at 60-65° C., and subsequently diluted with water and ethanol. Upon addition of concentrated hydrochloric acid, the target compound 4-[5-(4,7-dimethylbenzofuran-2-yl)-1,2,4-oxadiazol-3-yl]benzoic acid (BHBA-001) precipitates and is isolated by filtration.

An example of this synthetic route is described below.

Step 1: Methyl 4-(N'-hydroxycarbamimidoyl)benzoate (IV)

A solution of methyl 4-cyanobenzoate (III) (2.50 kg, 1 wt) in methanol (7.5 L, 3 vol) was diluted with methyl tert.-butyl ether (9.3 kg, 3.7 wt). Aqueous hydroxylamine (50% solution; 1.23 kg, 0.5 wt, 1.2 eq.) was dosed over approximately 0.5 hours at 20-25° C. The dosing lines were rinsed with methanol (1 kg, 0.4 wt) and the reaction allowed to proceed for approximately 12 hours at 20-25° C. The batch was cooled to 5±5° C. and aged at 5±5° C. for 3 hours. The product, methyl 4-(N'-hydroxycarbamimidoyl)benzoate (IV), was isolated by filtration, washed with methyl tert.-butyl ether (2×5.5 kg, 2×2.2 wt), and dried under a flow of nitrogen at ambient for approximately 4 hours (2.38 kg, 93%).

Step 2: 4,7-Dimethylbenozfuran-2-carbonyl chloride (II)

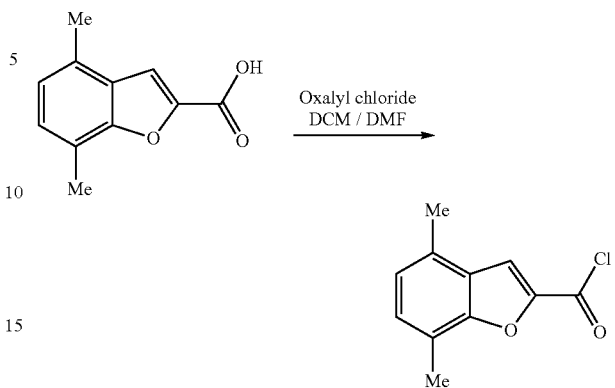

A reactor was charged with 4,7-dimethylbenzofuran-2-carboxylic acid (I) (1.96 kg, 1 wt), N,N-dimethylformamide (8 g, 0.004 wt) and dichloromethane (6.85 kg, 3.5 wt) and the batch was heated to 25-30° C. Over a period of about 15 minutes, oxalyl chloride (1.47 kg, 0.75 wt, 1.1 eq) was dosed to the mixture, and the dosing lines were rinsed with dichloromethane (1.3 kg, 0.66 wt). The batch was stirred for approximately 1.5 hours at 30-35° C. and the resultant product, 4,7-dimethylbenozfuran-2-carbonyl chloride (II), was used directly in the next step without any further purification.

Step 3: Methyl 4-[5-(4,7-dimethylbenzofuran-2-yl)-1,2,4-oxadiazol-3-yl]benzoate (VI)

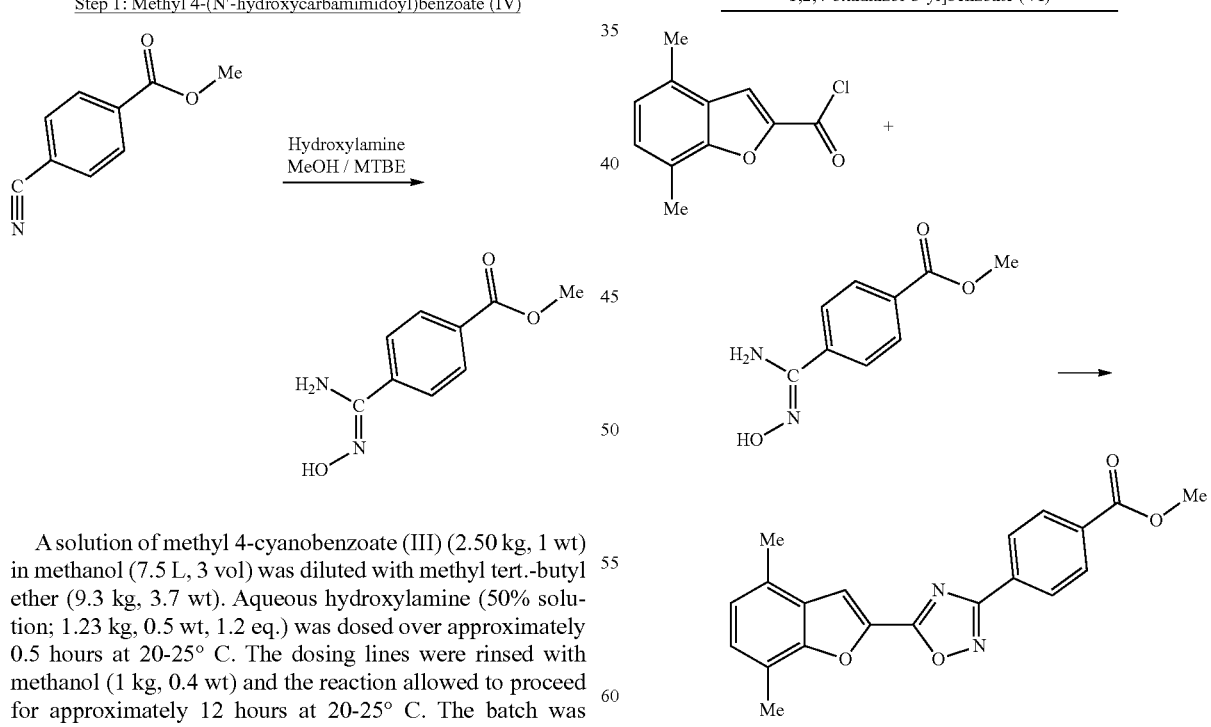

A reactor was charged with methyl 4-(N'-hydroxycarbamimidoyl)benzoate IV) (1.97 kg, 1 wt, 0.97 eq based on (I)), triethylamine (2.34 kg, 1.2 wt, 2.2 eq) and methyl isobutyl ketone (23.9 kg, 12 wt). The batch was heated to 30-35° C. and dosed with the solution of 4,7-dimethylbenozfuran-2- carbonyl chloride (II) (prepared in Step 2), ensuring that the temperature did not exceed 60° C. The dosing lines were rinsed with dichloromethane (0.66 wt) and the solvent was initially distilled to remove some solvent, and then heated under atmospheric pressure at 110-115° C. for approximately 3 hours. The batch was cooled to 60-70° C., methanol (8 kg, 4 wt) was added, and the batch was heated at this temperature for another 30 minutes. The batch was cooled to 20±3° C. and aged at this temperature for approximately 1 hour. The solid product was filtered, washed with methanol (2×6.2 kg, 2×3.1 wt), and dried under a flow of nitrogen at ambient temperature for 16 hours (3.3 kg, 93%).

Step 4: 4-[5-(4,7-dimethylbenzofuran-2-yl)-1,2,4-oxadiazol-3-yl]benzoic acid (BHBA-001)

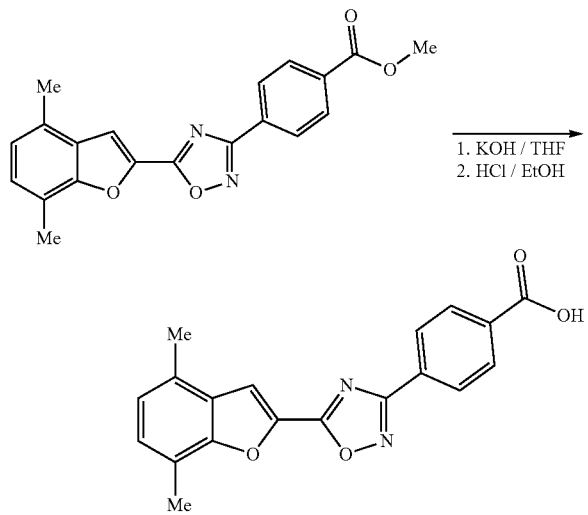

A reactor was charged with methyl 4-[5-(4,7-dimethylbenzofuran-2-yl)-1,2,4-oxadiazol-3-yl]benzoate (VI) (3.0 kg, 1 wt), tetrahydrofuran (THF) (22 kg, 7.1 wt) and a solution of aqueous potassium hydroxide, prepared from solid KOH, (0.69 kg, 0.23 wt) in demineralized water (DEMI water, 7.5 kg, 2.5 wt). The batch was heated to 65±5° C. and stirred for approximately 3 hours at 65±5° C. The batch was cooled to 30-35° C., and the reaction mixture was discharged. This solution was charged to a reactor via an in-line filter (i.e., a clarification step). The reactor was charged, via an in-line filter, with DEMI water (6 kg, 2.0 wt) and absolute ethanol (9.6 kg, 3.2 wt). The batch was heated to 55±5° C. The reactor was dosed, via an in-line filter, with concentrated (30 wt %) hydrochloric acid (1.35 kg, 0.45 wt) and the batch was stirred for approximately 15 minutes at 55±5° C. The batch was cooled to 20±3° C. and aged at this temperature for 2 hours. The product was filtered and the filter cake was washed twice with a mixture of DEMI water (1.5 kg, 0.5 wt) and ethanol absolute (8.4 kg, 2.8 wt). The batch was dried on the filter for approximately 1 hour at ambient temperature to give the target compound, BHBA-001.

Screening Studies

Study 1: Solubility Studies

The solubility of BHBA-001 (characterised by XRPD as Form 1) was determined in 15 solvents to study the initial polymorphic behaviour. A shake-flask method was applied in which solid was added stepwise (e.g., 10 mg at a time) to a known amount of solvent (e.g., 3 mL). The solubility was confirmed visually. After the addition, the suspension/solution was held for 24 hours at 20° C. in order to check for slow dissolution or recrystallization. If the solid was not completely dissolved, the suspension was heated to 50° C. to encourage dissolution. The solvent was then removed by evaporation, in some cases, with the help of anti-solvent. The resulting solid was analysed using XRPD.

The results are summarised in the following table. The compound was only poorly soluble in most solvents. However, two new crystalline forms were identified: Form 2 and Form 3.

TABLE 5

Solubility Studies

| # | Solvent | Solubility (at 20° C.) (mg/ml) | Form (from XRPD) |
|---|---------|-------------------------------|------------------|
| 1 | dichloromethane | <3 | Form 1 |
| 2 | methyl tert-butyl ether | <3 | Form 1 |
| 3 | acetone | <3* | Amorphous |
| 4 | ethyl acetate | <4 | Form 1 |
| 5 | ethanol | <4 | Form 2 |
| 6 | acetonitrile | <4 | Form 1 |
| 7 | n-heptane | <3 | Form 1 |
| 8 | water | <3 | Form 1 |
| 9 | toluene | <3 | Form 1 |
| 10 | acetic acid | <4 | Form 3 |
| 11 | tetrahydrofuran (THF) | 9-30 | Form 1 |
| 12 | 2-methyltetrahydrofuran | 5-10 | Form 1 |
| 13 | 2-propanol | <3 | Form 1 |
| 14 | isopropyl acetate | 4 | Form 1 |
| 15 | 1-propanol | <3 | Form 1 |

*Solubility at 50° C.

Study 2: Slurry Studies

Due to its low solubility, BHBA-001 (Form 1) was slurried with various solvents in order to observe recrystallization effects, using three different temperature profiles: (a) at 20° C. for 5 days; (b) at 5° C. for 2 days; and (c) heating to 60° C. followed by a slow cooling profile of 5° C./hour from 60° C. to 5° C. After slurrying, the liquid was decanted, and the remaining solids were dried under a stream of nitrogen and analysed using XRPD.

The results are summarised in the following tables. In almost every case, the slurry studies yielded Form 1. However, one new crystalline form was identified (Form 4).

In the slow cooling studies, all of which yielded Form 1, the particle habit changed to elongated particles of 5-10 μm.

TABLE 6

Slurry Studies: 50° C./2 days

| # | Solvent | XRPD |
|---|---------|------|
| 1 | 2-propanol | Form 1 |
| 2 | 1-propanol | Form 1 |
| 3 | acetone | Form 4 |
| 4 | 2-butanone (MEK) | Form 4 |
| 5 | ethyl acetate | Form 1 |
| 6 | isopropyl acetate | Form 1 |
| 7 | acetonitrile | Form 1 |
| 8 | methyl tert-butyl ether | Form 1 |
| 9 | tetra hydrofuran (THF) | Form 1 |
| 10 | diisopropyl ether | Form 1 |
| 11 | 2-methyltetrahydrofuran | Form 1 |
| 12 | toluene | Form 1 |
| 13 | anisole | Form 1 |
| 14 | cyclohexane | Form 1 |

TABLE 6-continued

Slurry Studies: 50° C./2 days

| # | Solvent | XRPD |
|---|---------|------|
| 15 | n-heptane | Form 1 |
| 16 | dichloromethane | Form 1 |

TABLE 7

Slurry Studies: 20° C./5 days

| # | Solvent | XRPD |
|---|---------|------|
| 1 | 2-propanol | Form 1 |
| 2 | 1-propanol | Form 1 |
| 3 | acetone | Form 4 |
| 4 | 2-butanone (MEK) | Form 1 |
| 5 | ethyl acetate | Form 1 |
| 6 | isopropyl acetate | Form 1 |
| 7 | acetonitrile | Form 1 |
| 8 | methyl tert-butyl ether | Form 1 |
| 9 | tetrahydrofuran (THF) | Form 1 |
| 10 | diisopropyl ether | Form 1 |
| 11 | 2-methyltetrahydrofuran | Form 1 |
| 12 | toluene | Form 1 |
| 13 | anisole | Form 1 |
| 14 | cyclohexane | Form 1 |
| 15 | n-heptane | Form 1 |
| 16 | dichloromethane | Form 1 |

TABLE 8

Slurry Studies: 60° C. to 5° C. at 5° C./h

| # | Solvent | XRPD |
|---|---------|------|
| 1 | 2-propanol | Form 1 |
| 2 | 1-propanol | Form 1 |
| 3 | acetone | Form 1 |
| 4 | 2-butanone (MEK) | Form 1 |
| 5 | ethyl acetate | Form 1 |
| 6 | isopropyl acetate | Form 1 |
| 7 | acetonitrile | Form 1 |
| 8 | methyl tert-butyl ether | Form 1 |
| 9 | tetrahydrofuran (THF) | Form 1 |
| 10 | diisopropyl ether | Form 1 |
| 11 | 2-methyltetrahydrofuran | Form 1 |
| 12 | toluene | Form 1 |
| 13 | anisole | Form 1 |
| 14 | cyclohexane | Form 1 |
| 15 | n-heptane | Form 1 |
| 16 | dichloromethane | Form 1 |

Study 3: Slurry Studies (for Hydrates)

Additional slurry studies were performed using several water-methanol mixtures in an effort to determine if a hydrate would be formed.

The results are summarised in the following table. No new crystalline forms (and thus no hydrates) were identified.

TABLE 9

Slurry Studies: Hydrates

| # | MeOH:H$_2$O ratio (v/v) | Temperature profile | XRPD |
|---|------|------|------|
| 1 | 95:5 | 20° C.; 3 days | Form 1 |
| 2 | 90:10 | 20° C.; 3 days | Form 1 |
| 3 | 75:25 | 20° C.; 3 days | Form 1 |
| 4 | 50:50 | 20° C.; 3 days | Form 1 |
| 5 | 25:75 | 20° C.; 3 days | Form 1 |

Study 4: Competitive Slurry Studies

Competitive slurry experiments were performed in a number of different solvents (data not shown). A mixture of Forms 1, 2, 3 and 4 was slurried with each solvent, and resulting solids were analysed by XRPD. The competitive slurry study indicated that it is the solvent (not the temperature) that determines which polymorph will be formed.

Characterisation of the Crystalline Forms Identified in the Screening Studies

Characterisation Methods

The various crystalline forms of BHBA-001 can be identified by their unique solid state signatures with respect to, for example, X-ray powder diffraction (XRPD), differential scanning calorimetry (DSC), and other solid state methods.

Further characterisation with respect to water content or solvent content of the crystalline forms can be gauged by any of various routine methods, such as thermogravimetric analysis (TGA), differential scanning calorimetry (DSC), dynamic vapour sorption (DVS), and other techniques.

X-ray Powder Diffraction (XRPD):

The XRPD studies were performed using a Bruker AXS D2 PHASER in Bragg-Brentano configuration (Equipment #1549) using Cu-K$_\alpha$ radiation. The experimental parameters were: a Cu anode at 30 kV, 10 mA; sample stage standard rotating; monochromatisation by a Kβ-filter (0.5% Ni); slits: fixed divergence slits 1.0 mm (=0.61°), primary axial Soller slit 2.5°, secondary axial Soller slit 2.5°; detector linear detector LYNXEYE with receiving slit 5° detector opening. The standard sample holder (0.1 mm cavity in (510) silicon wafer) has a minimal contribution to the background signal.

The measurement conditions were: scan range: 5-45° 2θ; sample rotation: 5 rpm, 0.5 s/step, 0.010°/step, 3.0 mm detector slit. To confirm system suitability, corundum sample A26-B26-S(NIST standard) was measured daily.

The software used for data collection was Diffrac.Commander v3.3.35. Data analysis was done using Diffrac.Eva V3.0. No background correction or smoothing was applied to the diffraction patterns. The contribution of the Cu-K$\alpha_2$ was stripped off using the Diffrac.Eva software.

For XRPD, the relative intensities of the peaks can vary, depending upon the sample preparation technique, the sample mounting procedure and the particular instrument employed. Moreover, instrument variation and other factors can affect the 2θ values. Therefore, the peak assignments of diffraction patterns can vary, typically by plus or minus about 0.2° (e.g., ±0.2°).

Thermo Gravitational Analysis/Differential Scanning Calorimetry (TGA/DSC):

The TGA/DSC studies were performed using a Mettler Toledo TGA/DSCI STARe System with a 34-position auto sampler (Equipment #1547).

The samples were prepared using aluminium crucibles (40 μL; pierced). Typically, 5-10 mg of sample was loaded into a pre-weighed aluminium crucible and was kept at 30° C. for 5 minutes, after which it was heated at 10° C./min from 30° C. to 300° C. A nitrogen purge of 40 mL/min was maintained over the sample. To confirm system suitability, indium and zinc are used as references.

The software used for data collection and evaluation was STARe Software v10.00 build 2480. No corrections were applied to the thermogram.

For DSC, it is known that the temperature observed will depend upon the rate of temperature change as well as sample preparation technique and the particular instrument employed. Thus, the values reported herein relating to DSC thermograms can vary by plus or minus about 4° C.

Differential Scanning Calorimetry (DSC):

The DSC studies were performed using a Mettler Toledo DSCI STARe System, (Equipment #1564).

The samples were made using aluminum crucibles (40 μL; pierced). Typically, 1-8 mg of sample was loaded onto a pre-weighed aluminium crucible and was kept at 30° C. for 5 minutes, after which it was heated at 10° C./min from 30° C. to 350° C. and kept at 350° C. again. A nitrogen purge of 40 mL/min was maintained over the sample. To confirm system suitability, Indium and Zinc are used as references.

The software used for data collection and evaluation is STARe Software v10.00 build 2480. No corrections are applied to the thermogram.

For DSC, it is known that the temperature observed will depend upon the rate of temperature change as well as sample preparation technique and the particular instrument employed. Thus, the values reported herein relating to DSC thermograms can vary by plus or minus about 4° C.

Dynamic Vapour Sorption (DVS):

The DVS studies were performed using a Surface Measurement Systems Ltd. DVS-1 No Video (Equipment #2126).

The sample was weighed in a glass pan, typically 20-30 mg, and equilibrated at 0% RH. After the material had dried, the relative humidity (RH) was increased with 10% per step for 1 hour per increment, ending at 95% RH.

The software used for data collection was DVSWn v3.01 No Video. Data analysis was performed using DVS Standard Analysis Suite v6.3.0 (Standard).

Polarized Light Microscopy (PLM):

The microscopy studies were performed using an Axio-Vert 35M, equipped with an AxioCamERc 5s (Equipment #1612).

The microscope was equipped with four lenses: Zeiss A-Plan Sx/0.12; Zeiss A-plan IOx/0.25; LD A-Plan 20x/0.30; and Achros TIGMAT 32x/0.40.

Data collection and evaluation was performed using Carl Zeiss Zen AxioVision Blue Edition Lite 2011 v.0.0.0 software. A small amount of sample was loaded on an object glass and spread until a thin layer was obtained.

Stability Studies:

Stability studies were performed as follows. Samples were packaged in double low density polyethylene bags, sealed with plastic ties, and placed in high-density polyethylene (HDPE) drums. The samples were stored at the following storage conditions: 25° C./60% RH (simulating "real time") and 40° C./75% RH ("accelerated").

The samples were tested periodically for visual appearance, drug content (by HPLC), water content (by Karl Fischer titration), and drug-related impurities (by HPLC).

Drug content, corrected to a water and solvent free basis, is calculated from the following equation: Content (%)=100−(water+solvents+residue on ignition+related impurities).

Drug-related impurities were determined using a reverse-phase gradient HPLC method with UV detection at 254 nm, using a 150 mm×4.6 mm, 3 μm Waters Atlantis T3 column, with the following parameters:

TABLE 10

| HPLC Parameters | |
|---|---|
| HPLC Column: | Waters Atlantis T3 C18, 150 × 4.6 mm, 3 μm |

TABLE 10-continued

| HPLC Parameters | |
|---|---|
| Mobile Phase A: | 5 mM ammonium acetate in water/formic acid buffer |
| Mobile Phase B: | Acetonitrile |
| Detection: | UV 254 nm |
| Injection Volume: | 10 μL |
| Column Temperature: | 25° C. |
| Flow Rate: | 0.8 mL/min |

TABLE 11

| HPLC Gradient | | |
|---|---|---|
| Time (Minutes) | % A | % B |
| 0.0 | 90 | 10 |
| 10.0 | 10 | 90 |
| 15.0 | 10 | 90 |
| 15.1 | 90 | 10 |
| 20.0 | 90 | 10 |

Crystalline Form 1

FIG. 1 shows an X-ray powder diffraction (XRPD) pattern for a sample containing crystalline Form 1 of BHBA-001.

The 25-most intense peaks in the XRPD pattern are listed in the following table.

TABLE 12

| XRPD Peaks for Crystalline Form 1 of BHBA-001 | | | | |
|---|---|---|---|---|
| No. | Scattering Angle (2θ) | d Value | Relative Intensity | Rank |
| 1 | 6.680 | 13.22182 | 2.9% | 21 |
| 2 | 8.241 | 10.71991 | 21.2% | 9 |
| 3 | 8.809 | 10.03078 | 26.9% | 5 |
| 4 | 10.941 | 8.07973 | 21.9% | 8 |
| 5 | 12.243 | 7.22327 | 17.5% | 11 |
| 6 | 13.081 | 6.76273 | 100.0% | 1 |
| 7 | 13.711 | 6.45350 | 9.9% | 14 |
| 8 | 16.332 | 5.42315 | 24.4% | 7 |
| 9 | 16.552 | 5.35150 | 16.5% | 12 |
| 10 | 17.151 | 5.16578 | 12.2% | 13 |
| 11 | 17.541 | 5.05189 | 61.0% | 3 |
| 12 | 17.956 | 4.93615 | 26.0% | 6 |
| 13 | 19.504 | 4.54776 | 4.1% | 20 |
| 14 | 20.088 | 4.41683 | 1.8% | 24 |
| 15 | 21.601 | 4.11062 | 19.2% | 10 |
| 16 | 23.052 | 3.85515 | 2.5% | 22 |
| 17 | 23.017 | 3.86094 | 2.4% | 23 |
| 18 | 24.005 | 3.70426 | 29.8% | 4 |
| 19 | 25.117 | 3.54260 | 6.1% | 16 |
| 20 | 26.210 | 3.39730 | 5.0% | 17 |
| 21 | 26.964 | 3.30403 | 73.1% | 2 |
| 22 | 27.570 | 3.23277 | 5.0% | 18 |
| 23 | 28.988 | 3.07776 | 6.8% | 15 |
| 24 | 30.468 | 2.93159 | 4.6% | 19 |
| 25 | 32.446 | 2.75724 | 1.8% | 25 |

FIG. 2 shows a differential scanning calorimetry (DSC) thermogram for a sample containing crystalline Form 1 of BHBA-001.

The DSC thermogram was characterised by a broad desolvation event between 40-100° C. (onset: 36.36° C.; peak: 65.72° C.; heat flow: −59.70 J/g) followed by an endothermic event (melting point) with peak at about 277° C. (onset: 273.21° C.; peak: 277.23° C.; heat flow: −114.90 J/g). A small broad event also appeared at 200-250° C. (onset: 207.01° C.; peak: 235.94° C.; heat flow: −144.44 J/g).

FIG. 3 shows both a thermogravimetric analysis (TGA) thermogram and a differential scanning calorimetry (DSC) thermogram for a sample containing a crystalline Form 1 of BHBA-001.

The DSC thermogram was characterised by a broad endothermic event between 40-100° C. (onset: 77.78° C.; peak: 94.83° C.; heat flow: −27.26 J/g) which was associated with a weight loss of 2.35% w/w by TGA. Two glass transition endotherms were observed: a first event with an onset temperature of 219° C. (onset: 219.63° C.; midpoint: 237.19° C.), associated with a weight loss of 2.7% w/w by TGA; and a second event with an onset temperature of 256° C. (onset: 256.33° C.; midpoint: 258.04° C.), associated with a weight loss of 1.13% w/w by TGA. The Form 1 endothermic melt had an observed onset temperature of 273° C. (onset 272.98° C.; peak: 277.33° C.; heat flow: −155.35 J/g).

FIG. 4 shows a dynamic vapour sorption (DVS) sorption-desorption plot for a sample containing crystalline Form 1 of BHBA-001.

To determine the hygroscopicity of Form 1, a DVS plot was measured at 25° C. for a double sorption-desorption cycle. The total mass uptake was 8.7% w/w between 0% and 95% RH, which characterised Form 1 as a hygroscopic form. The uptake was reversible and reproducible.

FIG. 5 shows a dynamic vapour sorption (DVS) mass uptake plot for a sample containing crystalline Form 1 of BHBA-001.

A DVS plot was recorded for a sample of Form 1 at 25° C. and equilibrated at 0% RH. After the material had dried, the RH was increased with 10% per step for 1 hour per increment, ending at 95% RH and a final mass uptake of 8.7% w/w. The RH was decreased with 10% per step for 1 hour per increment back to 0% RH. Form was characterised as a hygroscopic form. The uptake was reversible and reproducible.

FIG. 6 shows a polarized light microscopy (PLM) micrograph for sample containing crystalline Form (of BHBA-001.

Form 1 was characterised as agglomerates of very small particles.

The physical properties of crystalline Form 1 of BHBA-001 are summarised in the following table.

TABLE 13

Physical Data for Crystalline Form 1 of BHBA-001

| Method | FIG. | Summary |
|---|---|---|
| XRPD | 1 | Peaks of about 10% relative intensity or greater, at 2θ values of about 13.1°, 27.0°, 17.5°, 24.0°, 8.8°, 18.0°, 16.3°, 10.9°, 8.2°, 21.6°, 12.2°, 16.6°, 17.2°, and 13.7° |
| DSC | 2 | Events at $T_{peak}$ about 65.7° C. (−59.7 J/g); $T_{peak}$ about 235.9° C. (−14.4 J/g); and $T_{peak}$ about 277.2° C. (−114.9 J/g) |
| TGA | 3 | Decrease in weight of about 2.4% (approximately 78° C.) and about 1.1% (approximately 273° C.) |
| DVS | 4, 5 | Mass uptake of about 8.7% between 0% and 95% RH |
| Microscopy | 6 | Aggregated particles, ~1 pm |

Crystalline Form 1 of BHBA-001 contains 2.4% (by mass) of residual solvent (including water).

Crystalline Form 1 of BHBA-001 is hygroscopic with 8.7% w/w uptake of water between 0% and 95% RH.

Crystalline Form 2

FIG. 7 shows an X-ray powder diffraction (XRPD) pattern for a sample containing crystalline Form 2 of BHBA-001.

The 12-most intense peaks in the XRPD pattern are listed in the following table.

TABLE 14

XRPD Peaks for Crystalline Form 2 of BHBA-001

| No. | Scattering Angle (2θ) | d Value | Relative Intensity | Rank |
|---|---|---|---|---|
| 1 | 5.707 | 15.47411 | 5.3% | 11 |
| 2 | 8.054 | 10.96918 | 5.8% | 10 |
| 3 | 8.661 | 10.20180 | 24.9% | 5 |
| 4 | 10.408 | 8.49288 | 54.8% | 2 |
| 5 | 11.889 | 7.43804 | 12.2% | 6 |
| 6 | 12.734 | 6.94611 | 50.8% | 3 |
| 7 | 13.670 | 6.47246 | 4.5% | 12 |
| 8 | 15.628 | 5.66585 | 100.0% | 1 |
| 9 | 17.388 | 5.09601 | 50.6% | 4 |
| 10 | 21.280 | 4.17191 | 10.8% | 7 |
| 11 | 23.857 | 3.72685 | 6.1% | 9 |
| 12 | 26.731 | 3.33226 | 10.6% | 8 |

Form 2 (obtained from ethanol) was found to contain ethanol (via solution ¹H NMR; data not shown), and on the basis of XRPD and ¹H NMR data, was characterised as an ethanol solvate.

Crystalline Form 3

FIG. 8 shows an X-ray powder diffraction (XRPD) pattern for a sample containing crystalline Form 3 of BHBA-001.

The 12-most intense peaks in the XRPD pattern are listed in the following table.

TABLE 15

XRPD Peaks for Crystalline Form 3 of BHBA-001

| No. | Scattering Angle (2θ) | d Value | Relative Intensity | Rank |
|---|---|---|---|---|
| 1 | 7.089 | 12.46012 | 19.6% | 7 |
| 2 | 9.490 | 9.31245 | 23.5% | 5 |
| 3 | 11.114 | 7.95462 | 99.9% | 2 |
| 4 | 12.111 | 7.30210 | 10.2% | 10 |
| 5 | 12.449 | 7.10430 | 13.1% | 8 |
| 6 | 14.171 | 6.24470 | 100.0% | 1 |
| 7 | 16.138 | 5.48770 | 70.8% | 3 |
| 8 | 16.787 | 5.27710 | 41.4% | 4 |
| 9 | 18.915 | 4.68790 | 22.9% | 6 |
| 10 | 19.545 | 4.53818 | 3.9% | 12 |
| 11 | 21.502 | 4.12945 | 12.5% | 9 |
| 12 | 22.409 | 3.96420 | 4.3% | 11 |

Form 3 (obtained from acetic acid) was found to contain acetic acid (via solution ¹H NMR; data not shown), and on the basis of XRPD and ¹H NMR data, was characterised as an acetic acid solvate.

Crystalline Form 4

FIG. 9 shows an X-ray powder diffraction (XRPD) pattern for a sample containing crystalline Form 4 of BHBA-001.

The 32-most intense peaks in the XRPD pattern are listed in the following table.

TABLE 16

XRPD Peaks for Crystalline Form 4 of BHBA-001

| No. | Scattering Angle (2θ) | d Value | Relative Intensity | Rank |
|---|---|---|---|---|
| 1 | 8.184 | 10.79535 | 1.5% | 14 |
| 2 | 9.517 | 9.28608 | 6.0% | 3 |

TABLE 16-continued

XRPD Peaks for Crystalline Form 4 of BHBA-001

| No. | Scattering Angle (2θ) | d Value | Relative Intensity | Rank |
|---|---|---|---|---|
| 3 | 10.443 | 8.46426 | 0.9% | 23 |
| 4 | 12.417 | 7.12294 | 1.8% | 10 |
| 5 | 12.698 | 6.96583 | 1.8% | 11 |
| 6 | 13.093 | 6.75638 | 2.7% | 5 |
| 7 | 14.432 | 6.13245 | 1.9% | 9 |
| 8 | 14.799 | 5.98109 | 100.0% | 1 |
| 9 | 15.301 | 5.78590 | 1.1% | 19 |
| 10 | 16.418 | 5.39499 | 4.4% | 4 |
| 11 | 18.821 | 4.71111 | 1.1% | 20 |
| 12 | 19.095 | 4.64415 | 1.2% | 17 |
| 13 | 20.657 | 4.29637 | 10.6% | 2 |
| 14 | 20.977 | 4.23158 | 2.1% | 8 |
| 15 | 22.881 | 3.88346 | 1.2% | 18 |
| 16 | 23.864 | 3.72568 | 1.1% | 21 |
| 17 | 24.581 | 3.61871 | 2.3% | 6 |
| 18 | 25.022 | 3.55581 | 1.0% | 22 |
| 19 | 26.365 | 3.37771 | 1.6% | 13 |
| 20 | 26.722 | 3.33343 | 2.3% | 7 |
| 21 | 28.065 | 3.17681 | 1.8% | 12 |
| 22 | 30.031 | 2.97318 | 1.3% | 16 |
| 23 | 31.060 | 2.87703 | 1.4% | 15 |
| 24 | 35.798 | 2.50636 | 0.5% | 26 |
| 25 | 36.541 | 2.45706 | 0.3% | 31 |
| 26 | 37.038 | 2.42521 | 0.6% | 24 |
| 27 | 38.578 | 2.33188 | 0.4% | 29 |
| 28 | 40.538 | 2.22353 | 0.5% | 27 |
| 29 | 40.863 | 2.20663 | 0.3% | 32 |
| 30 | 41.510 | 2.17371 | 0.4% | 30 |
| 31 | 42.025 | 2.14826 | 0.5% | 28 |
| 32 | 44.080 | 2.05275 | 0.6% | 25 |

FIG. 10 shows a differential scanning calorimetry (DSC) thermogram for a sample containing crystalline Form 4 of BHBA-001.

The DSC thermogram was characterised by two endothermic events: a first event with a peak temperature of 268° C. (onset: 263.36° C.; peak: 268.07° C.; heat flow: −16.65 J/g) which corresponds to the melting of Form 4, combined with an exothermic event (recrystallization) with a peak temperature of 270° C. (onset: 269.80° C.; peak: 270.69° C.; heat flow: +2.61 J/g) followed by melt of Form 1 at a peak temperature of 279° C. (onset: 277.54° C.; peak: 279.19° C.; heat flow: −51.95 J/g).

FIG. 11 shows both a thermogravimetric analysis (TGA) thermogram and a differential scanning calorimetry (DSC) thermogram for a sample containing a crystalline Form 4 of BHBA-001.

The TGA thermogram showed a very small weight loss of 0.2% between 40-80° C. The DSC thermogram was characterised by two endothermic events: a first event with an onset temperature of 256° C. (onset: 256.09° C.; peak: 264.60° C.; heat flow: −16.34 J/g) which corresponds to the melting of Form 4, combined with a recrystallization and melt of Form 1 at an onset temperature of 278° C. (onset: 278.10° C.; peak: 279.77° C.; heat flow: −166.01 J/g).

FIG. 12 shows a dynamic vapour sorption (DVS) sorption-desorption plot for a sample containing crystalline Form 4 of BHBA-001.

To determine the hygroscopicity of Form 4, a DVS plot was measured at 25° C. for a double sorption-desorption cycle. The total mass uptake was 0.1% between 0% and 95% RH, which characterises Form 4 as a non-hygroscopic form.

FIG. 13 shows a dynamic vapour sorption (DVS) mass uptake plot for a sample containing crystalline Form 4 of BHBA-001.

A DVS plot was recorded for a sample of Form 4 at 25° C. and equilibrated at 0% RH. After the material had dried, the RH was increased with 10% per step for 1 hour per increment, ending at 95% RH and a final mass uptake of 0.1%. The RH was decreased with 10% per step for 1 hour per increment back to 0% RH. Form 4 was characterised as a non-hygroscopic form.

FIG. 14 shows a polarized light microscopy (PLM) micrograph for sample containing crystalline Form 4 of BHBA-001.

Form 4 was characterised as having a particle habit with a preferred shape of approximately 50-100 μm acicular particles.

The physical properties of crystalline Form 4 of BHBA-001 are summarised in the following table.

TABLE 17

Physical Data for Crystalline Form 4 of BHBA-001

| Method | FIG. | Summary |
|---|---|---|
| XRPD | 9 | Peaks of about 10% relative intensity or greater, at 2θ values of about 14.8° and 20.7°; additional peaks of about 2% relative intensity or greater, at 2θ values of about 9.5°, 16.4°, 13.1°, 24.6°, 26.7°, 21.0°, 14.4°, 12.4°, 12.7°, and 28.1° |
| DSC | 10 | Events at $T_{peak}$ about 268.1° C. (−16.7 J/g); $T_{peak}$ about 270.7° C. (+2.6 J/g), and $T_{peak}$ about 279.2° C. (−52.0 J/g) |
| TGA | 11 | Decrease in weight of about 0.2% (40-80° C.) |
| DVS | 12, 13 | Mass uptake of about 0.1% between 0% and 95% RH |
| Microscopy | 14 | Acicular particles, ~50-100 μm |

Stability studies (as described above) were performed for crystalline Form 4 of BHBA-01. The results are summarised in the following table.

TABLE 18

Stability Studies

| Storage Conditions | Storage Time (months) | Visual Appearance | Drug Content (% w/w) | Water content (% w/w) | Drug-Related Impurities (% area) |
|---|---|---|---|---|---|
| Initial | 0 | White powder | 100.1 | <0.1 | 0.03 |
| 25° C./60% RH | 3 | As initial | 98.7 | <0.1 | 0.06 |
| 25° C./60% RH | 6 | As initial | 100.2 | <0.1 | 0.05 |
| 25° C./60% RH | 9 | As initial | 99.2 | <0.1 | 0.03 |
| 25° C./60% RH | 12 | Off-white powder | 100.4 | <0.1 | 0.03 |
| 25° C./60% RH | 18 | Off-white powder | 101.1 | <0.1 | 0.07 |
| 25° C./60% RH | 24 | As initial | 101.5 | <0.1 | <0.03 |
| 40° C./75% RH | 3 | As initial | 98.3 | <0.1 | 0.10 |
| 40° C./75% RH | 6 | As initial | 99.8 | <0.1 | 0.05 |

The appearance of the sample remained essentially unchanged after 24 months storage at 25° C./60% RH and 6 months storage at 40° C./75% RH.

Water content remained essentially unchanged after 24 months storage at 25° C./60% RH and 6 months storage at 40° C./75% RH.

Drug content remained essentially unchanged after 24 months storage at 25° C./60% RH and 6 months storage at 40° C./75% RH.

Drug-related impurity levels remained essentially unchanged after 24 months storage at 25° C./60% RH and 6 months storage at 40° C./75% RH.

In summary, crystalline Form 4 of BHBA-001 was shown to be stable following at least 24 months storage at 25° C./60% RH and 6 months storage at 40° C./75% RH.

Preparation of Crystalline Form 4

The following protocol was developed for the preparation of crystalline Form 4. It has proven successful for large-scale batches, including at least one 2.5 kg batch.

In part 1 (deprotection), a solution of BHBA-001 is prepared from the corresponding methyl ester.

In part 2 (precipitation), the BHBA-001 is precipitated from the solution (as Form 1).

In part 3 (formation of Form 4), the BHBA-001 (Form 1) is slurried at elevated temperature in absolute ethanol (to give Form 4).

Part 1: Preparation of BHBA-001 in Solution
  Charge a reactor with methyl 4-(5-(4,7-dimethylbenzofuran-2-yl)-1,2,4-oxadiazol-3-yl)benzoate (1 wt) and tetrahydrofuran (7.1 wt).
  Charge to the reactor aqueous potassium hydroxide, prepared from solid KOH (0.23 wt) in demineralized water (2.5 wt).
  Heat the batch to 65±5° C.
  Stir the batch for at least 3 hours at 65±5° C.
  Cool the batch to 30±5° C.
  Discharge the reaction mixture.
  Charge the reaction mixture to a second reactor via an in-line filter.
  Charge to the second reactor, via an in-line filter, demineralized water (2.0 wt) and ethanol absolute (3.2 wt).
  Heat the batch to 55±5° C.

Part 2: Precipitation of BHBA-001 (Form 1)
  Dose to the second reactor, via an in-line filter, concentrated (30 wt %) hydrochloric acid (0.45 wt).
  Stir the batch for at least 15 minutes at 55±5° C.
  Cool the batch to 20±3° C.
  Age the batch for at least 2 hours at 20±3° C.
  Filter the batch.
  Wash the batch: Dose to the reactor, via an in-line filter, a mixture of demineralized water (0.5 wt) and ethanol absolute (2.8 wt), and use this solvent mixture to wash the filter cake.
  Wash the batch: Dose to the reactor, via an in-line filter, ethanol absolute (3.2 wt), and use this solvent to wash the filter cake.
  Dry the batch: Dry the batch on the filter, for at least 1 hour at ambient temperature (about 20° C.) (to give crystalline Form 1 of BHBA-001).

Part 3: Reslurry to Convert BHBA-001 (Form 1) to BHBA-001 (Form 4)
  Charge the filter cake to the reactor.
  Charge to the reactor, via an in-line filter, absolute ethanol (12.6 wt).
  Heat the mixture to reflux (approximately 78° C.), and stir at this temperature for at least 2 hours.
  Cool the batch to 20±3° C.
  Age the batch for at least 1 hour at 20±3° C.
  Filter the batch.
  Wash the batch: Dose to the reactor, via an in-line filter, methyl tert.-butyl ether (2×3.7 wt), and use this solvent mixture to wash the filter cake.
  Dry the batch: Dry the batch on the filter, for at least 1 hour at ambient temperature (about 20° C.) (to give crystalline Form 4 of BHBA-001).

Accordingly, another aspect of the invention is a method of preparing crystalline Form 4 of BHBA-001 comprising the steps, in order
  (a) heating a mixture of BHBA-001 and ethanol;
  (b) cooling said mixture; and
  (c) isolating said crystalline form from said mixture.

In one embodiment, said mixture of BHBA-001 and ethanol is a mixture of solid BHBA-001 and ethanol (e.g., a slurry).

In one embodiment, said solid BHBA-001 is crystalline Form 1 of BHBA-001.

In one embodiment, said heating is at a temperature of about 40° C. to the reflux temperature of said mixture (e.g., about 78° C.).

In one embodiment, said heating is at a temperature of about 50° C. to the reflux temperature of said mixture (e.g., about 78° C.).

In one embodiment, said heating is at a temperature of about 60° C. to the reflux temperature of said mixture (e.g., about 78° C.).

In one embodiment, said heating is at the reflux temperature of said mixture (e.g., about 78° C.) (e.g., said heating is refluxing).

In one embodiment, said heating is for a period of about 30 minutes to about 24 hours.

In one embodiment, said heating is for a period of about 30 minutes to about 12 hours.

In one embodiment, said heating is for a period of about 30 minutes to about 6 hours.

In one embodiment, said heating is for a period of about 30 minutes to about 3 hours.

In one embodiment, said heating is for a period of about 2 hours.

In one embodiment, said cooling is to a temperature of about 5° C. to about 30° C.

In one embodiment, said cooling is to a temperature of about 5° C. to about 25° C.

In one embodiment, said cooling is to a temperature of about 20° C.

In one embodiment, said cooling is followed by a step of (b') ageing said cooled mixture.

In one embodiment, said ageing is for a period of about 30 minutes to about 24 hours.

In one embodiment, said ageing is for a period of about 30 minutes to about 12 hours.

In one embodiment, said ageing is for a period of about 30 minutes to about 6 hours.

In one embodiment, said ageing is for a period of about 30 minutes to about 3 hours.

In one embodiment, said ageing is for a period of about 1 hour.

In one embodiment, said isolating is by filtration.

EXAMPLE

Part 1: Deprotection

A reactor was charged with methyl 4-[5-(4,7-dimethyl-benzofuran-2-yl)-1,2,4-oxadiazol-3-yl]benzoate (3.0 kg, 1 wt), tetrahydrofuran (22 kg, 7.1 wt) and a solution of aqueous potassium hydroxide, prepared from solid KOH, (0.69 kg, 0.23 wt) in demineralized water (DEMI water, 7.5 kg, 2.5 wt). The batch was heated to 65±5° C. and stirred for approximately 3 hours at 65±5° C. The batch was cooled to 30-35° C., and the reaction mixture was discharged. This solution was charged to a reactor via an in-line filter (i.e., a clarification step). The reactor was charged, via an in-line filter, with DEMI water (6 kg, 2.0 wt) and absolute ethanol (9.6 kg, 3.2 wt). The batch was heated to 55±5° C.

Part 2: Precipitation

The reactor was dosed, via an in-line filter, with concentrated (30 wt %) hydrochloric acid (1.35 kg, 0.45 wt) and the batch was stirred for approximately 15 minutes at 55±5° C. The batch was cooled to 20±3° C. and aged at this temperature for 2 hours. The product was filtered and the filter cake was washed twice with a mixture of DEMI water (1.5 kg, 0.5 wt) and ethanol absolute (8.4 kg, 2.8 wt). The batch was dried on the filter for approximately 1 hour at ambient temperature to give the target compound, BHBA-001.

Part 3: Formation of Crystalline Form 4

The filter cake was charged to a reactor and absolute ethanol (37.8 kg, 12.6 wt) was dosed, via an in-line filter. The mixture was heated to reflux, and the suspension stirred at this temperature for approximately 2 hours. The batch was cooled to 20±3° C. and aged at this temperature for approximately 1 h at 20±3° C. The solid was filtered, washed with methyl tert.-butyl ether (2×11 kg, 2×3.7 wt), and dried under a flow of nitrogen at ambient temperature for 20 hours to give the target compound, BHBA-001 (2.52 kg, 80%) in crystalline Form 4.

Compositions, Formulations, and Medical Use

Compositions

One aspect of the present invention pertains to a composition (e.g., a pharmaceutical composition) comprising a crystalline form of BHBA-001 (e.g., Form 4), as described herein, and a pharmaceutically acceptable carrier, diluent, or excipient.

In one embodiment, the composition is a composition (e.g., a pharmaceutical composition) comprising a crystalline Form 4 of BHBA-001, which is substantially free of other crystalline forms of BHBA-001 (e.g., Forms 1, 2, and 3).

As used in this context, "substantially free of other crystalline forms of BHBA-001" means that the ratio of (a) the total weight of other crystalline forms of BHBA-001 (e.g., Forms 1, 2, and 3) to (b) the weight of crystalline Form 4 of BHBA-001, in the overall composition, is less than about 1:10, preferably less than about 1:20, more preferably less than about 1:50.

Another aspect of the present invention pertains to a method of preparing a composition (e.g., a pharmaceutical composition) comprising mixing a crystalline form of BHBA-001 (e.g., Form 4), as described herein, and a pharmaceutically acceptable carrier, diluent, or excipient.

Uses

BHBA-001 (including crystalline forms of BHBA-001 (e.g., Form 4), as described herein) is useful, for example, in the treatment of diseases and conditions that are ameliorated by the (selective) activation of RARβ (e.g., RARβ2), such as, for example, neurological injuries such as spinal cord injuries.

Use in Methods of Activating Retinoic Acid Receptor β (RARβ):

One aspect of the present invention pertains to use of a crystalline form of BHBA-001 (e.g., Form 4), as described herein, in a method of activating retinoic acid receptor β (RARβ) (for example, RARβ2) in vitro or in vivo, for example, in a method comprising contacting RARβ (for example, RARβ2) with an effective amount of a crystalline form of BHBA-001 (e.g., Form 4), or BHBA-001 as obtained from a crystalline form of BHBA-001 (e.g., Form 4).

One aspect of the present invention pertains to use of a crystalline form of BHBA-001 (e.g., Form 4), as described herein, in a method of selectively activating retinoic acid receptor β (RARβ) (for example, RARβ2) (e.g., with respect to RARα and/or RARγ), in vitro or in vivo, for example, in a method comprising contacting RARβ (for example, RARβ2) with an effective amount of a crystalline form of BHBA-001 (e.g., Form 4), or BHBA-001 as obtained from a crystalline form of BHBA-001 (e.g., Form 4).

One aspect of the present invention pertains to use of a crystalline form of BHBA-001, as described herein, in a method of activating retinoic acid receptor β (RARβ) (for example, RARβ2), in a neuronal cell, in vitro or in vivo, for example, in a method comprising contacting the cell with an effective amount of a crystalline form of BHBA-001 (e.g., Form 4), or BHBA-001 as obtained from a crystalline form of BHBA-001 (e.g., Form 4).

One aspect of the present invention pertains to use of a crystalline form of BHBA-001, as described herein, in a method of selectively activating retinoic acid receptor β (RARβ) (for example, RARβ2), in a neuronal cell, in vitro or in vivo, for example, in a method comprising contacting the cell with an effective amount of a crystalline form of BHBA-001 (e.g., Form 4), or BHBA-001 as obtained from a crystalline form of BHBA-001 (e.g., Form 4).

One aspect of the present invention pertains to a method of activating retinoic acid receptor β (RARβ) (for example, RARβ2) in vitro or in vivo, comprising contacting RARβ (for example, RARβ2) with an effective amount of a crystalline form of BHBA-001 (e.g., Form 4), or BHBA-001 as obtained from a crystalline form of BHBA-001 (e.g., Form 4).

One aspect of the present invention pertains to a method of selectively activating retinoic acid receptor β (RARβ) (for example, RARβ2) (e.g., with respect to RARα and/or RARγ), in vitro or in vivo, comprising contacting RARβ (for example, RARβ2) with an effective amount of a crystalline form of BHBA-001 (e.g., Form 4), or BHBA-001 as obtained from a crystalline form of BHBA-001 (e.g., Form 4).

One aspect of the present invention pertains to a method of activating retinoic acid receptor β (RARβ) (for example, RARβ2), in a neuronal cell, in vitro or in vivo, comprising contacting the cell with an effective amount of a crystalline form of BHBA-001 (e.g., Form 4), or BHBA-001 as obtained from a crystalline form of BHBA-001 (e.g., Form 4).

One aspect of the present invention pertains to a method of selectively activating retinoic acid receptor β (RARβ) (for example, RARβ2), in a neuronal cell, in vitro or in vivo, comprising contacting the cell with an effective amount of a crystalline form of BHBA-001 (e.g., Form 4), or BHBA-001 as obtained from a crystalline form of BHBA-001 (e.g., Form 4).

In one embodiment, the method is performed in vitro.
In one embodiment, the method is performed in vivo.
In one embodiment, the BHBA-001 is provided in the form of a pharmaceutically acceptable composition, for example, as obtained from a crystalline form of BHBA-001 (e.g., Form 4).

Suitable assays for determining RARβ activation (for example, RARβ2 activation) are described herein and/or are known in the art.

Use in Methods of Causing or Promoting Neurite Development, Etc.:

BHBA-001 (including crystalline forms of BHBA-001 (e.g., Form 4), as described herein) is useful for causing or promoting neurite development, neurite outgrowth, and/or neurite regeneration.

The term "neurite", as used herein, refers to a projection from the cell body of a neuron, and includes, for example, axons and dendrites.

One aspect of the present invention pertains to use of a crystalline form of BHBA-001 (e.g., Form 4), as described herein, in a method of causing or promoting neurite development, neurite outgrowth, and/or neurite regeneration, for example, in a method comprising contacting a neuron, in vitro or in vivo, with an effective amount of a crystalline form of BHBA-001 (e.g., Form 4), or BHBA-001 as obtained from a crystalline form of BHBA-001 (e.g., Form 4).

One aspect of the present invention pertains to use of a crystalline form of BHBA-001 (e.g., Form 4), as described herein, in a method of causing or promoting neurite development, for example, in a method comprising contacting a neuron, in vitro or in vivo, with an effective amount of a crystalline form of BHBA-001 (e.g., Form 4), or BHBA-001 as obtained from a crystalline form of BHBA-001 (e.g., Form 4).

One aspect of the present invention pertains to use of a crystalline form of BHBA-001 (e.g., Form 4), as described herein, in a method of causing or promoting neurite outgrowth, for example, in a method comprising contacting a neuron, in vitro or in vivo, with an effective amount of a crystalline form of BHBA-001 (e.g., Form 4), or BHBA-001 as obtained from a crystalline form of BHBA-001 (e.g., Form 4).

One aspect of the present invention pertains to use of a crystalline form of BHBA-001 (e.g., Form 4), as described herein, in a method of causing or promoting neurite regeneration, for example, in a method comprising contacting a neuron, in vitro or in vivo, with an effective amount of a crystalline form of BHBA-001 (e.g., Form 4), or BHBA-001 as obtained from a crystalline form of BHBA-001 (e.g., Form 4).

One aspect of the present invention pertains to a method of causing or promoting neurite development, neurite outgrowth, and/or neurite regeneration, comprising contacting a neuron, in vitro or in vivo, with an effective amount of a crystalline form of BHBA-001 (e.g., Form 4), or BHBA-001 as obtained from a crystalline form of BHBA-001 (e.g., Form 4).

One aspect of the present invention pertains to a method of causing or promoting neurite development, comprising contacting a neuron, in vitro or in vivo, with an effective amount of a crystalline form of BHBA-001 (e.g., Form 4), or BHBA-001 as obtained from a crystalline form of BHBA-001 (e.g., Form 4).

One aspect of the present invention pertains to a method of causing or promoting neurite outgrowth, comprising contacting a neuron, in vitro or in vivo, with an effective amount of a crystalline form of BHBA-001 (e.g., Form 4), or BHBA-001 as obtained from a crystalline form of BHBA-001 (e.g., Form 4).

One aspect of the present invention pertains to a method of causing or promoting neurite regeneration, comprising contacting a neuron, in vitro or in vivo, with an effective amount of a crystalline form of BHBA-001 (e.g., Form 4), or BHBA-001 as obtained from a crystalline form of BHBA-001 (e.g., Form 4).

In one embodiment, the method is performed in vitro.

In one embodiment, the method is performed in vivo.

In one embodiment, the BHBA-001 is provided in the form of a pharmaceutically acceptable composition, for example, as obtained from a crystalline form of BHBA-001 (e.g., Form 4).

Suitable assays for determining or measuring neurite development, neurite outgrowth, and neurite regeneration are described herein and/or are known in the art.

Use in Methods of Therapy:

Another aspect of the present invention pertains to a crystalline form of BHBA-001 (e.g., Form 4), as described herein, for use in a method of treatment of the human or animal body by therapy.

Use in the Manufacture of Medicaments:

Another aspect of the present invention pertains to use of a crystalline form of BHBA-001 (e.g., Form 4), as described herein, in the manufacture of a medicament for use in treatment.

In one embodiment, the medicament comprises the crystalline form of BHBA-001 (e.g., Form 4).

Methods of Treatment

Another aspect of the present invention pertains to a method of treatment comprising administering to a patient in need of treatment a therapeutically effective amount of a crystalline form of BHBA-001 (e.g., Form 4), or BHBA-001 as obtained from a crystalline form of BHBA-001 (e.g., Form 4), as described herein, preferably in the form of a pharmaceutical composition.

Conditions Treated

Conditions Mediated by RARβ:

In one embodiment (e.g., of use in methods of therapy, of use in the manufacture of medicaments, of methods of treatment), the treatment is treatment of a disease or condition that is mediated by RARβ (for example, RARβ2).

Conditions Ameliorated by the Activation of RARβ:

In one embodiment (e.g., of use in methods of therapy, of use in the manufacture of medicaments, of methods of treatment), the treatment is treatment of: a disease or condition that is ameliorated by the activation of RARβ (for example, RARβ2).

In one embodiment (e.g., of use in methods of therapy, of use in the manufacture of medicaments, of methods of treatment), the treatment is treatment of: a disease or condition that is ameliorated by the selective activation of RARβ (for example, RARβ2) (e.g., with respect to RARα and/or RARγ).

Neurological Injuries:

In one embodiment (e.g., of crystalline form for use in methods of therapy, of use in the manufacture of medicaments, of methods of treatment), the treatment is treatment of a neurological injury.

The term "neurological injury", as used herein, refers to any injury or damage of the nervous system, including, for example, injury or damage of the nervous system that is mechanically-induced (for example, caused by trauma); chemically-induced (for example, caused by a neurotoxin; or by a treatment regime having an immunosuppressant effect, whether by design or as a side-effect); or disease-related (for example, caused by a microbial, bacterial, fungal, or viral infection; by a neurodegenerative disorder; or by any other nerve tissue-related disorder).

In one embodiment, the treatment is treatment of an injury of the central nervous system (CNS).

In one embodiment, the treatment is treatment of an injury of the peripheral nervous system (PNS).

The term "central nervous system" (CNS), as used herein, refers to the brain and the spinal cord. The term "peripheral nervous system" (PNS), as used herein, refers to neurons, nerves, and ganglia outside of the brain and the spinal cord. The term "nervous system", as used herein, refers to both the CNS and PNS.

In one embodiment, the treatment is treatment of a nerve injury.

In one embodiment, the treatment is treatment of a PNS nerve injury.

In one embodiment, the treatment is treatment of a CNS nerve injury.

In one embodiment, the treatment is treatment of a spinal cord injury.

In one embodiment, the treatment is treatment of a spinal cord injury caused by trauma.

In one embodiment, the treatment is treatment of an optic nerve injury.

In one embodiment, the treatment is treatment of an optic nerve injury caused by glaucoma.

In one embodiment, the treatment is treatment of a neuropathy.

In one embodiment, the treatment is treatment of a PNS neuropathy.

In one embodiment, the treatment is treatment of a CNS neuropathy.

In one embodiment, the treatment is treatment of a spinal cord neuropathy.

In one embodiment, the treatment is treatment of an optic nerve neuropathy.

In one embodiment, the treatment is treatment of diabetic neuropathy (i.e., neuropathy associated with diabetes mellitus).

In one embodiment, the treatment is treatment of AIDS neuropathy (i.e., neuropathy associated with AIDS).

In one embodiment, the treatment is treatment of leprotic neuropathy (i.e., neuropathy associated with leprosy).

In one embodiment, the treatment is treatment of peripheral neuropathy (for example, polyneuropathy, mononeuropathy, mononeuritis multiplex, or autonomic neuropathy).

In one embodiment, the treatment is treatment of a neurodegenerative disorder.

In one embodiment, the treatment is treatment of a cognitive disorder, memory impairment, memory deficit, senile dementia, Alzheimer's disease, early stage Alzheimer's disease, intermediate stage Alzheimer's disease, late stage Alzheimer's disease, cognitive impairment, or mild cognitive impairment.

In one embodiment, the treatment is treatment of Huntington's disease.

In one embodiment, the treatment is treatment of Parkinson's disease.

In one embodiment, the treatment is treatment of motor neurone disease.

In one embodiment, the treatment is treatment of localised paralysis.

In one embodiment, the treatment is treatment of Bell's palsy.

In one embodiment, the treatment is treatment of neurally-based impotence.

In one embodiment, the treatment is treatment of neurally-based impotence caused by nerve trauma following radical prostatectomy.

In one embodiment, the treatment is treatment of paralysis, for example, monoplegia, quadriplegia, or paraplegia.

In one embodiment, the treatment is treatment of a neurological disorder caused by a neurological injury.

In one embodiment, the treatment is treatment of a neurological disorder caused by a neuropathy, for example, as described above.

In one embodiment, the treatment is treatment of a neurological injury caused by a neuropathy, for example, as described above.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment" (that is, treatment of condition encompasses reducing the risk of that condition).

For example, treatment includes the prophylaxis of localised paralysis, reducing the risk of localised paralysis, alleviating the symptoms of localised paralysis, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies:

The term "treatment" includes combination treatments and therapies, in which two or more treatments or therapies are combined, for example, sequentially or simultaneously. For example, the compounds described herein may also be used in combination therapies, e.g., in conjunction with other agents. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

For example, it may be beneficial to combine treatment with a compound as described herein with one or more other (e.g., 1, 2, 3, 4) agents or therapies, e.g., that treat a neurological injury.

One aspect of the present invention pertains to a compound as described herein, in combination with one or more additional therapeutic agents, as described below.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Other Uses

BHBA-001 (including crystalline forms of BHBA-001 (e.g., Form 4), as described herein) may also be used as cell culture additives to activate RARβ (e.g., RARβ2), e.g., to cause or promote neurite development, neurite outgrowth, and/or neurite regeneration.

BHBA-001 (including crystalline forms of BHBA-001 (e.g., Form 4), as described herein) may also be used, for example, as part of an in vitro assay, for example, in order to determine whether a candidate host is likely to benefit from treatment with the compound in question.

BHBA-001 (including crystalline forms of BHBA-001 (e.g., Form 4), as described herein) may also be used as a standard, for example, in an assay, in order to identify other compounds, other RARβ (e.g., RARβ2) agonists, etc.

Kits

One aspect of the invention pertains to a kit comprising (a) a crystalline form of BHBA-001 (e.g., Form 4) as described herein, or a composition comprising a crystalline form of BHBA-001 (e.g., Form 4) as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The crystalline form of BHBA-001 (e.g., Form 4) or pharmaceutical composition comprising the crystalline form of BHBA-001 (e.g., Form 4) may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human.

Furthermore, the subject/patient may be any of its forms of development, for example, a foetus.

In one preferred embodiment, the subject/patient is a human.

Formulations

While it is possible for the crystalline form of BHBA-001 (e.g., Form 4) to be administered alone, it is preferable to present it as a pharmaceutical formulation (e.g., composition, preparation, medicament) comprising a crystalline form of BHBA-001 (e.g., Form 4), as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising a crystalline form of BHBA-001 (e.g., Form 4), as described herein, together with one or more other pharmaceutically acceptable ingredients well known to those skilled in the art, e.g., carriers, diluents, excipients, etc. If formulated as discrete units (e.g., tablets, capsules, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005.

The formulations may be prepared by any methods well known in the art of pharmacy. Such methods include the step of bringing into association BHBA-001 (including, e.g., a crystalline form thereof) with a carrier which constitutes one or more accessory ingredients. In general, the formulations are prepared by uniformly and intimately bringing into association BHBA-001 (including, e.g., a crystalline form thereof, e.g., Form 4) with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with BHBA-001 (including, e.g., a crystalline form thereof, e.g., Form 4) and optionally one or more other pharmaceutically acceptable ingredients, including, for example, penetration, permeation, and absorption enhancers. Formulations may also suitably be provided in the form of a depot or reservoir.

BHBA-001 (including, e.g., a crystalline form thereof, e.g., Form 4) may be dissolved in, suspended in, or mixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavoured basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine BHBA-001 (including, e.g., a crystalline form thereof, e.g., Form 4) in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from BHBA-001 (including, e.g., a crystalline form thereof, e.g., Form 4) and a paraffinic or a water-miscible ointment base.

Creams are typically prepared from BHBA-001 (including, e.g., a crystalline form thereof, e.g., Form 4) and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from BHBA-001 (including, e.g., a crystalline form thereof, e.g., Form 4) and an oily phase, which may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of BHBA-001 (including, e.g., a crystalline form thereof, e.g., Form 4).

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichlorotetrafluoroethane, carbon dioxide, or other suitable gases.

Formulations suitable for ocular administration include eye drops wherein BHBA-001 (including, e.g., a crystalline form thereof, e.g., Form 4) is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which BHBA-001 (including, e.g., a crystalline form thereof, e.g., Form 4) is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 10 µg/mL, for example from about 10 ng/ml to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of BHBA-001 (including, e.g., a crystalline form of BHBA-001 (e.g., Form 4), as described herein), and compositions comprising BHBA-001 (including, e.g., a crystalline form of BHBA-001 (e.g., Form 4), as described herein), can vary from patient to patient.

Determining the optimal dosage will generally involve the balancing of the level of therapeutic benefit against any risk or deleterious side effects. The selected dosage level will depend on a variety of factors including, but not limited to, the activity of BHBA-001, the activity of the particular crystalline form of BHBA-001 (e.g., Form 4), as described herein, the route of administration, the time of administration, the rate of excretion of BHBA-001, the duration of the treatment, other drugs, compounds, and/or materials used in combination, the severity of the condition, and the species, sex, age, weight, condition, general health, and prior medical history of the patient. The amount of BHBA-001 (including, e.g., a crystalline form of BHBA-001 (e.g., Form 4), as described herein), and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of BHBA-001 (including, e.g., a crystalline form of BHBA-001 (e.g., Form 4), as described herein), is in the range of about 10 µg to about 250 mg (more typically about 100 µg to about 25 mg) per kilogram body weight of the subject per day.

Biological Modelling for RARβ Agonists

Biological Modelling of RARβ Agonists for Treatment of Nerve Injury-1

A simple approach to upregulate RARβ2 expression in vivo is to use an RARβ agonist, since the gene for this receptor contains an RARE, resulting in auto-regulation (see, e.g., Leid et al., 1992). Also, this is a much more practical solution than gene therapy to the treatment of CNS injuries, since retinoids are small lipophilic molecules which can potentially reach all the injured neurons, and the dose can be readily controlled.

The corticospinal tract (CST) of rats was crushed at the C4 level in rats and the RARβ agonist (CD2019, 6-(4-methoxy-3-(1-methylcyclohexyl)phenyl)-2-naphthalenecarboxylic acid, a selective RARβ agonist) was applied to the lateral ventricle in vivo for 2 weeks. The results demonstrate that CD2019 leads to an upregulation of RARβ2 in the CST neuronal cell bodies. After 5 weeks, BDA labelling of CST axons showed that in lesioned control animals, no labelled axons cross the lesion site but agonist treated rats showed a significant number of axons crossing and extending several millimeters beyond the lesion site. Specifically, in vehicle treated animals, axons (white) did not grow across a SCI, but in CD2019 treated animals, many axons were observed crossing the injury site.

In behavioural tests after 5 weeks, the CD2019 treated rats performed as well as non-lesioned animals.

The results are illustrated in Borthwick et al., 2016. FIG. 1 therein shows two graphs of the number of rat footslips as a function of the number of weeks after lesion, for grid task (A) and beam task (B). The data in FIG. 1 demonstrate that CD2019 induces functional recovery of the forelimb in lesioned animals. Rats were treated at the time of lesion by i.c.v. with CD2019 at 180 ng/kg/day for 14 days. CD2019 treated lesioned rats showed functional recovery 4 weeks post lesion in a grid task (A), and 2 weeks post lesion in a beam task (B), whereas there was no significant recovery in the vehicle treated lesioned animals. Error bar shows SEM. Asterisks denote significant difference between the lesioned treated (CD2019 or vehicle) and non-lesioned vehicle treated group. *P<0.05, students t test, n=6 rats for each treatment group.

When pieces of cortex from these RARβ agonist treated animals were cultured, neurite outgrowth was observed, in contrast to cortex from control lesioned animals. Specifically, axons did not grow from adult vehicle treated cortex, but did grow from adult CD2019 treated cortex.

Biological Modelling of RARβ Agonists for Treatment of Nerve Injury—2

In another example of nerve injury, the four sensory roots from each of four DRG at the level of the left forelimb were severed and re-implanted into the spinal cord. Rats were treated with a number of different retinoids with different selectivity profiles (as shown in the following table; all human data) as well as RARβ agonists (CD2019 and BHBA-001).

TABLE 19

| Retinoid | RARβ potency $EC_{50}$ (nM) | Selectivity over RARα | Selectivity over RARγ |
| --- | --- | --- | --- |
| 9-cis-RA | 0.74 | 7.3-fold | 1.5-fold |
| AM80 (Tamibarotene) | 7.53 | 4-fold | 6-fold |
| ATRA (Tretinoin) | 0.16 | 0.1-fold | 0.7-fold |
| 13-cis-RA (Isotretinoin) | 0.25 | 0.2-fold | 1.7-fold |
| Acitretin | 3.56 | 0.4-fold | 0.9-fold |
| CD2019 | 0.83 | 11-fold | 1.9-fold |

In behavioural test after 5 weeks, only CD2019 (a known RARβ agonist) and the BHBA-001 treated rats performed as well as non-lesioned animals.

The results are illustrated in Borthwick et al., 2016. FIG. 2 therein shows two graphs of the time taken for rats to sense sticky tape (Panel A) and to remove sticky tape (Panel B) that is placed on its injured forepaw, as a function of the number of weeks after injury. Rats were treated with 1 mg/kg of the test compound or vehicle two days after lesion, and then three times a week for the period of the experiment. Error bars show SEM. ***P<0.001, students t test, n=3-4 rats for each treatment group. At weeks 3, 4, and 5, there was significant difference between the rats treated with RARβ agonist as compared to rats treated with other retinoid agonists and vehicle.

The data in FIG. 2 further demonstrate that RARβ selectivity is required for functional recovery of the forelimb. The lesioned rats treated with RARβ agonist showed functional recovery, as indicated by sticky tape sensing (Panel A) and sticky tape removal (Panel B); there was no recovery in lesioned rats treated with any of the other retinoid agonists or vehicle.

Interaction of RARβ2 Signalling with Other Pathways Involved in Neurite Outgrowth:

The importance of the RARβ signalling pathway in axonal/neurite outgrowth was also demonstrated by illustrating its interaction with other pathways than are known to be involved in this process.

Phoshoinositide 3-Kinase Pathway:

Pathways that are known to stimulate neurite outgrowth include cyclic AMP (cAMP)-dependent protein kinase A (PKA) and phosphoinositide 3-kinase (PI3K), and these are able to overcome myelin inhibition (see, e.g., Williams et al., 2005). The authors of Borthwick et al., 2016, also examined how the RARβ signalling pathway might be linked to either of these pathways.

In cultures of cerebellar neurons grown in the presence of myelin, it was demonstrated that the RARβ agonist CD2019 causes the outgrowth of neurites and that in the presence of a PKA inhibitor which prevents cAMP signalling (KT5720), there was little or no effect on RARβ agonist mediated neurite outgrowth.

However, when the cerebellar neurons were cultured in the presence of the RARβ agonist (CD2019) and a PI3K inhibitor (LY295002), neurite outgrowth was severely impeded. Specifically, the PI3K inhibitor (LY295002) prevents RARβ agonist (CD2019) mediated neurite outgrowth in the presence of MAG, whereas the cAMP inhibitor (KT5720) does not affect RARβ agonist (CD2019) mediated outgrowth. Furthermore, Western blots of cerebellar cultures treated with 1 µM RARβ agonist CD2019 showed a significant 4-fold increase in neuronal phospho-Akt, but not total Akt, a target of PI3K, as compared to control cultures. This suggests that the RARβ agonist acts via the PI3K pathway in stimulating neurite outgrowth by increasing the phosphorylation of AKT but not the total pool of AKT. It has also been demonstrated, in vivo, that phosphor AKT is induced in the injured CST neurons by CD2019, suggesting that the agonist acts through the same mechanism as in vitro (see, e.g., Agudo et al., 2010).

While there is interest in the PI3K pathway as a target for CNS regeneration, it is difficult to prepare specific targets to the kinase itself, whereas specific RARβ agonists can be prepared which can modulate this pathway.

Biological Modelling—Details of Methods

Animal Surgery

All animal experiments were carried out under UK home office regulations. Dorsal column lesions were performed on adult male rats as previously described (see, e.g., Bradbury et al., 2002). Mini-osmotic pumps with a flow rate of 0.5 µL/hour for 14 days (Alzet™) were filled with 10 µM RARβ agonist (CD2019, obtained from CIRD Galderma, Sophia-Antipolis, France), or vehicle (10% DMSO in PBS). CD2019 is 5 fold selective RARβ over RARα and 12 fold selective RARβ over RARγ (see, e.g., Bernard et al., 1992; Delescluse et al., 1991). The pumps were placed subcutaneously and connected to a brain infusion catheter (Alzet™), which was inserted into the lateral ventricle (Bregma coordinates: rostrocaudal: −0.8 mm, mediolateral: −1.5 mm and dorsoventral: −4.5 mm). This gave a dose of CD2019 of 180 ng/kg/day. The dose was based previous in vivo studies on activation of RARα and RARβ signalling in the adult rat brain (see, e.g., Goncalves et al., 2009). Animals which underwent behavioural studies and subsequent tracing (n=6 per treatment) were kept for six weeks before being sacrificed with a lethal injection of pentobarbital and transcardially perfused with 4% PFA. Dissected tissue (cervical and lumbar spinal cord) was processed for immunofluorescence.

Western Blotting

Protein was extracted from the cortex of adult rats 14 days post surgery (n=3 per group). The amount of protein was determined using a bicinchoninic acid (BCA) protein assay kit (Pierce). Protein (10 µg) was loaded on 10% or 6% SDS-PAGE gel. Semi-dry blotting was performed, and the blots were probed with rabbit anti-RARβ (Santa Cruz, dilution of 1:500), rabbit anti-phospho-Akt, rabbit anti-Akt (both from Cell Signalling Technology, dilution of 1:1000), and mouse anti-GFAP (Sigma, dilution 1:1000). The membranes were then incubated with HRP-conjugated secondary antibodies (anti-mouse IgM+A 1:5000 from Abcam, and anti-mouse and anti-rabbit from Amersham Pharmacia Biotech 1:5000) and HRP activity was visualized by applying chemiluminescent substrate (ECL; Amersham Pharmacia Biotech) followed by exposure of the membrane to X-ray film. For a loading control, the blots were probed with mouse anti-βIII tubulin (Promega, dilution of 1:1000) and developed as above. The exposed films were analyzed by Gene Tools™ program (Syngene). Signal density was calculated as the ratio of signal intensity to β-III tubulin.

RT-PCR

RNA was isolated and cDNA synthesis was carried out as previously described (see, e.g., Corcoran et al., 2000). For PCR of rat RARβ2 (Accession no AJ002942), the following primers were used: forward (ttcgtggactttctgtgc) and reverse (tgtagaaatccaggatctgcc); which yields a product of 134 bp. These primers are rat RARβ2 specific and cannot therefore detect other RAR/RXR isoforms. Thirty cycles were carried out using the following conditions, 94° C. for 30 seconds, 56° C. for 30 seconds, and 72° C. for 30 seconds.

Neurite Outgrowth Assays

Cerebellar neurons isolated from post-natal day 3 rat pups were cultured over monolayers of parental 3T3 cells in control media, or media supplemented with a recombinant MAG-Fc chimera (R&D Systems) used at a final concentration of 20 µg/mL MAG-Fc. The monolayers were established for 24 hours prior to addition of the neurons and the co-cultures were maintained for approximately 21 hours. Following careful fixation with 4% paraformaldehyde, the neurons were immuno-stained with a GAP-43 antibody (from Graham Wilkin, Imperial College), dilution of 1:500, and the mean length of the longest neurite per cell was measured for approximately 120-150 neurons as previously described (see, e.g., Williams et al., 2005). DRG and cortical explants were obtained from adult rats, they were cultured in cellogen as previously described (see, e.g., Corcoran and Maden, 1999). Three explants per treatment were used. Neurite outgrowth was assessed 3 days later by immunohistochemistry with NF200 (Sigma, dilution of 1:200). The average lengths of the neurites were measured using image pro plus software. Media consisted of DMEM-F12 (Invitrogen) containing N2 (Invitrogen) supplemented with glucose (33 mM) and glutamine (2 mM).

Labelling of CST Neurons/Tract and Immunohistochemistry

Descendent corticospinal tract axons were anterogradely traced after the dorsal column crush was performed by injected BDA (10% in PBS, Mw10K from Molecular Probes) into the motor cortex as previously described (see, e.g., Yip et al., 2006). Six injections were done in the right cortex (0.5 µL of BDA/injection point). Animals (n=6 per treatment) were perfused and the spinal cord was transferred to PBS (plus 0.1% sodium azide) and embedded in gelatin (10%, 300 bloom; Sigma, Poole, UK). Gelatin blocks were hardened in 4% paraformaldehyde, and 40 µm free-floating serial transverse sections were cut on a vibratome (Leica, Nussloch, Germany) and collected in 24-well plates containing PBS (plus 0.1% sodium azide).

BDA was detected using the tyramide amplification kit (Perkin-Elmer) coupled with extra-avidin-FITC (Amersham Pharmacia Biotech, UK, 1:500). All BDA-labelled fibres observed within a 1-mm square grid were counted at measured intervals from 5 mm above to 5 mm below the lesion site by an experimenter, blinded to treatment. BDA positive axons were counted in every third section (5 sections per animal at each point analysed, and a total of 40 sections per animal) at the same medio-lateral distance from the midpoint (as seen by the central canal).

CST neurons were labelled by retrograde tracing injecting 2 µL of 5% Fluorogold (FG, Molecular Probes) 2 mm deep into the cervical spinal cord (C3-C4) at a rate of 0.5 µL/minute (n=3 rats per group). In sham animals, FG was injected 0.5 mm bilateral to the medial line of spinal cord (1 µL per side), and in lesioned animals FG (2 µL) was injected into the injury. After 14 days, the cortices were fixed for 2 hours in 4% paraformaldehyde (PFA), embedded in OCT compound and stored frozen. Sagittal sections (12 µm) were cut and 4 sequential slides containing 2 sections from lateral 3.4-3.9 mm were taken for analysis (see, e.g., Paxinos and Watson, 2002).

Immunohistochemistry was carried out using anti-rabbit phospho-Akt (Cell Signalling technology, dilution of 1:100). Secondary antibody used was anti-rabbit Cy3 conjugated (Jackson, used at 1:1000). Images were captured at 100× magnification using a Roperscientific digital camera.

Behavioural Testing

The behavioural tests were carried out as previously described (see, e.g., Bradbury et al., 2002). Rats (n=6 per treatment group) were first trained for two weeks before surgery to perform grid walk and beam walk; they were then tested by an observer blinded to the experimental treatment once a week for five weeks after lesion.

Graphs and Statistics

Graphs were plotted using Sigma plot. Data is expressed as mean±S.E.M and statistical analysis carried out using Student's t test using Sigma Stat software (SPSS Software Ltd, Birmingham UK). Means, SEM, SD and P-values are provided as summary statistics.

Biological Activity for BHBA-001

Transactivation assays for RARα, RARβ, and RARγ Receptors

Transcriptional transactivation assays were performed with gal4 fusion receptor constructs, created using each of the RAR ligand binding domains of either mouse or human, co-transfected with the pFR-luc (Stratagene) reporter construct in COS-7 cells. Thus, transfected cells will constitutively express the gal4-RAR fusion protein which in turn may be transactivated by all trans retinoic acid (atRA) to induce the expression of the luciferase that is driven by a gal4UAS.

Briefly, on day 1, 96 well plates were seeded with 8000 cells per well then left to recover overnight. On day 2, the cells were co-transfected with 100 ng of reporter plasmid and 10 ng of the appropriate receptor plasmid per well using lipofectamine (Invitrogen). On day 3, the lipofectamine containing media was replaced by a DMEM without phenol red, followed by the addition of test compound dissolved in 1 µL of DMSO to each well's 100 µL total volume. Finally, on day 4, the cells were lysed and their luciferase substrate was provided by the BrightGlo™ reagent (Promega), the plates were then read on the MicroBeta TrLux™ (Perkin Elmer).

On each plate, an 8 point dose-response curve of atRA was run in duplicate and dose-response curves of test compounds were also generated in duplicate.

$EC_{50}$ data both for test compounds and atRA was generated by fitting dose-response curves using GraphPad Prism™. Data for test compounds are quoted as $EC_{50}$ values. Where replicate data has been generated, the data are quoted as the mean $EC_{50}$ from the separate experiments.

The data are summarised in the following table. $EC_{50}$'s values are reported as mean values of three or more determinations.

TABLE 20

Activity and Selectivity Data

| Code No. | RARβ $EC_{50}$ (nM) | RARα $EC_{50}$ (nM) | RARγ $EC_{50}$ (nM) | RARα/RARβ ratio (*) | RARγ/RARβ ratio (**) |
|---|---|---|---|---|---|
| atRA | 1.88 | 1.2 | 0.9 | 0.6 | 0.5 |
| BHBA-001 | 1.94 | 26 | 11 | 13.4 | 5.6 |

(*) The ratio of the "RARα activity" to the "RARβ activity" is referred to as "RARα/RARβ ratio" and reflects the fold-selectivity for RARβ over RARα. A value greater than 1 indicates selectivity for RARβ.

(**) The ratio of the "RARγ activity" to the "RARβ activity" is referred to as "RARγ/RARβ ratio" and reflects the fold-selectivity for RARβ over RARγ. A value greater than 1 indicates selectivity for RARβ.

BHBA-001 is an agonist of RARβ, with an RARβ activity of less than 2 nM.

BHBA-001 is also selective for RARβ as compared to RARα: the selectivity for RARβ as compared to RARα is by a factor of about 13.4.

BHBA-001 is also selective for RARβ as compared to RARγ: the selectivity for RARβ as compared to RARγ is by a factor of about 5.6.

Additional mouse and human data for two preferred compounds is summarised in the following table.

TABLE 21

Activity and Selectivity Data

| Mammal | Compound | BHBA-001 |
|---|---|---|
| Mouse | RARβ potency - $EC_{50}$ (nM) | 1.94 |
| | Selectivity over RARα | 14-fold |
| | Selectivity over RARγ | 6-fold |
| Human | RARβ potency - $EC_{50}$ (nM) | 2.05 |
| | Selectivity over RARα | 23-fold |
| | Selectivity over RARγ | 5-fold |

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of patents and publications are cited herein in order to more fully describe and disclose the invention and the state of the art to which the invention pertains. Full citations for these references are provided below.

Each of these references is incorporated herein by reference in its entirety into the present disclosure, to the same extent as if each individual reference was specifically and individually indicated to be incorporated by reference.

Agudo M, Yip P, Davies M, Bradbury E, Doherty P, McMahon S, Maden M, Corcoran J P (2010) A retinoic acid receptor beta agonist (CD2019) overcomes inhibition of axonal outgrowth via phosphoinositide 3-kinase signalling in the injured adult spinal cord. Neurobiol Dis 37:147-155.

Bastien J, Rochette-Egly C (2004) Nuclear retinoid receptors and the transcription of retinoid-target genes. Gene 328:1-16.

Bernard et al., 1992, "Identification of synthetic retinoids with selectivity for human nuclear retinoic acid receptor gamma", Biochem. Biophys. Res. Commun., Vol. 186, pp. 977-983.

Borthwick et al., 2016, "Bicycloheteroaryl-heteroaryl-benzoic acid compounds as retinoic acid receptor beta (RARβ) agonists", international patent application number PCT/EP2015/080029 filed 16 Dec. 2015, published as WO 2016/097004 A1 on 23 Jun. 2016.

Bradbury E J, Moon L D, Popat R J, King V R, Bennett G S, Patel P N, Fawcett J W, McMahon S B (2002) Chondroitinase ABC promotes functional recovery after spinal cord injury. Nature 416:636-640.

Cai et al., 2003, "Substituted 3-aryl-5-aryl-[1,2,4]-oxadiazoles and analogs as activators of caspases and inducers of apoptosis and the use thereof", US Patent Publication No. 2003/0045546 A1 published 6 Mar. 2003.

Cai et al., 2005, "Substituted 3-aryl-5-aryl-[1,2,4]-oxadiazoles and analogs as activators of caspases and inducers of apoptosis and the use thereof", US Patent Publication No. 2005/0154012 A1 published 14 Jul. 2005.

Corcoran J, Maden M (1999) Nerve growth factor acts via retinoic acid synthesis to stimulate neurite outgrowth [letter]. Nat Neurosci 2:307-308.

Corcoran J, Shroot B, Pizzey J, Maden M (2000) The role of retinoic acid receptors in neurite outgrowth from different populations of embryonic mouse dorsal root ganglia [In Process Citation]. J Cell Sci 113 (Pt 14):2567-2574.

Corcoran J, So P L, Barber R D, Vincent K J, Mazarakis N D, Mitrophanous K A, Kingsman S M, Maden M (2002) Retinoic acid receptor beta2 and neurite outgrowth in the adult mouse spinal cord in vitro. J Cell Sci 115:3779-3786.

Delescluse et al., 1991, "Selective high affinity retinoic acid receptor alpha or beta-gamma ligands," Mol. Pharmacol., Vol. 40, pp. 556-562.

Goncalves et al., 2009, "Sequential RARbeta and alpha signalling in vivo can induce adult forebrain neural progenitor cells to differentiate into neurons through Shh and FGF signalling pathways", Dev. Biol., Vol. 326, pp. 305-313.

He Z, Koprivica V (2004) The nogo signaling pathway for regeneration block. Annu Rev Neurosci 27:341-368.

Kikuchi et al., 2000, "Synthesis and structure-activity relationships of 5,6,7,8-tetrahydro-5,5,8,8-tetramethyl-2-quinoxaline derivatives with retinoic acid receptor α activity", J. Med. Chem., Vol. 43, pp. 409-419.

Kikuchi et al., 2001, "Heterocycle-containing carboxylic acid derivative and drug containing the same", U.S. Pat. No. 6,329,402 granted 11 Dec. 2001.

Kwon B K, Tetzlaff W (2001) Spinal cord regeneration: from gene to transplants. Spine 26:S13-S22.

Leid M, Kastner P, Chambon P (1992) Multiplicity generates diversity in the retinoic acid signalling pathways. Trends Biochem Sci 17:427-433.

Lund et al., 2005, "Discovery of a potent, orally available, and isoform-selected retinoica acid β2 receptor agonist", J. Med. Chem., Vol. 48, pp. 7517-7519.

Maden and Corcoran, 2000, "Factor", international patent (PCT) publication number WO 00/57900 A2, published 5 Oct. 2000.

Maden et al., 1996, "Vitamin A-deficient quail embryos have half a hindbrain and other neural defects", Curr. Biol., Vol. 6, pp. 417-426.

Olsson et al., 2009, "Compounds with activity at retinoic acid receptors", US Patent Publication No. 2009/0176837 A1 published 9 Jul. 2009.

Paxinos and Watson, 2002, "The Rat Brain in Stereotaxic Coordinates", 2nd edition, Academic Press, London.

Quinn S D, De Boni U (1991) Enhanced neuronal regeneration by retinoic acid of murine dorsal root ganglia and of fetal murine and human spinal cord in vitro. In Vitro Cell Dev Biol 27:55-62.

Schnell L, Schneider R, Kolbeck R, Barde Y A, Schwab M E (1994) Neurotrophin-3 enhances sprouting of corticospinal tract during development and after adult spinal cord lesion [see comments]. Nature 367:170-173.

Seino et al., 2004, "Prevention of acute and chronic allograft rejection by a novel retinoic acid receptor-α-selective agonist", Inter. Immunology, Vol. 16, No. 5, pp. 665-673.

So P L, Yip P K, Bunting S, Wong L F, Mazarakis N D, Hall S, McMahon S, Maden M, Corcoran J P (2006) Interactions between retinoic acid, nerve growth factor and sonic hedgehog signalling pathways in neurite outgrowth. Dev Biol 298:167-175.

Tagami et al., 1997, "Fused-ring carboxylic acid derivatives", European patent publication number E P 0889032 A1, published 7 Jan. 1999.

Tagami et al., 2000a, "Fused-ring carboxylic acid derivatives", U.S. Pat. No. 6,121,309 granted 19 Sep. 2000.

Tagami et al., 2000b, "Carboxylic acid derivatives having fused rings", U.S. Pat. No. 6,110,959 granted 29 Aug. 2000.

Tagami et al., 2002, "Carboxylic acid derivatives having fused rings," U.S. Pat. No. 6,358,995 granted 19 Mar. 2002.

Tsuda et al., 1999, "Pyrrole derivatives and medicinal composition", U.S. Pat. No. 5,998,459 granted 7 Dec. 1999.

White et al., 1998, "Defects in embryonic hindbrain development and fetal resorption resulting from vitamin A deficiency in the rat are prevented by feeding pharmacological levels of all-trans-retinoic acid", Proc. Natl. Acad. Sci. USA, Vol. 95, pp. 13459-12364.

Williams G, Eickholt B J, Maison P, Prinjha R, Walsh F S, Doherty P (2005) A complementary peptide approach applied to the design of novel semaphorin/neuropilin antagonists. J Neurochem 92:1180-1190.

Wong L F, Yip P K, Battaglia A, Grist J, Corcoran J, Maden M, Azzouz M, Kingsman S M, Kingsman A J, Mazarakis N D, McMahon S B (2006) Retinoic acid receptor beta2 promotes functional regeneration of sensory axons in the spinal cord. Nat Neurosci 9:243-250.

Yip P K, Wong L F, Pattinson D, Battaglia A, Grist J, Bradbury E J, Maden M, McMahon S B, Mazarakis N D (2006) Lentiviral vector expressing retinoic acid receptor beta2 promotes recovery of function after corticospinal tract injury in the adult rat spinal cord. Hum Mol Genet 15:3107-3118.

Yoshimura et al., 2000, "Discovery of novel and potent retinoic acid receptor α agonists: synthesis and evaluation of benzofuranyl-pyrrole and benzothiophenyl-pyrrole derivatives", J. Med. Chem., Vol. 43, pp. 2929-2937.

The invention claimed is:

1. A method of preparing a crystalline form of 4-(5-(4,7-dimethylbenzofuran-2-yl)-1,2,4-oxadiazol-3-yl)benzoic acid having an X-ray powder diffraction that exhibits characteristic scattering angles (2θ) at least at: 14.8°±0.2°, 20.7°±0.2°, and 9.5°±0.2, comprising the steps, in order:
   a) heating a mixture of 4-(5-(4,7-dimethylbenzofuran-2-yl)-1,2,4-oxadiazol-3-yl)benzoic acid and ethanol; and
   b) cooling said mixture; and
   c) isolating said crystalline form from said mixture.

2. The method of claim 1, wherein said mixture of 4-(5-(4,7-dimethylbenzofuran-2-yl)-1,2,4-oxadiazol-3-yl)benzoic acid and ethanol is a slurry of solid 4-(5-(4,7-dimethylbenzofuran-2-yl)-1,2,4-oxadiazol-3-yl)benzoic acid and ethanol.

3. The method of claim 1, wherein said heating is at a temperature of about 40° C. to the reflux temperature of said mixture.

4. The method of claim 1, wherein said heating is for a period of about 30 minutes to about 24 hours.

5. The method of claim 1, wherein said cooling is to a temperature of about 5° C. to about 30° C.

6. The method of claim 1, wherein said cooling is followed by a step of (b') ageing said cooled mixture.

7. The method of claim 6, wherein said ageing is for a period of about 30 minutes to about 24 hours.

8. A method of activating retinoic acid receptor β (RARβ), in vitro or in vivo, comprising contacting RARβ with an effective amount of:
   a crystalline form of 4-(5-(4,7-dimethylbenzofuran-2-yl)-1,2,4-oxadiazol-3-yl)benzoic acid having an X-ray powder diffraction that exhibits characteristic scattering angles (2θ) at least at: 14.8°±0.2°, 20.7°±0.2°, and 9.5°±0.2°, or
   4-(5-(4,7-dimethylbenzofuran-2-yl)-1,2,4-oxadiazol-3-yl)benzoic acid as obtained from a crystalline form of 4-(5-(4,7-dimethylbenzofuran-2-yl)-1,2,4-oxadiazol-3-yl)benzoic acid having an X-ray powder diffraction that exhibits characteristic scattering angles (2θ) at least at: 14.8°±0.2°, 20.7°±0.2°, and 9.5°±0.2°.

9. The method of claim 8, wherein the method is a method of selectively activating retinoic acid receptor β (RARβ), with respect to RARα and/or RARγ.

10. The method according to claim 8, wherein the method is a method of activating retinoic acid receptor β (RARβ), in a neuronal cell, in vitro or in vivo, comprising contacting the cell with an effective amount of:
   a crystalline form of 4-(5-(4,7-dimethylbenzofuran-2-yl)-1,2,4-oxadiazol-3-yl)benzoic acid having an X-ray powder diffraction that exhibits characteristic scattering angles (2θ) at least at: 14.8°±0.2°, 20.7°±0.2°, and 9.5°±0.2°, or
   4-(5-(4,7-dimethylbenzofuran-2-yl)-1,2,4-oxadiazol-3-yl)benzoic acid as obtained from a crystalline form of 4-(5-(4,7-dimethylbenzofuran-2-yl)-1,2,4-oxadiazol-3-yl)benzoic acid having an X-ray powder diffraction that exhibits characteristic scattering angles (2θ) at least at: 14.8°±0.2°, 20.7°±0.2°, and 9.5°±0.2°.

11. The method of claim 10, wherein the method is a method of selectively activating retinoic acid receptor β (RARβ), in a neuronal cell, in vitro or in vivo.

12. A method of causing or promoting neurite development, neurite outgrowth, and/or neurite regeneration, comprising contacting a neuron, in vitro or in vivo, with an effective amount of:
   a crystalline form of 4-(5-(4,7-dimethylbenzofuran-2-yl)-1,2,4-oxadiazol-3-yl)benzoic acid having an X-ray powder diffraction that exhibits characteristic scattering angles (2θ) at least at: 14.8°±0.2°, 20.7°±0.2°, and 9.5°±0.2°, or
   4-(5-(4,7-dimethylbenzofuran-2-yl)-1,2,4-oxadiazol-3-yl)benzoic acid as obtained from a crystalline form of 4-(5-(4,7-dimethylbenzofuran-2-yl)-1,2,4-oxadiazol-3-yl)benzoic acid having an X-ray powder diffraction that exhibits characteristic scattering angles (2θ) at least at: 14.8°±0.2°, 20.7°±0.2°, and 9.5°±0.2°.

13. A method of treating:
   a neurological injury;
   an injury of the central nervous system (CNS);
   an injury of the peripheral nervous system (PNS);
   a nerve injury;
   a PNS nerve injury;
   a CNS nerve injury;
   a spinal cord injury;
   a spinal cord injury caused by trauma;
   an optic nerve injury;
   an optic nerve injury caused by glaucoma;

a neuropathy;
a PNS neuropathy;
a CNS neuropathy;
a spinal cord neuropathy;
an optic nerve neuropathy;
diabetic neuropathy;
AIDS neuropathy;
leprotic neuropathy;
peripheral neuropathy;
polyneuropathy;
mononeuropathy;
mononeuritis multiplex;
autonomic neuropathy;
a neurodegenerative disorder;
a cognitive disorder;
memory impairment;
memory deficit;
senile dementia;
Alzheimer's disease;
early stage Alzheimer's disease;
intermediate stage Alzheimer's disease;
late stage Alzheimer's disease;
cognitive impairment;
mild cognitive impairment;
Huntington's disease;
Parkinson's disease;
motor neurone disease;
localised paralysis;
Bell's palsy;
neurally-based impotence;
neurally-based impotence caused by nerve trauma following radical prostatectomy;
paralysis;
monoplegia;
quadriplegia;
paraplegia;
a neurological disorder caused by a neurological injury;
a neurological disorder caused by a neuropathy; or
a neurological injury caused by a neuropathy;
comprising administering to a subject in need thereof a therapeutically effective amount of:
a crystalline form of 4-(5-(4,7-dimethylbenzofuran-2-yl)-1,2,4-oxadiazol-3-yl)benzoic acid having an X-ray powder diffraction that exhibits characteristic scattering angles (2θ) at least at: 14.8°±0.2°, 20.7°±0.2°, and 9.5°±0.2°, or
4-(5-(4,7-dimethylbenzofuran-2-yl)-1,2,4-oxadiazol-3-yl)benzoic acid as obtained from a crystalline form of 4-(5-(4,7-dimethylbenzofuran-2-yl)-1,2,4-oxadiazol-3-yl)benzoic acid having an X-ray powder diffraction that exhibits characteristic scattering angles (2θ) at least at: 14.8°±0.2°, 20.7°±0.2°, and 9.5°±0.2°.

* * * * *